US009255088B2

(12) United States Patent
Gatti et al.

(10) Patent No.: US 9,255,088 B2
(45) Date of Patent: Feb. 9, 2016

(54) PREMATURE-TERMINATION-CODONS READTHROUGH COMPOUNDS

(71) Applicant: The Regents of the University of California, Oakland, CA (US)

(72) Inventors: Richard Gatti, Sherman Oaks, CA (US); Liutao Du, Los Angeles, CA (US); Robert Damoiseaux, Beverly Hills, CA (US); Chih-Hung Lai, Cerritos, CA (US); Michael Jung, Los Angeles, CA (US); Jin-Mo Ku, Los Angeles, CA (US); Carmen Bertoni, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 542 days.

(21) Appl. No.: 13/764,748

(22) Filed: Feb. 11, 2013

(65) Prior Publication Data
US 2013/0274283 A1    Oct. 17, 2013

Related U.S. Application Data

(63) Continuation of application No. PCT/US2011/047421, filed on Aug. 11, 2011.

(60) Provisional application No. 61/372,768, filed on Aug. 11, 2010.

(51) Int. Cl.
| | |
|---|---|
| *C07D 413/06* | (2006.01) |
| *C07D 307/52* | (2006.01) |
| *C07C 251/24* | (2006.01) |
| *C07C 215/76* | (2006.01) |
| *C07C 335/16* | (2006.01) |
| *C07D 407/06* | (2006.01) |
| *C07D 221/16* | (2006.01) |
| *C07D 285/12* | (2006.01) |
| *C07D 207/273* | (2006.01) |
| *C07D 409/06* | (2006.01) |
| *C07C 207/04* | (2006.01) |
| *C07C 291/04* | (2006.01) |

(52) U.S. Cl.
CPC ............ *C07D 413/06* (2013.01); *C07C 207/04* (2013.01); *C07C 215/76* (2013.01); *C07C 251/24* (2013.01); *C07C 291/04* (2013.01); *C07C 335/16* (2013.01); *C07D 207/273* (2013.01); *C07D 221/16* (2013.01); *C07D 285/12* (2013.01); *C07D 307/52* (2013.01); *C07D 407/06* (2013.01); *C07D 409/06* (2013.01)

(58) Field of Classification Search
None
See application file for complete search history.

(56) References Cited

U.S. PATENT DOCUMENTS

| 3,637,734 A | 1/1972 | Harnisch et al. |
|---|---|---|
| 3,906,010 A | 9/1975 | Pelosi, Jr. et al. |
| 5,554,767 A | 9/1996 | Wang et al. |
| 2009/0163545 A1 | 6/2009 | Goldfarb |

FOREIGN PATENT DOCUMENTS

| GB | 2387172 A | 10/2003 |
|---|---|---|
| JP | 11-302280 | 11/2011 |
| WO | WO 00/10573 A1 | 3/2000 |
| WO | WO 00/32598 A1 | 6/2000 |
| WO | WO 01/77091 A2 | 10/2001 |
| WO | WO 2004/028535 A1 | 4/2004 |
| WO | WO 2005/037257 A2 | 4/2005 |
| WO | WO 2009/015922 A1 | 2/2009 |
| WO | WO 2011/063602 A1 | 6/2011 |

OTHER PUBLICATIONS

CAS Registry No. 29095-25-8, Nov. 16, 1984.
CAS Registry No. 73855-59-1, Nov. 16, 1984.
CAS Registry No. 312925-94-3, Jan. 5, 2001.
CAS Registry No. 312926-79-7, Jan. 5, 2001.
CAS Registry No. 333393-11-6, Apr. 30, 2001.
CAS Registry No. 333393-23-0, Apr. 30, 2001.
CAS Registry No. 370081-35-9, Nov. 15, 2001.
CAS Registry No. 401640-08-2, Mar. 18, 2002.
CAS Registry No. 471918-99-7, Nov. 8, 2002.
CAS Registry No. 471919-11-6, Nov. 8, 2002.
CAS Registry No. 892100-22-0, Jul. 11, 2006.
CAS Registry No. 925397-33-7, Mar. 7, 2007.
CAS Registry No. 1223469-97-3, May 14, 2010.
CAS Registry No. 1227733-71-2, Jun. 15, 2010.
Ceasar et al., "Orbital Interaction in 2a,8b-Dihydrocyclopent [cd] Azulene", *Tetrahedron Letters* (1968) 20:1721-1724.
Du et al., "Nonaminoglycoside compounds induce readthrough of nonsense mutations", *Journal of Experimental Medicine* (2009) 206:2285-2297.
Du et al., "Rapid screen for truncating ATM mutations by PTT-ELISA", *Mutation Research* (2008) 640:139-144.
Felise et al., "An Inhibitor of Gram-Negative Bacterial Virulence Protein Secretion", *Cell Host & Microbe* (2008) 4:325-336.
Gränacher et al., Über die Verwendung des Rhodanins zu organischen Synthesen IV. Indol- and Furyl-Brenztraubensäure, *Helvetica Chimica Acta* (1924) 7:575-578.

(Continued)

*Primary Examiner* — Addison D Ault
(74) *Attorney, Agent, or Firm* — Squire Patton Boggs (US) LLP

(57) ABSTRACT

Premature termination codons readthrough compounds, composition thereof, and methods of making and using the same are provided.

6 Claims, 21 Drawing Sheets

(56) References Cited

OTHER PUBLICATIONS

Hallgas et al., "Comparison of measured and calculated lipophilicity of substituted aurones and related compounds", *Journal of Chromatography B* (2004) 801:229-235.

Jung et al., "Synthesis and evaluation of compounds that induce readthrough of premature termination codons", *Bioorganic & Medicinal Chemistry Letters* (2011) 21:5842-5848.

Kloc et al., "Reactions at the nitrogen atoms in azafluorene systems", *Canadian Journal of Chemistry* (1979) 57:1506-1510.

Lai et al., "Correction of ATM gene function by aminoglycoside-induced read-through of premature termination codons", *Proc. Nat'l. Acad. Sci. USA* (2004) 101:15676-15681.

Law, H.B., "Electrolytic Oxidation", *Journal of the Chemical Society, Transactions* (1906) 89:1437-1453.

Libermann et al., "La Thiazolidione, point de départ d'une synthèse des acides thiopyruviques et thioglyoxyliques substiués", *Bulletin de la Société Chimique de France* (1948) 1120-1124.

Midituru et al., "High-Throughput Kinase Profiling: A More Efficient Approach toward the Discovery of New Kinase Inhibitors", *Chemistry & Biology* (2011) 18:868-879.

Mure et al., "Model Studies of Topaquinone-Dependent Amine Oxidases. 1. Oxidation of Benzylamine by Topaquinone Analogs", *Journal of the American Chemical Society* (1995) 1117:8698-8706.

Pinson et al., "Thiazolidinedione-Based PI3Kα Inhibitors: An Analysis of Biochemical and Virtual Screening Methods", *ChemMedChem* (2011) 6:514-522.

Pope, F.G., "Colour and constitution of azomethine compounds. Part 1.", *Proceedings of the Chemical Society*, London (1908) 24:24.

Richardson et al., "Discovery of a potent CDK2 inhibitor with a novel binding mode, using virtual screening and initial, structure-guided lead scoping", *Bioorganic & Medicinal Chemistry Letters* (2007) 17:3880-3885.

Stevens et al., "Physostigmine Subsitutes", *Journal of the American Chemical Society* (1941) 63:308-311.

Wheeler et al., "On some aldehyde condensation producs of arylpseudothiohydantoins", *Journal of the American Chemical Society* (1903) 25:366-371.

Zelenin et al., "Synthesis and Structure of Thioacylhydrazones", translated from Russian *Journal of Organic Chemistry of the USSR* (1984) 20:152-167.

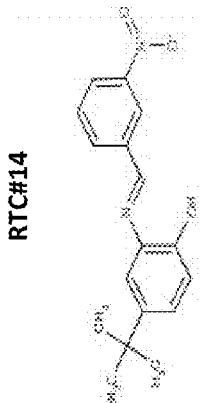 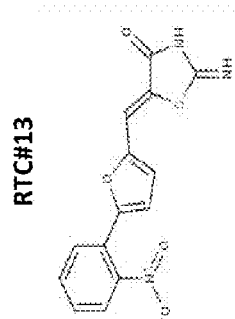 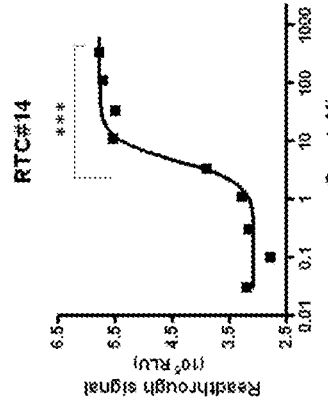 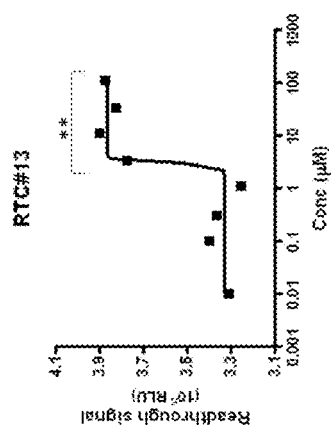 
Figures 2a-2c

PREMATURE-TERMINATION-CODONS READTHROUGH COMPOUNDS

CROSS-REFERENCE TO RELATED APPLICATIONS

This application is a continuation application of International Patent Application No. PCT/US11/47421 filed on Aug. 11, 2011, which in turn claims the benefit of U.S. Provisional Patent Application No. 61/372,768, filed Aug. 11, 2010, the teaching of each of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. NS035322 and NS052528, awarded by the National Institutes of Health. The Government has certain rights in this invention.

FIELD OF THE INVENTION

The invention provides premature-termination-codon (PTC) readthrough-inducing compounds and methods of making and using the same.

BACKGROUND OF THE INVENTION

Large numbers of genetic disorders are caused by nonsense mutations for which compound-induced readthrough of premature termination codons (PTCs) might be exploited as a potential treatment strategy. We have successfully developed a sensitive and quantitative high-throughput screening (HTS) assay, protein transcription/translation (PTT)-enzyme-linked immunosorbent assay (ELISA), for identifying novel. PTC-readthrough compounds using ataxia-telangiectasia (A-T) as a genetic disease model. This HTS PTT-ELISA assay is based on a coupled PTT that uses plasmid templates containing prototypic A-T imitated (ATM) mutations for HTS. The assay is luciferase independent. We screened ~34,000 compounds and identified 12 low-molecular-mass nonaminoglycosides with potential PTC-readthrough activity. From these, two leading compounds consistently induced functional ATM protein in ATM-deficient cells containing disease-causing nonsense mutations, as demonstrated by direct measurement of ATM protein, restored ATM kinase activity, and colony survival assays for cellular radiosensitivity. The two compounds also demonstrated readthrough activity in mdx mouse myotube cells carrying a natural nonsense mutation and induced significant amounts of dystrophin protein.

Translation termination is signaled by three stop codons: UAA, UAG, and UGA. This mechanism is highly conserved, although each stop codon has a different efficiency for terminating translation. UGA is considered to be a "leaky" stop codon with the highest intrinsic readthrough potential. UAA shows high fidelity and little intrinsic readthrough potential, whereas UAG has intermediate fidelity (see, e.g., Weiner and Weber, 1973, *J. Mol. Biol.* 80:837-855). Nonsense mutations create primary premature termination codons (PTCs) and result in either no formation of the target protein or truncated protein with impaired stability.

Certain compounds influence the fidelity of stop codon recognition and induce readthrough of primary PTCs, which allows translation of some full-length protein. In many cases, the readthrough-induced protein is functional, even when it contains a wrongly incorporated amino acid (Keeling and Bedwell, 2005, *Current Pharmacogenomics.* 3:259-269; Zingman et al., 2007, *Clin. Pharmacol. Ther.* 81:99-103).

It is estimated that 30% of human disease-causing alleles are nonsense mutations (Du et al., 2009, JEM, 206 (10): 2285). Other types of mutation, such as frameshift and splicing mutations, lead to secondary PTCs; however, these are not therapeutic targets for readthrough compounds (RTCs). Considering that >1,800 distinct genetic disorders are caused by nonsense mutations, the readthrough of primary PTCs has treatment potential for large numbers of patients.

To date, most reported PTC-RTCs that are active in mammalian cells have belonged to the aminoglycoside antibiotics class (Keeling and Bedwell, 2005; Zingman et al., 2007). Certain types of aminoglycosides can induce ribosomes to read through PTC mutations via insertion of a random amino acid by near-cognate transfer RNA. The therapeutic potential of aminoglycosides has been evaluated in the laboratory for different genetic models, such as cystic fibrosis (see, e.g., Du et al., 2002, *J. Mol. Med.* 80:595-604), muscular dystrophy (see, e.g., Loufrani et al., 2004, *Arterioscler. Thromb. Vasc. Biol.* 24:671-676), Hurler syndrome (Keeling et al., 2001, *Hum. Mol. Genet.* 10:291-299), cystinosis (Helip-Wooley et al., 2002, *Mol. Genet. Metab.* 75:128-133), spinal muscular atrophy (Sossi et al., 2001, *Eur. J. Hum. Genet.* 9:113-120), ataxia-telangiectasia (Lai et al., 2004, *Proc. Natl. Acad. Sci. USA.* 101:15676-15681), and type 1 Usher syndrome (Rebibo-Sabbah et al., 2007, *Hum. Genet.* 122:373-381). Clinical trials also indicate that aminoglycosides can induce some functional protein production; however, the therapeutic benefits remain uncertain (see, e.g., Politano et al., 2003, *Acta Myol.* 22:15-21). Furthermore, the toxicity of most commercial aminoglycosides in mammals has greatly diminished their potential for successful readthrough therapy (Mingeot-Leclercq and Tulkens, 1999, *Antimicrob. Agents Chemother.* 43:1003-1012; Guan et al., 2000, *Hum. Mol. Genet.* 9:1787-1793). Therefore, efforts are underway to develop better aminoglycoside derivatives with reduced toxicity and enhanced activity (Nudelman et al., 2006, *Bioorg. Med. Chem. Lett.* 16:6310-6315; Rebibo-Sabbah et al., 2007, *Hum. Genet.* 122: 373-381). Recently, PTC Therapeutics (South Plainfield, N.J.) described a more efficient nonaminoglycoside RTC, PTC124, which was developed synthetically by screening >800,000 chemicals and analogues using a luciferase-based high-throughput screening (HTS) assay (see, e.g., Welch et al., 2007, *Nature.* 447:87-91). A phase-I clinical study in cystic fibrosis confirmed that PTC124 is generally well tolerated and appears to have more efficient readthrough activity than aminoglycosides (Hirawat et al., 2007, *J. Clin. Pharmacol.* 47:430-444). Moreover, PTC 124 does not induce ribosomal readthrough of normal stop codons. A phase-II clinical trial is underway (Kerem et al., 2008, *Lancet.* 372:719-727). However, a recent study indicates that the initial discovery of PTC124 by HTS may have been biased by its direct effect on the FLuc (firefly luciferase) reporter used (Auld et al., 2009, *Proc. Natl. Acad. Sci. USA.* 106:3585-3590), indicating the importance of a luciferase-independent HTS assay for future drug screening.

SUMMARY OF THE INVENTION

In one aspect of the present invention, it provides a system for high throughput assay for readthrough compound having the ability to read through premature termination codons (PTCs) in RNA. The system comprises high throughput reading trays and wells containing a plasmid, wherein the plasmid comprises a fragment of ATM gene that contains a PTC mutation, which fragment being flanked by a sequence that initiates transcription of: a) a myc epitope, b) the ATM fragment, and c) a V5 epitope;

wherein the assay is based on a coupled protein transcription/translation (PTT) reaction that is driven by the plasmid;

wherein the reading trays are coated with an antibody to the myc epitope; and wherein an antibody to V5 is provided for attaching to readthrough proteins expressing the V5 epitope.

In some embodiments of the system, the V5 epitope is conjugated to horseradish peroxidase.

In some further embodiments of the system, the system comprises a robot.

In another aspect of the present invention, it is provided a method of screen for readthrough compounds having the ability to read through premature termination codons (PTCs) in RNA. The method comprises:

providing a plasmid template to a reaction well having a test compound to cause a coupled protein transcription/translation (PTT) reaction to occur to generate a PTT reaction product, the plasmid template comprising a fragment of ATM gene that contains a PTC mutation, which fragment being flanked by a sequence that initiates transcription of: a) a myc epitope, b) the ATM fragment, and c) a V5 epitope;

adding the PTT reaction product to high throughput reading trays, which are coated with an antibody to the myc epitope to capture a protein fragment of the fragment of ATM gene, adding an antibody to the V5 epitope (V5 antibody) to wells in the reading trays, detecting the attachment of the V5 antibody to proteins in the PTT product, and identifying the test compound as a readthrough compound if the attachment of the V5 antibody to proteins in the PTT product occurs.

In some embodiments of the method, the V5 epitope is conjugated to horseradish peroxidase.

In some embodiments of the method, detecting is achieved by a chemiluminescence reaction as read out.

In a further embodiment of the present invention, it is provided a compound having the ability to read through premature termination codons (PTCs) in RNA, a pharmaceutically acceptable salt thereof or a prodrug thereof. The compound comprises moiety (I) and/or moiety (II):

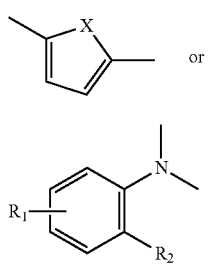

wherein:
X is O or S;
$R_1$ is ortho, meta, or para to $R_2$ and is a hydrogen, C1-C6 group, hydroxyl, alkoxy, halo, amino, alkylamino, thiol, alkylthio, sulfonyl, nitro, formyl, or carboxyl group, and
$R_2$ is a hydroxyl, methoxy, ethoxy, halo, amino, alkylamino, thiol, alkylthio, sulfonyl, nitro, or carboxyl group.

Some embodiments of compounds comprising moiety (I) specifically exclude RTC 13, and some embodiments of compounds comprising moiety (II) specifically excludes RTC14.

When referring to a specific compound, the term "RTC" is used interchangeably with the term "RTC#".

In some embodiments of the compound, it has a structure of formula (III)

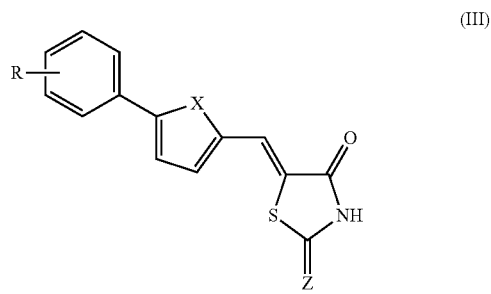

wherein:
X is O or S;
Z is O, S, or NR' where R' is hydrogen or a C1-C6 group, e.g., methyl, ethyl, isopropyl, t-butyl, n-butyl, pentyl, n-hexyl, vinyl, or allyl; and
R is an ortho, meta, or para group and is a hydrogen, C1-C6 group, hydroxyl group, alkoxy, halo, amino, alkylamino, thiol, alkylthio, sulfonyl, nitro, formyl, or carboxyl group.

In some embodiments of the compound, it has a structure of one of the following formula

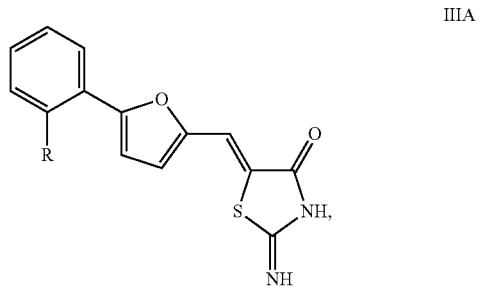

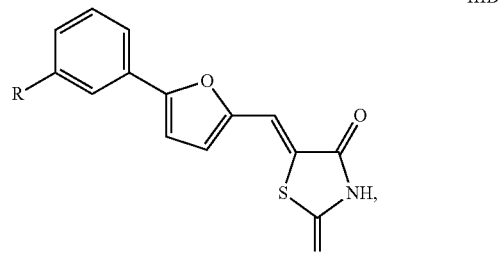

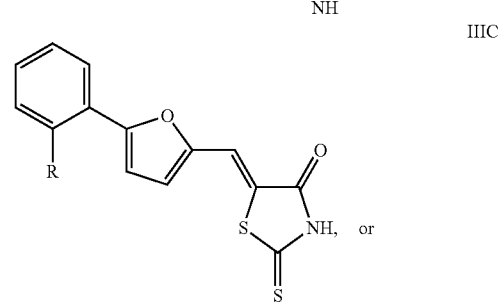

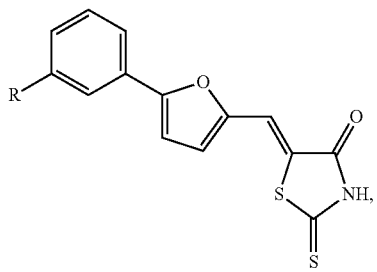

(IIID)

wherein R is F, Cl, Br, I, OMe, OH, NO$_2$, CF$_3$, or an isostere of these groups.

In some embodiments of the compound, it has a structure of formula (IV) or (V):

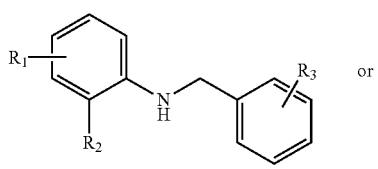

(IV)

or

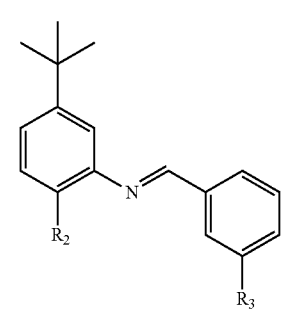

(V)

wherein:

R$_1$ is ortho, meta, or para to R$_2$ and is a hydrogen, C1-C6 group, hydroxyl group, alkoxy, halo, amino, alkylamino, thiol, alkylthio, sulfonyl, nitro, formyl, or carboxyl group, and R$_2$ is a hydroxyl, methoxy, ethoxy, halo, amino, alkylamino, thiol, alkylthio, sulfonyl, nitro, or carboxyl group; and R$_3$ is an ortho, meta, or para group and is a hydrogen, a C1-C6 group, hydroxyl, alkoxy, halo, amino, alkylamino, thiol, alkylthio, sulfonyl, nitro, or carboxyl group.

In some embodiments of the compound, it has a structure of the following formula

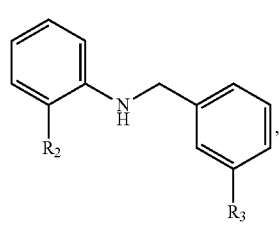

(IVA)

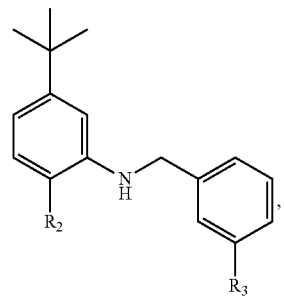

(IVB)

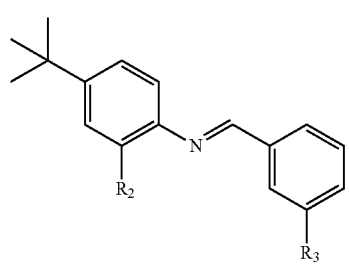

(VA)

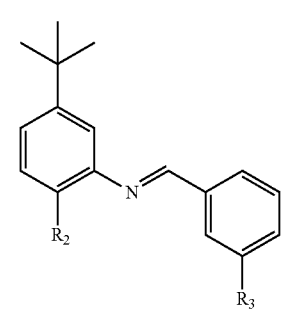

(VB)

wherein:

R$_2$ is a hydroxyl, methoxy, ethoxy, halo, amino, alkylamino, thiol, alkylthio, sulfonyl, nitro, or carboxyl group; and R$_3$ is an ortho, meta, or para group and is a hydrogen, a C1-C6 group, hydroxyl, alkoxy, halo, amino, alkylamino, thiol, alkylthio, sulfonyl, nitro, or carboxyl group.

In some embodiments of the compound, the compound comprises moiety (I) and moiety (II) and has a structure of

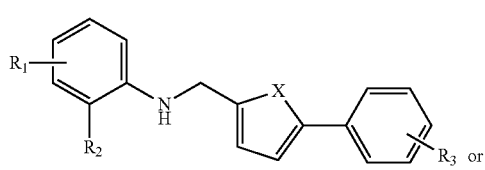

(VI)

or

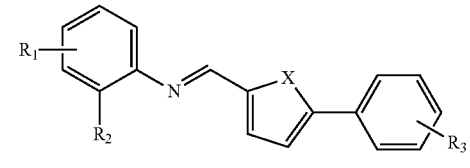

(VII)

wherein:

X is O or S;

R₁ is ortho, meta, or para to R₂ and is a hydrogen, C1-C6 group, hydroxyl group, alkoxy, halo, amino, alkylamino, thiol, alkylthio, sulfonyl, nitro, formyl, or carboxyl group;

R₂ is hydroxyl, methoxy, ethoxy, halo, alkylamino, amino, thiol, alkylthio, sulfonyl, nitro, or carboxyl group; and R₃ is ortho, meta, or para group and is a hydrogen, C1-C6 group, hydroxyl, alkoxy, halo, amino, alkylamino, thiol, alkylthio, sulfonyl, nitro, or carboxyl group.

In some embodiments of the compound, it has a structure of

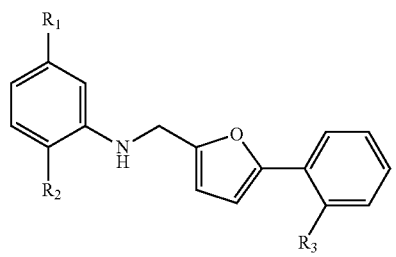

VIA or

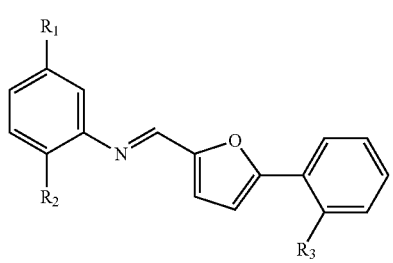

VIIA wherein:

R₁ is hydrogen or a C1-C6, hydroxyl group, alkoxy, halo, amino, alkylamino, thiol, alkylthio, sulfonyl, nitro, formyl, or carboxyl group, R₂ is a hydroxyl, methoxy, ethoxy, halo, amino, alkylamino, thiol, sulfonyl, alkylthio, nitro, or carboxyl group; and R₃ is ortho, meta, or para and is a hydrogen, C1-C6 group, hydroxyl, alkoxy, halo, amino, alkylamino, thiol, sulfonyl, alkylthio, nitro, or carboxyl group.

Some embodiments of compounds for formula (III) specifically exclude RTC13.

Some embodiments of compounds for formula (V) specifically exclude RTC14.

Some examples of the compounds are:

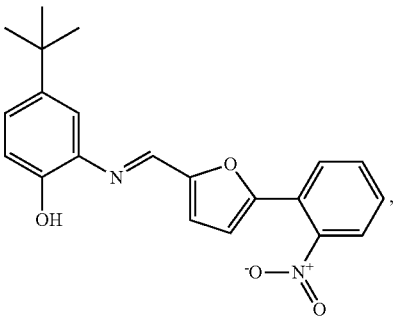

AZ1

4-tert-butyl-2-[[5-(2-nitrophenyl)-2-furyl]methyleneamino]phenol

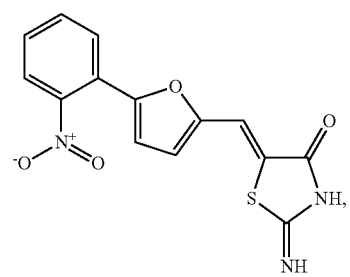

(5Z)-2-imino-5-[[5-(2-nitrophenyl)-2-furyl]methylene]thiazolidin-4-one

BC1:

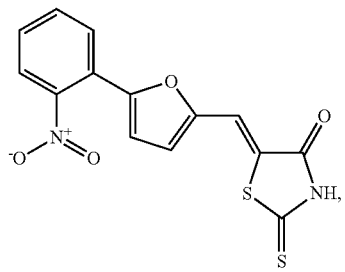

BC1

(5Z)-5-[[5-(2-nitrophenyl)-2-furyl]methylene]-2-thioxo-thiazolidin-4-one

BA3:

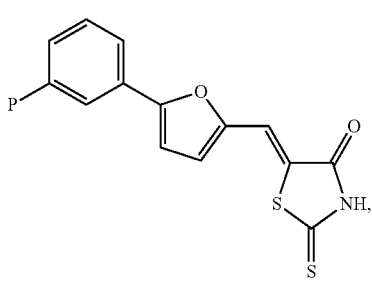

BA3

(5Z)-5-[[5-(3-fluorophenyl)-2-furyl]methylene]-2-imino-thiazolidin-4-one

-continued

BA5:

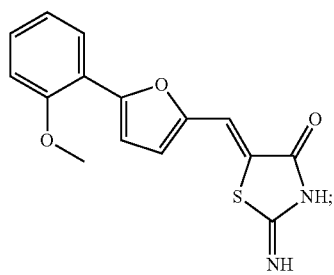

(5Z)-2-imino-5-[[5-(2-methoxyphenyl)-2-furyl]methylene]thiazolidin-4-one

Compound 14

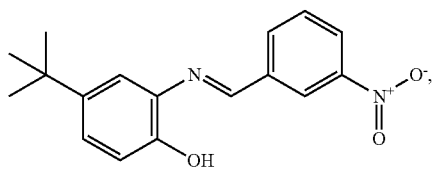

4-tert-butyl-2-[(3-nitrophenyl)methyleneamino]phenol

C1:

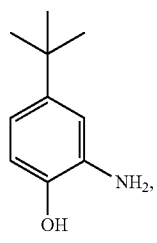

2-amino-4-tert-butyl-phenol

AD1:

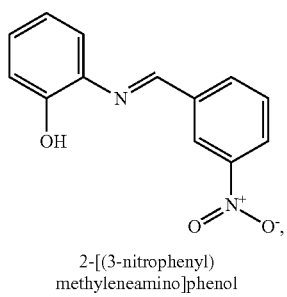

2-[(3-nitrophenyl)methyleneamino]phenol

AA1:

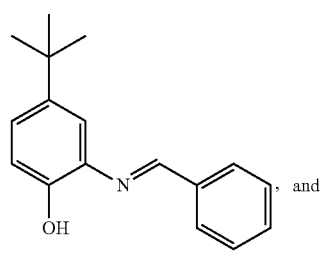

, and 2-(benzylideneamino)-4-tert-butyl-phenol

-continued

AB1:

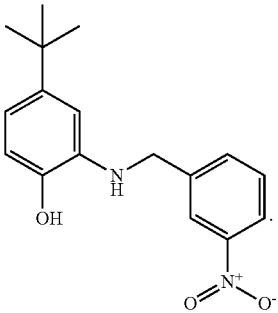

4-tert-butyl-2-[(3-nitrophenyl)methylamino]phenol

Some further examples of the compound are:

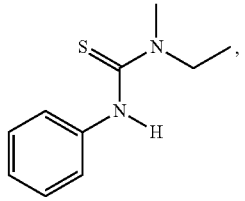

1-ethyl-1-methyl-3-phenyl-thiourea

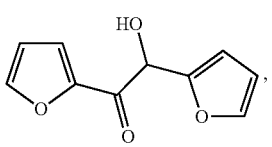

1,2-bis(2-furyl)-2-hydroxy-ethanone

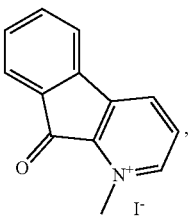

1-methylindeno[2,3-b]pyridin-1-ium-9-one iodide

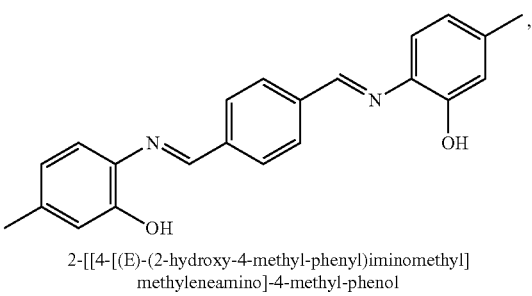

2-[[4-[(E)-(2-hydroxy-4-methyl-phenyl)iminomethyl]methyleneamino]-4-methyl-phenol

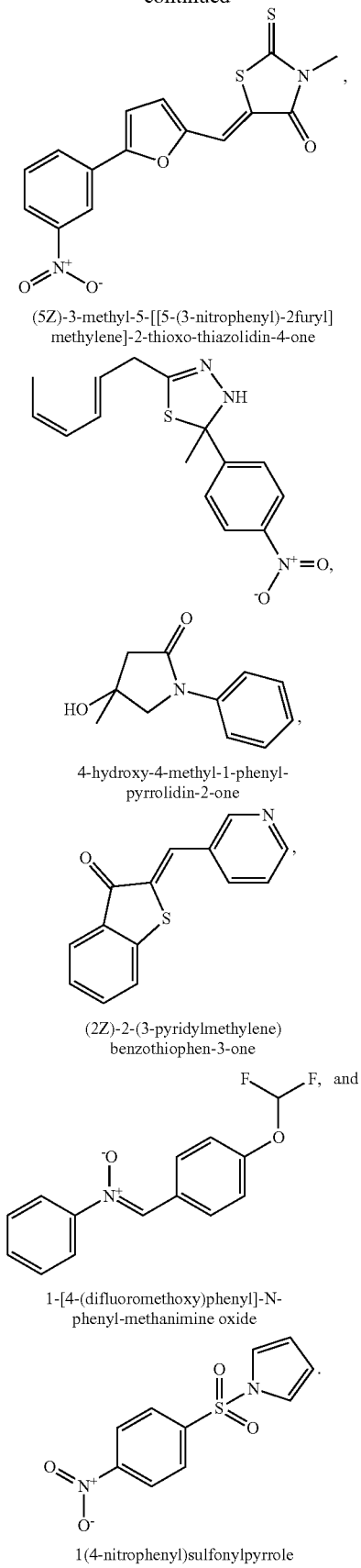

(5Z)-3-methyl-5-[[5-(3-nitrophenyl)-2furyl]methylene]-2-thioxo-thiazolidin-4-one 4-hydroxy-4-methyl-1-phenyl-pyrrolidin-2-one (2Z)-2-(3-pyridylmethylene)benzothiophen-3-one 1-[4-(difluoromethoxy)phenyl]-N-phenyl-methanimine oxide 1(4-nitrophenyl)sulfonylpyrrole In a further aspect of the present invention, it is provided a method of forming a compound having the ability to read through premature termination codons (PTCs) in RNA, comprising:

preparing an intermediate comprising moiety (I) and/or moiety (II):

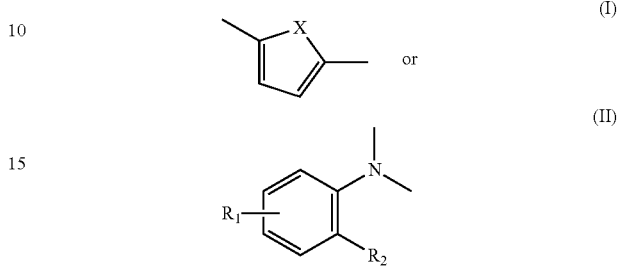

wherein
X is O or S;
R$_1$ is ortho, meta, or para to R$_2$ and is a hydrogen, C1-C6 group, hydroxyl group, alkoxy, halo, amino, alkylamino, thiol, alkylthio, sulfonyl, nitro, formyl, or carboxyl group, and
R$_2$ is a hydroxyl, methoxy, ethoxy, halo, amino, alkylamino, thiol, alkylthio, sulfonyl, nitro, or carboxyl group; and forming the compound.

In some embodiments of the method, the compound is as the compound described above or below.

In a further aspect of the present invention, it is provided a composition. The composition comprises at least one compound or a pharmaceutically acceptable salt or prodrug thereof in an amount effective for treating or ameliorating a medical condition associated with premature termination codons (PTCs) in RNA. The compound is described above or below.

In some embodiments of the composition, the composition comprises two compounds, each of the two compounds described above or below.

In some embodiments of the composition of invention, the composition further comprises a pharmaceutically acceptable carrier.

In some embodiments of the composition of invention, the composition is formulated in a formulation for local or systemic delivery. Examples of such formulations are formulations for oral administration, injection, topical administration, pulmonary administration, or implant.

In still a further aspect of the present invention, it is provided a method. The method comprises providing a compound having the ability to read through premature termination codons (PTCs) in RNA, and forming a composition comprising the compound, a pharmaceutically acceptable salt thereof, or a prodrug thereof. The compound is described above or below.

In some embodiments of the method, the composition comprises two compounds, each of the two compounds described above or below.

In some embodiments of the method of invention, the composition further comprises a pharmaceutically acceptable carrier.

In some embodiments of the method of invention, the composition is formulated in a formulation for local or systemic delivery. Examples of such formulations are formulations for oral administration, injection, topical administration, pulmonary administration, or implant.

In a further aspect of the present invention, it is provided a method of treating or ameliorating a medical condition associated with premature termination codons (PTCs) in RNA. The method comprises administering to a subject a compound described above or below or a composition described above or below.

BRIEF DESCRIPTION OF THE DRAWINGS

FIGS. 2a-2c show the identification of RTC13 and RTC14 as readthrough compounds by HTS.

DETAILED DESCRIPTION OF THE INVENTION

Figures 1A, 1B, 1C, 1D:
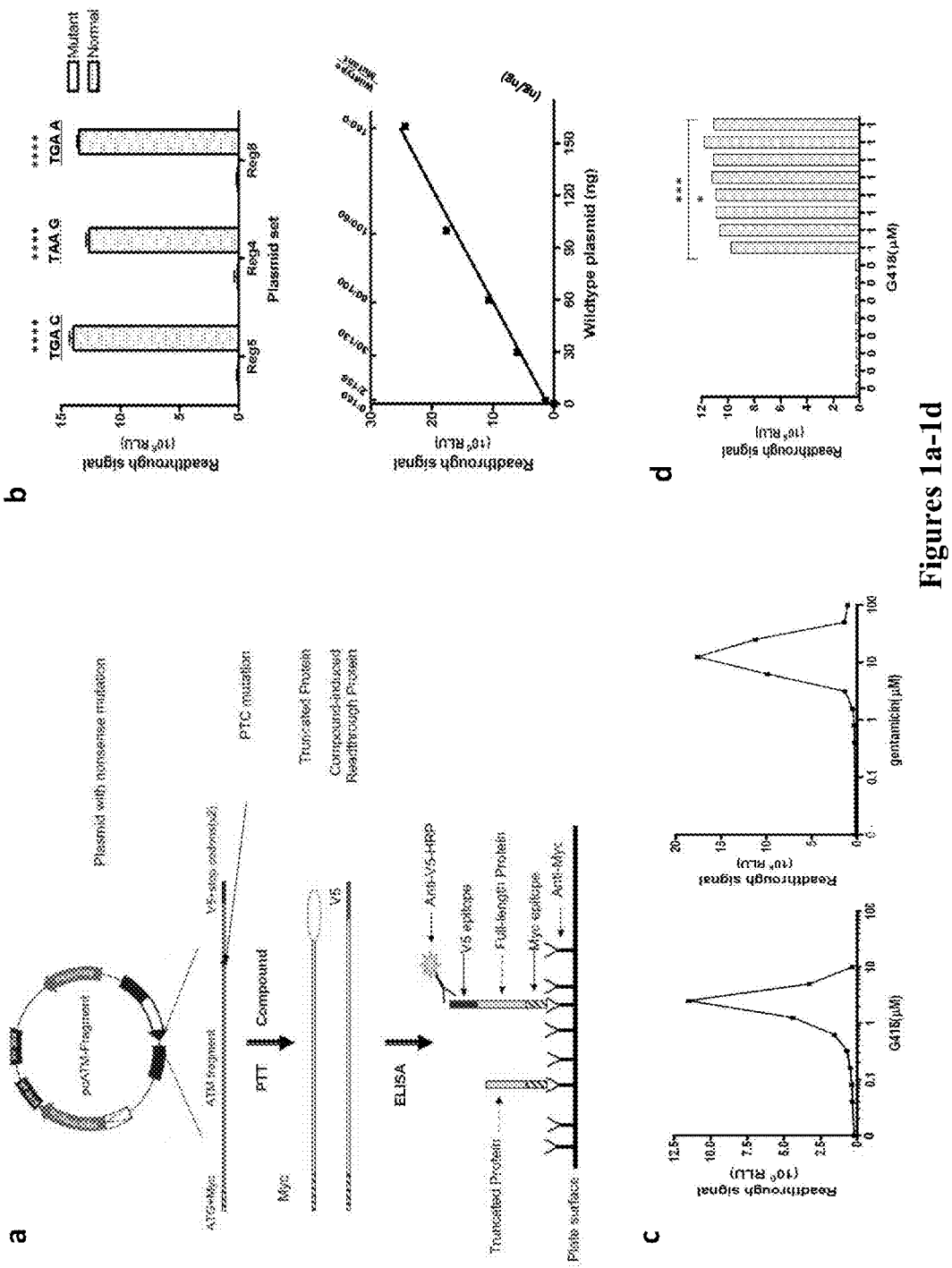
FIGS. 1a-1d illustrate the HTS PTT-ELISA assay of invention for RTCs screening.

In one aspect of the present invention, it is provided a system for high throughput assay for readthrough compound having the ability to read through premature termination codons (PTCs) in RNA. The system comprises high throughput reading trays and wells containing a plasmid, wherein the plasmid comprises a fragment of ATM gene that contains a PTC mutation, which fragment being flanked by a sequence that initiates transcription of: a) a myc epitope, b) the ATM fragment, and c) a V5 epitope;

wherein the assay is based on a coupled protein transcription/translation (PTT) reaction that is driven by the plasmid;

wherein the reading trays are coated with an antibody to the myc epitope; and wherein an antibody to V5 is provided for attaching to readthrough proteins expressing the V5 epitope.

In some embodiments of the system, the V5 epitope is conjugated to horseradish peroxidase.

In some further embodiments of the system, the system comprises a robot.

In another aspect of the present invention, it is provided a method of screen for readthrough compounds having the ability to read through premature termination codons (PTCs) in RNA. The method comprises:

providing a plasmid template to a reaction well having a test compound to cause a coupled protein transcription/translation (PTT) reaction to occur to generate a PTT reaction product, the plasmid template comprising a fragment of ATM gene that contains a PTC mutation, which fragment being flanked by a sequence that initiates transcription of: a) a myc epitope, b) the ATM fragment, and c) a V5 epitope;

adding the PTT reaction product to high throughput reading trays, which are coated with an antibody to the myc epitope to capture a protein fragment of the fragment of ATM gene, adding an antibody to the V5 epitope (V5 antibody) to wells in the reading trays, detecting the attachment of the V5 antibody to proteins in the PTT product, and identifying the test compound as a readthrough compound if the attachment of the V5 antibody to proteins in the PTT product occurs.

In some embodiments of the method, the V5 epitope is conjugated to horseradish peroxidase.

In some embodiments of the method, detecting is achieved by a chemiluminescence reaction as read out.

In a further embodiment of the present invention, it is provided a compound having the ability to read through premature termination codons (PTCs) in RNA, a pharmaceutically acceptable salt thereof or a prodrug thereof. The readthrough compound (sometimes referred to as "RTC" or "RT compound" hereafter) is effective for medical conditions associated with PTC.

In some embodiments, the RTC comprises a diradical moiety which is

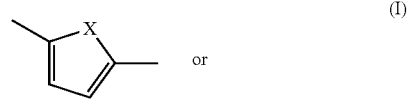

(I)

-continued

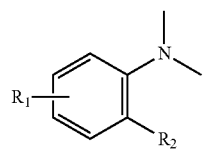
(II)

wherein:

in moiety (I), X is O or S;

in moiety (II):

$R_1$ is ortho, meta, or para to $R_2$ and is hydrogen or a C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, formyl, or carboxyl group, and $R_2$ is a hydroxyl, methoxy, ethoxy, halo (F, Cl, Br, or I), amino, alkylamino, thiol, alkylthio, sulfonyl, nitro, or carboxyl group.

Some embodiments of compounds comprising moiety (I) specifically exclude RTC13 (FIG. 2a), and some embodiments of compounds comprising moiety (II) specifically excludes RTC14 (FIG. 2a).

In some embodiments, the RTC compound comprising moiety (I) has a structure of

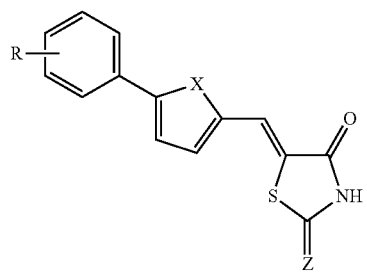
(III)

wherein:

X is O or S;

Z is O, S, or NR' in which R' is hydrogen or a C1-C6 group, e.g., methyl, ethyl, isopropyl, t-butyl, n-butyl, pentyl, n-hexyl, vinyl, or allyl; and R is an ortho, meta, or para group and is a hydrogen, C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, formyl, or carboxyl group.

Some embodiments of compounds for formula (III) specifically exclude RTC13.

A few embodiments of the compound of formula (III) are

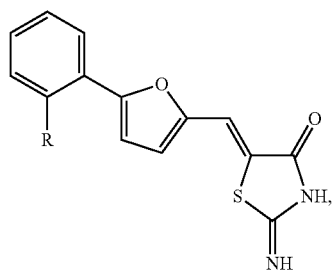
IIIA

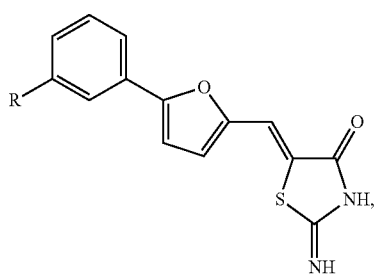
IIIB

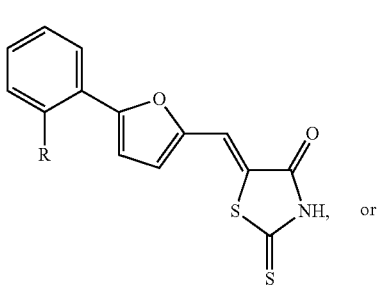
IIIC or

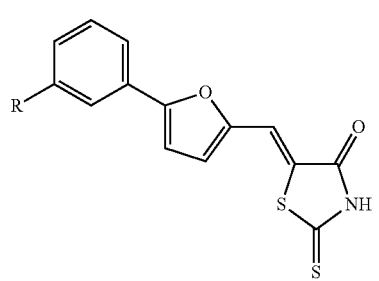
IIID wherein R is F, Cl, Br, I, OMe, OH, $NO_2$, $CF_3$, or an isostere of these groups.

As used herein, the term isosteres refer groups with the same number of atoms and the same number of valence electrons.

In some embodiments, the RTC compound comprising moiety (II) further comprises substituted benzyl moiety, which RTC compound preferably has a structure of

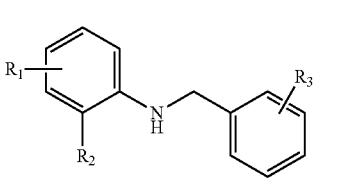
(IV)

or

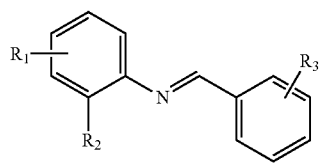
(V)

wherein:

R₁ is ortho, meta, or para to R₂ and is hydrogen or a C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, formyl, or carboxyl group, and R₂ is a hydroxyl, methoxy, ethoxy, halo (F, Cl, Br, or I), amino, alkylamino, thiol, alkylthio, sulfonyl, nitro, or carboxyl group; and R₃ is an ortho, meta, or para substituent and is a hydrogen, C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, or carboxyl group.

Some embodiments of compounds for formula (V) specifically exclude RTC14.

In some embodiments of the compound of formula (IV) or (V), the compound is any of IVA
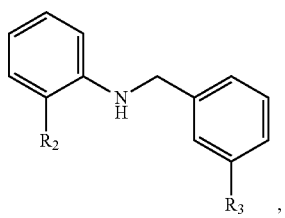

IVB
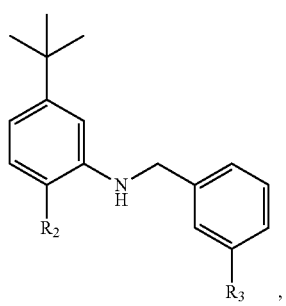

VA
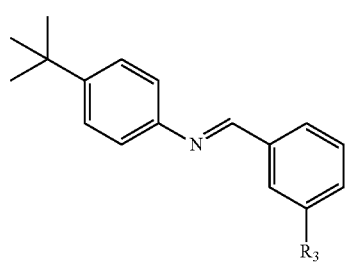

VB
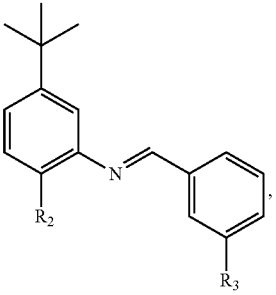

wherein:

R₂ is a hydroxyl, methoxy, ethoxy, halo (F, Cl, Br, or I), amino, alkylamino, thiol, alkylthio, sulfonyl, nitro, or carboxyl group; and R₃ is an ortho, meta, or para group and is a hydrogen, C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, or carboxyl group In some embodiments, the RTC compound comprises both the (I) and (II) moieties and has a structure of (VI)
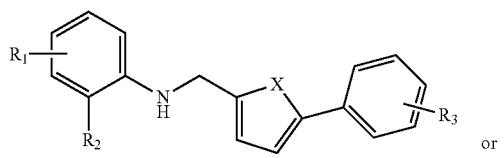

or (VII)
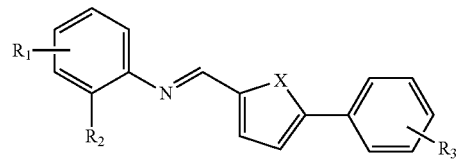

wherein:

X is O or S;

R₁ is ortho, meta, or para to R₂ and is hydrogen or a C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, formyl, or carboxyl group, and R₂ is a hydroxyl, methoxy, ethoxy, halo (F, Cl, Br, or I), amino, alkylamino, thiol, alkylthio, sulfonyl, nitro, or carboxyl group; and R₃ is an ortho, meta, or para group and is a hydrogen, C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, or carboxyl group.

In some embodiments, the compound comprising both moiety (I) and moiety (II) has a structure of

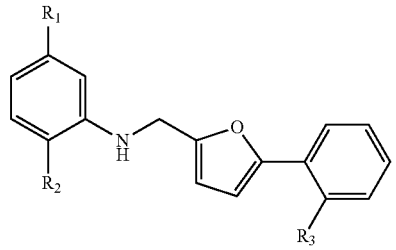

VIA or

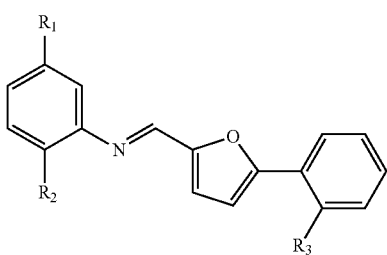

VIIA wherein:

R₁ is hydrogen or a C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, formyl, or carboxyl group, and R₂ is a hydroxyl, methoxy, ethoxy, halo (F, Cl, Br, or I), amino, alkylamino, thiol, alkylthio, sulfonyl, nitro, or carboxyl group; and R₃ is an ortho, meta, or para group and is a hydrogen, C1-C6 group, such as methyl, ethyl, propyl, isopropyl, n-butyl, 2-butyl, tert-butyl, n-pentyl, 2-pentyl, vinyl, allyl, n-hexyl, and phenyl, hydroxyl group, alkoxy, such as methoxy, or ethoxy, halo (F, Cl, Br, or I), amino, alkylamino, thiol, alkylthio, sulfonyl, nitro, or carboxyl group.

An example of the compound of formula VII is AZ1:

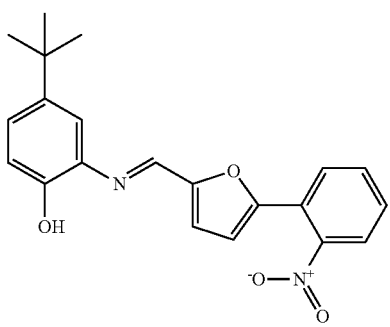

AZ1

4-tert-butyl-2-[[5-(2-nitrophenyl)-2-furyl]methylene-amino]phenol

Some examples of the readthrough compounds disclosed herein comprising the moiety (I) and/or moiety (II) are listed below:

Compound 13

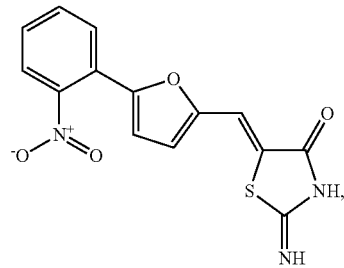

(5Z)-2-imino-5-[[5-(2-nitrophenyl)-2-furyl]methylene]thiazolidin-4-one

BC1

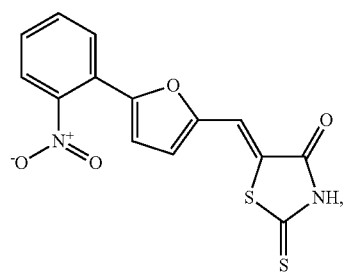

(5Z)-5-[[5-(2-nitrophenyl)-2-furyl]methylene]-2-thioxo-thiazolidin-4-one

BA3

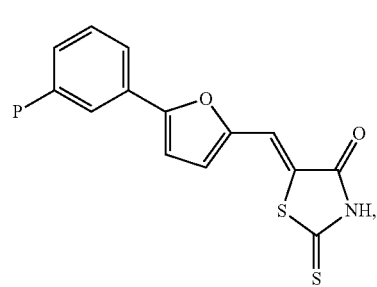

(5Z)-5-[[5-(3-fluorophenyl)-2-furyl]methylene]-2-imino-thiazolidin-4-one

BA5

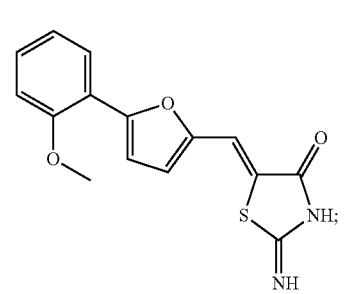

(5Z)-2-imino-5-[[5-(2-methoxyphenyl)-2-furyl]methylene]thiazolidin-4-one

Compound 14

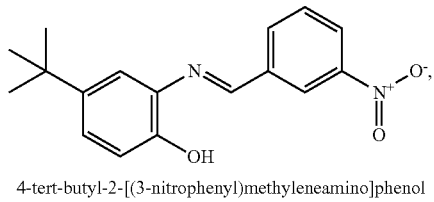

4-tert-butyl-2-[(3-nitrophenyl)methyleneamino]phenol

C1:

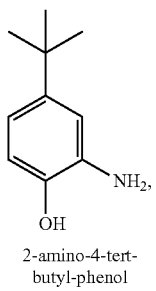

2-amino-4-tert-butyl-phenol

AD1:

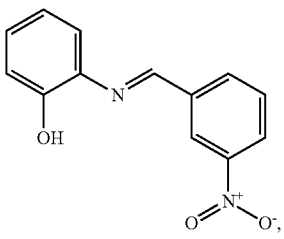

2-[(3-nitrophenyl)methyleneamino]phenol

AA1:

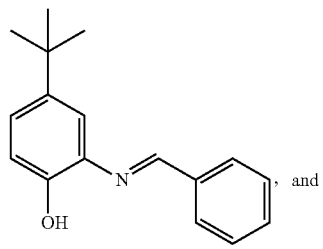

2-(benzylideneamino)-4-tert-butyl-phenol

AB1:

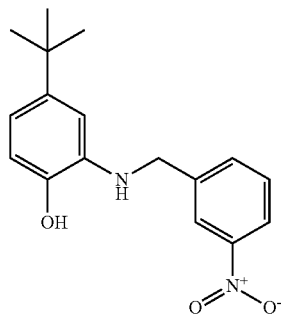

4-tert-butyl-2-[(3-nitrophenyl)methylamino]phenol

In some further embodiments, the RTC is selected from the group consisting of

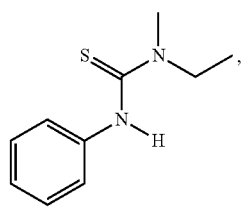

1-ethyl-1-methyl-3-phenyl-thiourea

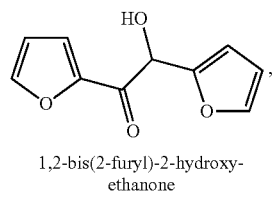

1,2-bis(2-furyl)-2-hydroxy-ethanone

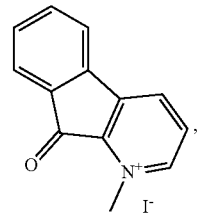

1-methylindeno[2,3-b]pyridin-1-ium-9-one iodide

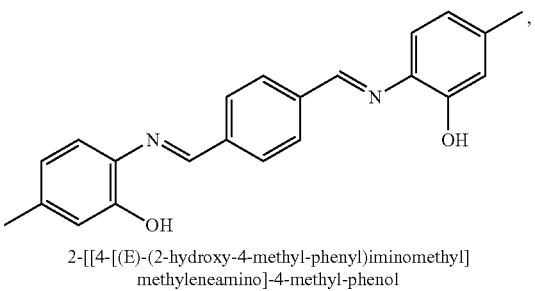

2-[[4-[(E)-(2-hydroxy-4-methyl-phenyl)iminomethyl]methyleneamino]-4-methyl-phenol -continued

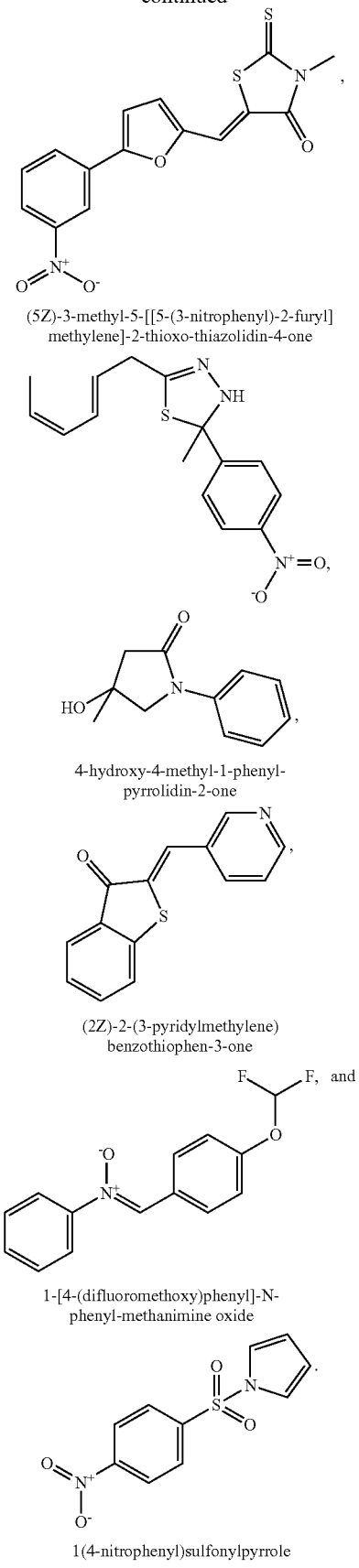

(5Z)-3-methyl-5-[[5-(3-nitrophenyl)-2-furyl]methylene]-2-thioxo-thiazolidin-4-one 4-hydroxy-4-methyl-1-phenyl-pyrrolidin-2-one (2Z)-2-(3-pyridylmethylene)benzothiophen-3-one 1-[4-(difluoromethoxy)phenyl]-N-phenyl-methanimine oxide 1(4-nitrophenyl)sulfonylpyrrole The various embodiments of RCT compound of invention include a pharmaceutically acceptable salts or prodrugs thereof. As used herein, the term "prodrug" shall mean a precursor (forerunner) of a drug. A prodrug must undergo chemical conversion by metabolic processes before becoming an active pharmacological agent.

In some embodiments, the compounds can be used with other compounds, or can be used as a composition of two or more compounds selected therefrom.

In a further aspect of the present invention, it is provided a method of forming a compound having the ability to read through premature termination codons (PTCs) in RNA, comprising:

preparing an intermediate comprising moiety (I) and/or moiety (II):

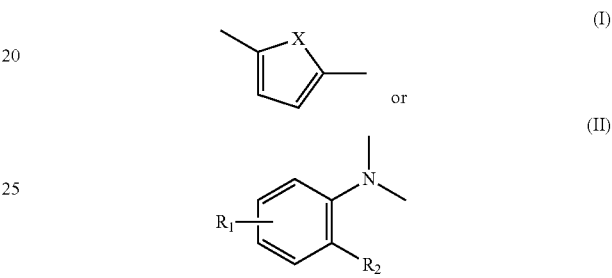

wherein

X is O or S;

R$_1$ is ortho, meta, or para to R$_2$ and is a hydrogen, C1-C6 group, hydroxyl, alkoxy, halo, amino, alkylamino, thiol, alkylthio, sulfonyl, nitro, formyl, or carboxyl group, and R$_2$ is a hydroxyl, methoxy, ethoxy, halo, amino, alkylamino, thiol, alkylthio, sulfonyl, nitro, or carboxyl group; and forming the compound.

In some embodiments of the method, the compound is as the compound described above or below.

In a further aspect of the present invention, it is provided a composition. The composition comprises at least one compound or a pharmaceutically acceptable salt or prodrug thereof in an amount effective for treating or ameliorating a medical condition associated with premature termination codons (PTCs) in RNA. The compound is described above or below.

In some embodiments of the composition, the composition comprises two compounds, each of the two compounds described above or below.

In some embodiments of the composition of invention, the composition further comprises a pharmaceutically acceptable carrier.

In some embodiments of the composition of invention, the composition is formulated in a formulation for local or systemic delivery. Examples of such formulations are formulations for oral administration, injection, topical administration, pulmonary administration, or implant.

In still a further aspect of the present invention, it is provided a method. The method comprises providing a compound having the ability to read through premature termination codons (PTCs) in RNA, and forming a composition comprising the compound, a pharmaceutically acceptable salt thereof, or a prodrug thereof. The compound is described above or below.

In some embodiments of the method, the composition comprises two compounds, each of the two compounds described above or below.

In some embodiments of the method of invention, the composition further comprises a pharmaceutically acceptable carrier.

In some embodiments of the method of invention, the composition is formulated in a formulation for local or systemic delivery. Examples of such formulations are formulations for oral administration, injection, topical administration, pulmonary administration, or implant.

In a further aspect of the present invention, it is provided a method of treating or ameliorating a medical condition a medical condition associated with premature termination codons (PTCs) in RNA. The method comprises administering to a subject a compound described above or below or a composition described above or below.

Method of Making

A compound disclosed can be readily prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Synthesis of the compound is exemplified in Examples where the preparation of more than 41 different compounds is described in detail.

Methods of Use

In a further aspect, it is provided a method of using the RTC. The method comprises applying the RTC to a subject an RTC of invention to treat, prevent, or ameliorate a medical condition. The medical condition can be any disease or disorder caused by or otherwise associated with PTC.

In some embodiments, the method can be conducted in living bodies of mammals. In such a case, the compounds may be administered to the mammals. In one embodiment of the present invention, the mammals may be patients with genetic diseases caused by nonsense mutation, and the method may be conducted as a treatment method of genetic diseases caused by nonsense mutation.

As used herein, the term disorder and medical condition can be used interchangeably and generally refer to a disease attributable to an internal termination codon in a gene (a premature termination codon) generated by such as a point mutation, deletion, and insertion in the gene which leads to inhibition of expression of protein having a normal function, or attributable to degradation of mRNA that contains the premature termination codon which leads to inhibition of protein expression. The genetic disease caused by nonsense mutation is not specifically limited, but is exemplified by the following: central nervous system diseases such as muscular dystrophy, Duchenne muscular dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis and graft-versus-host disease; inflammatory diseases such as arthritis; blood diseases such as hemophilia, von Willebrand disease, ataxia telangiectasia, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesterolemia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; and cancer. The term "cancer", such as cancer associated with a nonsense mutation of a suppressor gene such as p53 gene, includes all types of cancer, which is exemplified by lung cancer, colon and rectal cancer, stomach cancer, esophagus cancer, kidney cancer, pancreatic cancer, prostate cancer, breast cancer, uterus cancer, ovary cancer, skin cancer and brain tumor.

Pharmaceutical Compositions

In another aspect of the present invention, a pharmaceutical composition for use in treatment or prevention of the genetic diseases caused by nonsense mutation is provided, wherein the pharmaceutical composition comprises as an effective ingredient a compound expressed by any one of the aforementioned formulae a pharmacologically acceptable salt or prodrug thereof.

The pharmaceutical composition preferably comprises a compound described above or a pharmacologically acceptable salt or prodrug thereof.

The pharmaceutical composition more preferably comprises a compound shown in the aforementioned table.

In the aforementioned aspect of the present invention, the pharmaceutical composition may contain a pharmacologically acceptable carrier or excipients. An amount of the compound used in the pharmaceutical composition is not limited as far as it is an effective amount for treatment. The genetic disease caused by nonsense mutation is not specifically limited, but is exemplified by the following: central nervous system diseases such as muscular dystrophy, Duchenne muscular dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis and graft-versus-host disease; inflammatory diseases such as arthritis; blood diseases such as hemophilia, von Willebrand disease, ataxia telangiectasia, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesterolemia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; and cancer. The term "cancer", such as cancer associated with a nonsense mutation of a suppressor gene such as p53 gene, includes all types of cancer, which is exemplified by lung cancer, colon and rectal cancer, stomach cancer, esophagus cancer, kidney cancer, pancreatic cancer, prostate cancer, breast cancer, uterus cancer, ovary cancer, skin cancer and brain tumor.

The pharmaceutical composition in the aspect of the present invention may contain, as active ingredients, the aforementioned compound and other compounds, or may contain a mixture of two or more aforementioned compounds.

The pharmacologically acceptable salt in the present specification is not specifically limited as far as it can be used in medicaments. Examples of a salt that the compound of the present invention forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Further, the compounds of the present invention include hydrates thereof, various pharmaceutically acceptable solvates thereof, and polymorphic crystals thereof.

The pharmaceutical compositions of the present invention can be formulated in various dosage forms, which are exemplified by the following: oral administration forms such as tablets, capsules, powders, granules, pills, liquids, emulsions, suspensions, solutions, spirits, syrups, extracts, and elixirs; parenteral administration forms such as injections, for example, subcutaneous injections, intravenous injections, intramuscular injections, and intraperitoneal injections; transdermal administration forms, plasters and pressure sensitive adhesives, ointments or lotions; intramouth administration forms such as sublingual forms and oral patch preparations; and nasal administration forms such as aerosols, but are not limited thereto. These preparations can be manufactured by using a known method generally used in a drug manufacturing process. In one embodiment of the present invention, the pharmaceutical composition of the present invention may be administered for treating muscular disease as an injection such as an intramuscular injection for administering directly into muscle.

The pharmaceutical compositions may contain various kind of ingredients generally used, for example, one or more pharmaceutically acceptable fillers, disintegrators, diluents, lubricants, flavoring agents, colorants, sweetening agents, corrigents, suspending agents, humectants, emulsifying agents, dispersing agents, auxiliary agents, preservatives, buffers, binders, stabilizers, and coating agents. In addition, the pharmaceutical composition of the present invention may be sustained-release dosage forms or extended-release dosage forms.

Dosage ranges of the pharmaceutical compositions are not particularly limited, and can be determined in accordance with the following: effectiveness of the ingredients contained therein; the administration form; the route of administration; the type of disease; the characteristics of the subject (e.g., body weight, age, symptomatic conditions, and whether a subject is taking other pharmaceutical agents); and the judgment of a physician in charge. In general, a suitable dosage may fall, for example, within a range of about 0.01 μg to 100 mg, per 1 kg of the body weight of the subject, and preferably within a range of about 0.1 μg to 1 mg, per 1 kg of body weight. However, the dosage may be altered using conventional experiments for optimization of a dosage that are well known in the art. The aforementioned dosage can be divided for administration once to several times a day. Alternatively, periodic administration once every few days or few weeks can be employed.

The pharmaceutical compositions may be administered to a patient whose biological sample obtained in advance is subjected to a study for presence or absence of premature termination codons in genes contained therein and is found to have a detected premature termination codon. A biological sample may be any ones insofar as it contains nucleic acids, and is exemplified by cells, bloods, cerebrospinal fluids, bronchioalveolar lavage fluids, expectorants, or other body fluids as well as biopsy tissues. Nucleic acid samples can be prepared from the biological samples for use. The nucleic acid samples can be prepared by well known nucleic acid preparation methods. The nucleic acid samples may be DNA or RNA. The nucleic acid samples prepared may be used directly for detection, or may be subjected to enzymatic amplification of predetermined region thereof by PCR or other amplification methods in advance for analysis. Detection of a termination codon can be carried out by using well known methods for detecting genetic mutations such as DNA sequencing, Southern blot, polymerase chain reaction (PCR), short tandem repeat (STR), or restricted fragment length polymorphism. The detection method is not limited to the exemplified methods, and any method can be used insofar as it can detect a premature termination codon. Alternatively, the presence of a premature termination codon can be detected by measuring an amount of mRNA derived from the predetermined gene in the biological sample and detecting reduction of the amount of the mRNA compared to an amount of mRNA derived from the gene in a biological sample obtained from healthy subject. mRNA can be measures by using known analysis methods such as northern blotting.

In terms of a route of administration of the pharmaceutical composition, it may be either systemic administration or local administration. The route of administration that is appropriate for a particular disease, symptomatic condition, or other factors, should be selected. For example, parenteral administration including normal intravenous injection, intra-arterial administration, subcutaneous administration, intracutaneous administration, and intramuscular administration can be employed. Oral administration can be also employed. Further, transmucosal administration or transdermal administration can be employed.

The term "read-through" herein means to skip over a premature termination codon in ribosomal translation, or to substitute an amino acid, or to suppress degradation of mRNA that comprises a premature termination codon.

In the aforementioned aspect of the present invention, a sequence that comprises a premature termination codon derive from responsible genes for diseases caused by nonsense mutation is not specifically limited insofar as it is a sequence comprising a termination codon such as TAA, TAG, or TGA, in a reading flame. The sequence is preferably around 20 to 150 by long. In one embodiment, the sequence may be a sequence containing a sequence that comprises a premature termination codon of humans or animals having genetic disease caused by nonsense mutation including animal models for the diseases. For example, such a gene can contain a premature termination codon in the dystrophin gene of mdx mice.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However, the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch, or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semil-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention is described in more detail in the following illustrative examples. Although the examples can represent only selected embodiments of the invention, it should be understood that the following examples are illustrative and not limiting.

EXAMPLES

General Procedures

The various assays described in this section are applicable to all the assays performed in the following examples High Throughput Assay We have developed a high throughput assay that identifies compounds with the ability to read through premature termination codons (PTC) in RNA. The assay is based on a coupled protein transcription/translation (PTT) reaction that is driven by a plasmid template (to supply the RNA for the PTT reaction). The plasmid includes a fragment of the ATM gene that contains a PTC mutation, flanked by sequence that initiates transcription of i) a myc epitope, ii) the ATM sequence, and iii) a V5 epitope. Using a robot, the high throughput reading trays are first coated with antibody to the myc epitope, in order to capture the Atm protein fragment when the PTT product is added. The PTT reaction product is then added. If the compound being tested has read through the mutation, the V5 epitope will also be translated. When an antibody to V5, conjugated with horseradish peroxidase, is added to the wells, it will attach only to readthrough proteins. This will be detected by a chemiluminescence reaction as a read out.

FIGS. 1a and 1b show the general procedure of performing a readthrough assay of the compounds of invention. FIGS. 1c and 1d show the results of readthrough assay using G418 and gentamicin following the afore-described procedures of readthrough assay.

The high throughput assay is described in detail in Du, L. et al., *J. Experimental Med.* 2009, 206, 2285-2297. The teaching in this reference is incorporated herein in its entirety by reference.

For consistency purposes, the compounds tested in the examples are cross-referenced in Table 1 below, where the positive results on various assays are also summarized and labeled as "+". Structures and/or chemical names of these compounds are described in Example 5, below.

TABLE 1

| Compound ID | Also referred to as | PTT-ELISA | FCATMs1981 | IRIF (ATMs1981) | FCSMC966 | CSA | ATM-ELISA |
|---|---|---|---|---|---|---|---|
| RTC13 | 1 | + | + | + | + | + | + |
| RTC14 | 2 | + | + | + | + | + | + |
| BA1 | 7a | + | | | | | |
| BA3 | 7j | + | | | | | |
| BA4 | 7d | + | | | | | |
| BA5 | 7e | + | | | | | |
| BA6 | 7f | + | | | | | |
| BC3 | 7q | + | + | | | | |
| BC6 | 7m | + | + | | | | |
| BC7 | 7n | + | + | | | | |
| BC8 | 7o | | + | | | | |
| BC9 | 7p | | + | | | | |
| BA8 | 7h | | + | | | | |
| BA9 | 7i | | + | | | | |
| BB1 | | + | | | | | |
| BC1 | 7b | + | | | | | |
| BZ1 | | + | | | | | |
| C3 | | + | | | | | |
| C4 | | + | | | | | |
| BZ6 | 13k | | + | + | | | |
| BZ9 | 9g | | + | | | | |
| BZ16 | 13a | | + | | | | |
| BZ17 | 13b | | + | | | | |
| BZ21 | 13i | | + | | | | |
| BZ22 | 13g | | + | | | | |

TABLE 1-continued

| Compound ID | Also referred to as | PTT-ELISA | FCATMs1981 | IRIF (ATMs1981) | FCSMC966 | CSA | ATM-ELISA |
|---|---|---|---|---|---|---|---|
| BZ23 | 13h | + | | + | | | |
| BZ24 | 13e | + | | + | | | |
| BZ25 | 13f | + | | + | | | |
| BZ26 | 13d | + | | + | | | |
| BZ27 | 13j | + | | + | | | |

Example 1

Studies on RTC13 and RTC14 as Readthrough Compounds by High Throughput PTT-ELISA Readthrough Assays In an effort to discover new RTCs, we developed a sensitive and quantitative luciferase-independent FITS assay, protein transcription/translation (PTT)-ELISA. The PTT-ELISA assay was validated for a fully automated 384-well robotic platform and used to screen ~34,000 compounds. We identified two compounds that induced low levels of full-length functional A-T mutated (ATM) protein in A-T cells carrying ATM nonsense mutations, as demonstrated by direct measurement of ATM protein using ATM-ELISA, ATM-Ser1981 autophosphorylation, trans-phosphorylation of structural maintenance of chromosome (SMC) 1-Ser966, and colony survival assay (CSA). Both compounds also showed PTC-readthrough activity in inch mouse myotube cells carrying a nonsense mutation and induced significant amounts of dystrophin protein.

Collectively, these studies provide the first robust luciferase-independent HTS assay for identifying RTCs and proof of principle for PTC readthrough by nonaminoglycoside compounds. They further establish that enhanced PTC readthrough can be considered as a therapeutic strategy for correcting nonsense mutations in many genetic diseases.

Development and Validation of HTS Assay PTT-ELISA

In vitro PTT was originally designed to detect truncating mutations (Roest et al., 1993, *Hum. Mol. Genet.* 2:1719-1721; Telatar et al., 1996, *Am. J. Hum. Genet.* 59:40-44). ELISA was coupled into PTT to improve throughput for the detection of these mutations (Gite et al., 2003, *Nat. Biotechnol.* 21:194-197; L. Du et al., 2008, *Mutat. Res.* 640:139-144). In a previous study, we used a PTT-PAGE gel approach to evaluate various aminoglycosides for readthrough activity of ATM nonsense mutations (Lai et al., 2004). However, the gel-based PTT assay was time consuming and involved the use of radioactive material; thus, it was difficult to automate for a high-throughput format. Herein, we have developed a plasmid-driven PTT-ELISA assay for screening large numbers of compounds for PTC readthrough activity. The assay uses plasmid templates containing prototypic ATM mutations, patterned after specific disease-causing ATM mutations. So as to work in a mammalian system, rabbit reticulocytes were chosen to drive the PTT reaction. Various fragments of mutated ATM alleles from cells of A-T patients were cloned into the plasmids and were N- and C-terminally tagged with the epitopes myc and V5, respectively. Anti-myc antibody was used to capture the translated protein onto an ELISA plate. If compounds induce PTC-readthrough in the assay, the plasmid-driven PTT results in a full-length ATM fragment including the V5 tag, which is detected with anti-V5-horseradish peroxidase (HRP) antibody (FIG. 1a).

FIGS. 1a-1d illustrate an embodiment of the HTS PTT-ELISA assay for RTCs screening. (a) Schematic of PTT-ELISA HTS. ATM regions containing a PTC mutation were cloned into plasmids and tagged with c-myc and V5 epitopes at each end. Compounds with PTC readthrough activity induce full-length protein, which can be identified by anti-V5-HRP. (b) Specificity and sensitivity of PTT-ELISA. All three mutant plasmids showed only background readings, whereas wild-type plasmids showed signals >200-fold over background (P<0.0001), indicating that the assay specifically detects full-length proteins. The sample containing 2 ng of wild-type plasmid still gave signals that were twofold higher than those of mutant plasmid alone (P<0.01), indicating that the sensitivity of the assay is ~1% (2/158 ng). Error bars indicate the variation of duplicate samples. (c) Assay evaluation using aminoglycosides. Both G418 and gentamicin induced significant PTC readthrough over a large dose range. (d) Readings for a sample row from a 384-well plate. Samples containing G418 exhibited significantly different signal (Z' factor >0.6) over the no-drug wells (P<0.0001). ****, P<0.0001, as compared with control. Experiments were repeated three times for b and c and five times for d.

We constructed three mutant plasmids that contain prototypic PTC mutations in the ATM gene from three different A-T patients. The plasmid used for preliminary screening, plasmid-TAT51, contains ATM region 5 fragment (codons 1403-1886) and harbors a nonsense (PTC) mutation (c.5623C→T) that leads to a TGA C stop codon. The second mutant plasmid, plasmid-AT153LA, contains the same TGA stop codon but at a different position within the gene (c.8977C→T) in region 8 (codons 2550-3050) and also has a different+4 nt (TGA A). This was used to monitor the effect of surrounding sequences of PTCs on readthrough ability. A third mutant plasmid, plasmid-AT185LA, contains a different stop codon, TAA G, resulting from a nonsense mutation (c.3673C→T) in region 4 (codons 1041-1531). Plasmids containing the same fragments but without mutations were constructed by in vitro mutagenesis of patient-derived complementary DNA and were used as wild-type controls.

We first evaluated the specificity and sensitivity of PTT-ELISA to detect the in vitro-translated full-length protein fragment. All three mutant plasmids gave only background signal, whereas the comparable wild-type plasmids showed signals greater than ~200-fold over background (FIG. 1b, top), indicating that the assay specifically recognized full-length protein fragments. We next used TAT51 wild-type plasmid to evaluate the sensitivity of the assay. The TAT51 wild-type plasmid was serially diluted with TAT51 mutant plasmid and used to drive PTT reactions. The sample containing 1.2% of wild-type plasmid (2/158 ng) still gave signal that was twofold higher than that of mutant plasmid (FIG. 1b, bottom), establishing the sensitivity of the assay at ~1%. The sensitivity of an HTS assay is especially important for RTC screening because all RTCs to date have been only weak PTC readthrough inducers, and new classes of RTCs are expected only to be identified with a highly sensitive screening assay.

Next, we used two well known RTCs, G418 and gentamicin, to test the efficiency of the PTT-ELISA assay. Both compounds showed significant PTC readthrough activity with TAT51 mutant plasmid (TGA C) over a large dose range (40 nM-10 μM; FIG. 1c). Moreover, G418 showed obvious toxicity for the PTT reaction at concentrations >2.5 μM, whereas gentamicin toxicity was not observed until 12.5 μM. These results are consistent with our previously published $S^{35}$-PTT gel data (Lai et al., 2004) and demonstrate that the PTT-ELISA readily identifies compounds with readthrough activity.

We next validated the assay for use in a fully automated 384-well robotic platform, using plasmid-TAT51 (TGA C) as readthrough template and 1 μM G418 as the positive readthrough control. To further reduce the cost of the assay, we optimized a decrease in the PTT reaction volume from 25 to 5 μl. As shown in FIG. 1d, the wells containing 6418 exhibited significantly different signals (Z' factor >0.8) over the no-drug wells. The fully automated assay also showed consistent plate-to-plate accuracy and efficiency, indicating the suitability of the assay for HTS (unpublished data).

Screening of Chemical Libraries for RTCs

About 34,000 compounds were screened to discover novel RTCs. Plasmid-TAT51 (TGA C) was used for the initial screening. Each compound was screened at a final concentration of 10 μM in the assay mixture. For each screening plate, we included both positive (with 1 μM G418) and negative (with DMSO) samples as quality controls. Samples with signal >2-fold over the negative control were scored as potential "hits." Our initial screens yielded 12 low-molecular-mass RTCs with appreciable readthrough activity. All 12 hits were then confirmed by manual PTT-ELISA at multiple concentrations. None of them were aminoglycosides and none of them had been previously reported. The chemical names and structures of the two leading compounds, RTC#13 and #14, are described above.

FIGS. 2a-2c show the identification of RTC13 and RTC14 as readthrough compounds by HTS. (a) Molecular structures of RTC#13 and #14 (2-imino-5-{[5-(2-nitrophenyl)-2-furyl]methylene}-1,3-thiazolidin-4-one and 4-tert-butyl-2-[(3-nitrobenzylidene)amino]pheno). (b) TGA C readthrough activity by PTT-ELISA. (c) TGA A and TAA G readthrough activity. , $P<0.01$; *, $P<0.001$, as compared with untreated control. Experiments were repeated four times for b and three times for c.

The $EC_{50}$ of five compounds (RTC#4, #11, #13, #14, and #16) were <10 μM (FIG. 2b, RTC#13 and #14), implying therapeutic potential of those compounds. Notably, in these initial cell-free experiments, the maximum in vitro readthrough effect for the new compounds was not as favorable as that of G41.8 or gentamicin. For example, the maximum readthrough activity of RTC#13 and #14, detected by the cell-free PTT-ELISA assay, was ~10% of the maximum activity of G418 and gentamicin in the same assay (FIG. 1c vs. FIG. 2b). This may be associated with the solubility, permeability, or toxicity of the compounds. In contrast, both RTC#13 and #14 had an $EC_{50}$<10 μM, they were less toxic, and they did not show obvious inhibition of PTT at high concentrations (>50 μM), unlike both G418 and gentamicin (FIG. 1c).

The readthrough efficiency of these compounds was also tested on two other stop codon contexts, TGA A and TAA G. For TGA A, all 12 compounds showed various extents of readthrough activity (unpublished data). For TAA G, six compounds (RTC#10, #11, #13, #14, #16, and #17) showed appreciable activity (unpublished data). The data for RTC#13 and #14 are shown in FIG. 2c.

RTC-Induced ATM Protein and ATM-Ser1981 Phosphorylation in A-T Lymphoblastoid Cell Lines (LCLs)

Figures 3A, 3B, 3C:
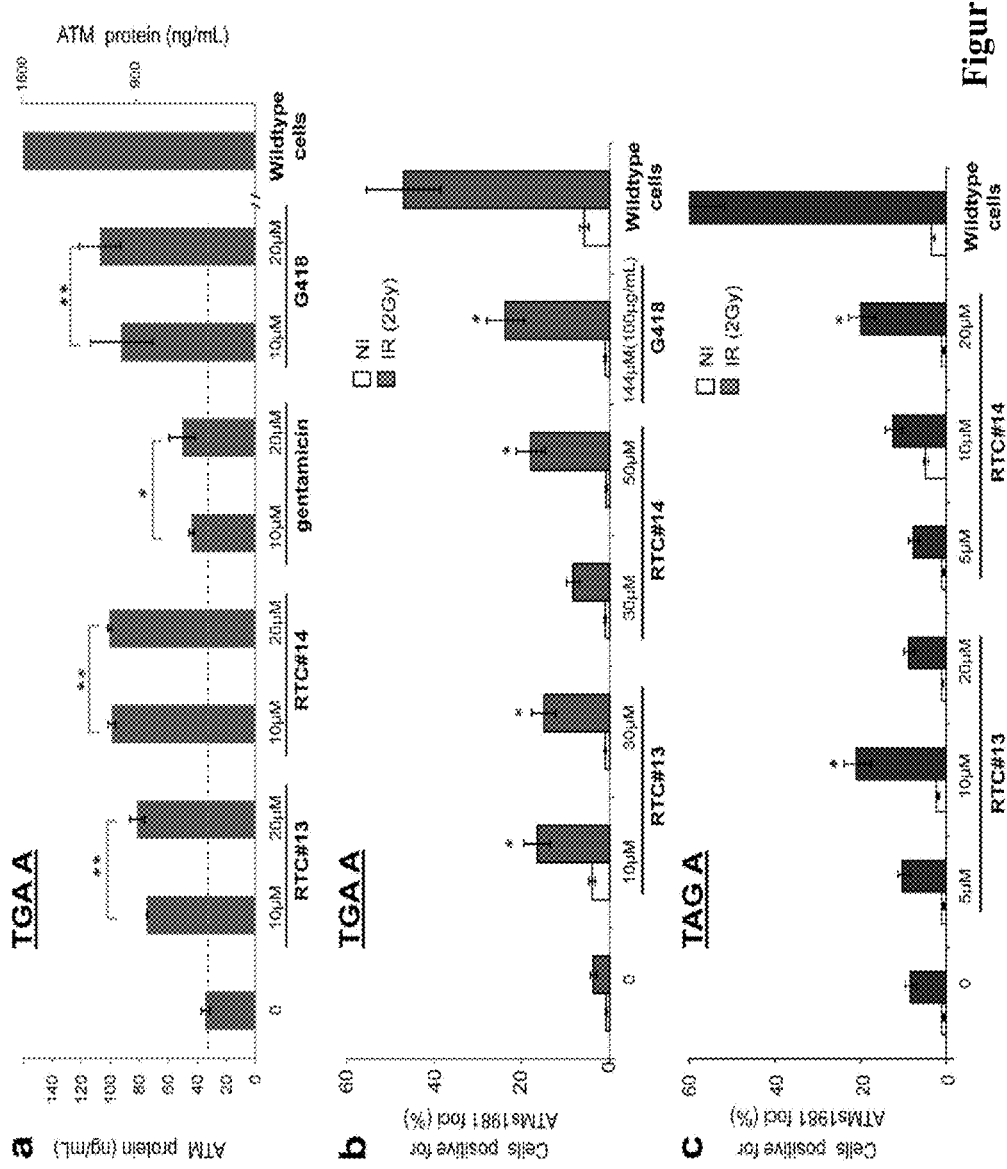
FIGS. 3a-3c show the test results on RTC-induced intranuclear ATM protein and post-IR 3.

To test whether the newly identified compounds could induce ATM protein in A-T cells with PTC mutations, we exposed A-T LCLs to each compound for 4 d before harvesting the cells. Western blotting of nuclear lysates was generally of insufficient sensitivity for monitoring RTC-induced ATM protein (Lai et al., 2004); therefore, we used an ATM-ELISA method to measure intranuclear ATM protein in cells (Butch et al., 2004, *Clin. Chem.* 50:2302-2308). Concentrations of individual RTCs used to treat AT153LA UM with a homozygous TGA A mutation were based on their cytotoxicity profile (data not shown). Cells treated with the highest RTC concentrations still had >70% viability as compared with untreated cells. RTC#13 and #14 consistently induced low but detectable levels of ATM protein in A-T LCLs (FIG. 3a). The restored ATM protein was ≤5% of the wild-type LCLs. Gentamicin and G418 also induced small amounts of ATM protein (FIG. 3a). We were encouraged by these results because A-T patients with some residual ATM protein levels can have substantial ATM kinase activity, and this has been sometimes associated with a later onset and slower progression of symptoms (Gilad et al., 1998, *Am. J. Hum. Genet.* 62:551-561; Chun et al., 2003, *Mol. Genet. Metab.* 80:437-443). Thus, we believe that even modest increases in ATM protein levels have therapeutic potential.

FIGS. 3a-3c show the test results on RTCs induced intranuclear ATM protein and post-IR ATM-Ser1981 foci in A-T LCLs. LCLs were treated with compound for 4 d before harvesting. Induced ATM protein was assessed by ATM-ELISA and ATM-Ser1981 IRIF. For IRIF test, cells were irradiated with 2 Gy and IRIFs were scored after 30 min. All experiments were repeated three times. (a) Cells treated with various doses of compound RTC#13 and #14 showed a significantly increased ATM protein level, as compared with nontreated A-T samples ($P<0.05$). The dashed line indicates the basal ATM protein level in untreated. A-T cells. (b) RTC-induced ATM-Ser1981 IRIF in AT153LA (TGA A) cells. (c) RTC-induced ATM-Ser1.981 IRE in AT229LA (TAG A) cells. *, $P<0.05$; **, $P<0.01$, as compared with untreated sample. Error bars indicate the variation of two independent experiments.

To evaluate the function of RTC-induced ATM protein, we measured irradiation-induced foci (IRIF) formation of ATM-Ser1981 in the same ATI53LA cells (TGA A). A-T cells do not form post-ionizing radiation (IR) ATM-Ser1981 foci because ATM protein is either absent or functionally impaired (usually the former). We found that RTC#13 and #14 induced considerable numbers of ATM-Ser1981 IRIFs in A-T cells with TGA A, whereas only a background level of IRIFs was observed in the untreated controls (FIG. 3b). At same time, ~51% of wild-type cells showed distinct post-IR foci. The maximum IRIF induction achieved in A-T cells by 10 μM RTC#13 was ~40% of wild-type level. As a positive readthrough control, 144 μM of G418 (100 μg/ml) was used to treat cells. Our previous studies had shown that, at this concentration, 6418 induced a maximum level of ATMs1981 IRIF (Lai et al., 2004). As anticipated, significant IRIFs were induced in G418-treated cells. The level in A-T cells was about half that in wild-type cells. The compounds were also tested in another A-T cell line, AT229LA, with homozygous TAG A mutations, and both wrc #13 and #14 induced significant numbers of ATM-Ser1981 IRIF, as compared with nontreated A-T cells (FIG. 3c).

Figure 4:
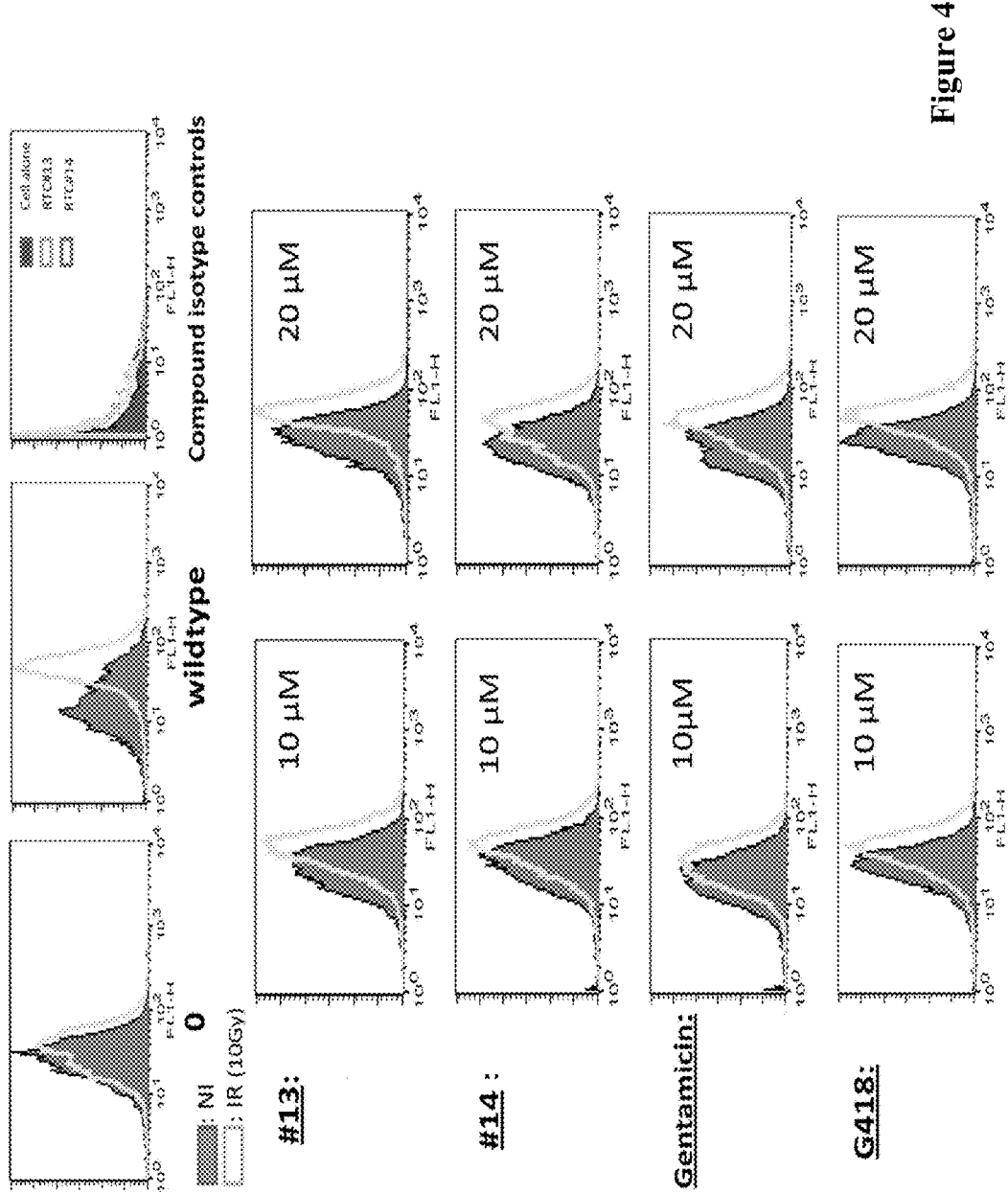
FIG. 4 shows test results on RTC-induced FC-ATM-Ser1981 phosphorylation in A-T LCLs.

To further compare the readthrough activity of RTC#13 and #14 with gentamicin and G418, we used a flow cytometry (FC)-based ATM-Ser1981 phosphorylation assay to assess readthrough activity in AT229LA cells (TAG A; FIG. 4). Both RTC#13 and #14 induced increased ATM-Ser1981 autophosphorylation, as indicated by the right shift of fluorescence intensity (FI). This was consistent with previous ATM IRIF data (FIG. 3c). Encouragingly, ATM-Ser1981 phosphorylation levels induced by RTC#13 and #14 were similar to those induced by the same concentrations of gentamicin and G418 in the same cell line (FIG. 4). Neither of the two compounds produces green autofluorescence (isotype controls; FIG. 4, top right histogram). Similar readthrough effects were also observed in AT153LA cells (TGA A) using cytometry-based ATM-Ser1981 phosphorylation assay (unpublished data).

FIG. 4 shows test results on RTCs induced FC-ATM-Ser1981 phosphorylation in A-T LCLs. AT229LA cells (TAG A) were treated with RTC#13 and #14 for 4 d and analyzed for ATM-Ser1981 phosphorylation using FC. Gentamicin and G418 were used as positive readthrough controls. All compounds induced ATM phosphorylation in A-T cells, as indicated by a right FI shift. Neither compound produced autofluorescence, as shown in the top right histogram. Results were consistent in three independent experiments.

RTC-Induced Restoration of SMC1-Ser966 Phosphorylation in A-T LCLs

Figure 5:
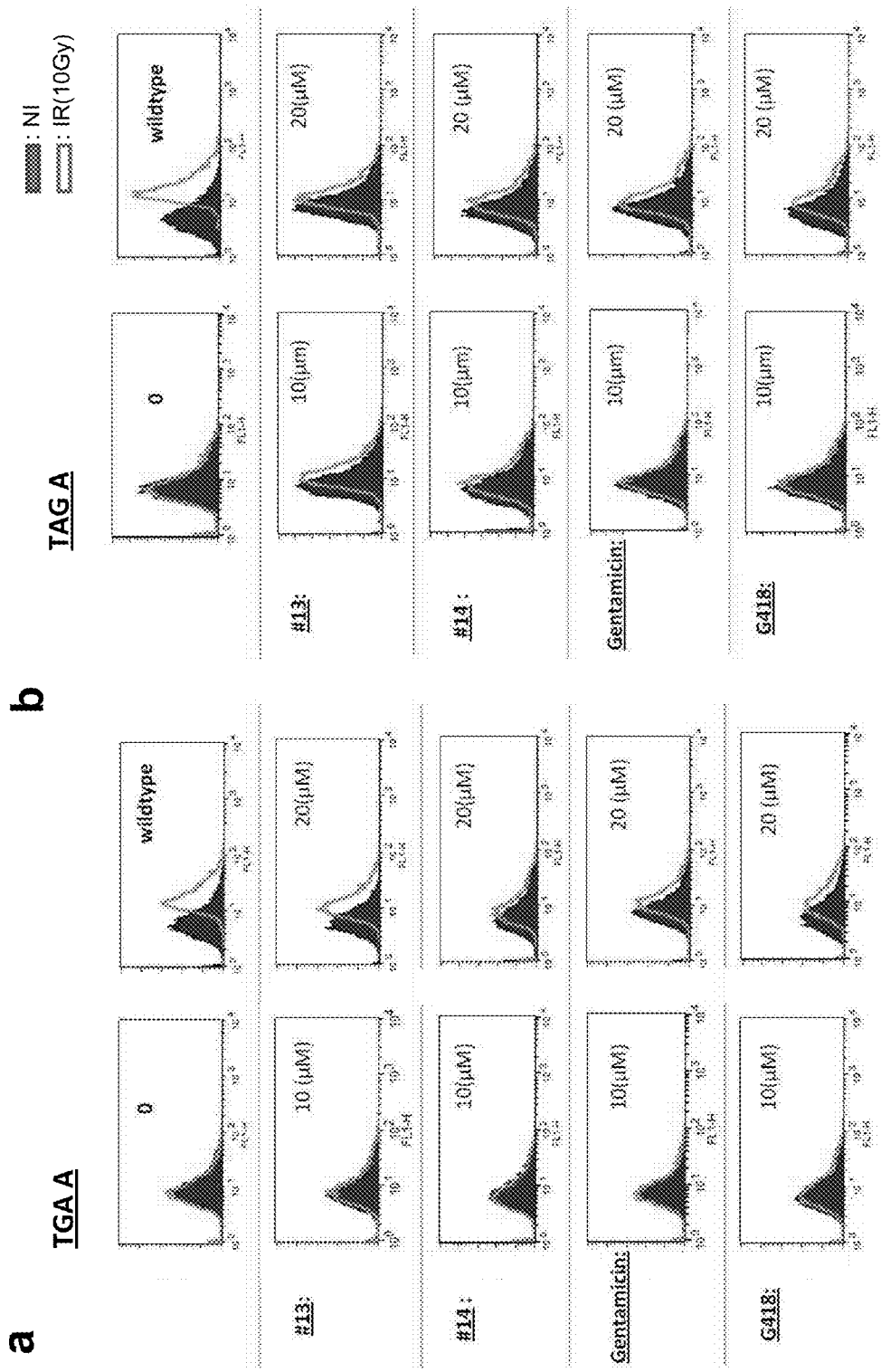
FIG. 5 shows test results on RTC-induced FC-SMC1 pSer966 phosphorylation in A-T LCLs.

As an alternative assay to assess ATM kinase function, we used a recently developed FC-based assay to measure the trans-phosphorylation of SMC1 in A-T LCLs (FIG. 5; Nahas et al., 2009, *Clin. Chem.* 55:463-472). ATM phosphorylates SMC1 at Ser966 and Ser957 after IR-induced double-strand breaks (Yazdi et al., 2002, *Genes Dev.* 16:571-582; Kitagawa et al., 2004, *Genes Dev.* 18:1423-1438), and IR-induced SMC1 phosphorylation is deficient in A-T cells. In untreated AT153LA cells (TGA A), we observed no phosphorylation of SMC1 (FIG. 5a, top, left). After treatment with either RTC#13 or #14, a right shift in FE was observed, indicating restored ATM kinase activity. Both G418 and gentamicin induced SMC1 phosphorylation in A-T cells at similar levels. We also tested the same compounds on TAG A mutation using AT229LA cells. They all induced detectable SMC1 phosphorylation (FIG. 5b). RTC-induced correction of SMC1 phosphorylation was dose dependent in AT153LA cells (TGA A; data not shown).

FIG. 5 shows test results on RTCs induced FC-SMC1 pSer966 phosphorylation in A-T LCLs. (a) RTC#13 and #14 restored SMC Ser966 phosphorylation in AT153LA cells (TGA A). (b) RTC#13 and #14 restored SMC1 Ser966 phosphorylation in AT229LA cells (TAG A). All experiments were repeated three times.

RTC-Induced Restoration of ATM Kinase in A-T Fibroblast Cells

To determine whether the two lead RTCs were also active in other types of cells, we tested them against the A-T fibroblast cell line GM02052, which contains a homozygous TGA G mutation (c. 103C→T). RTC-treated cells showed slightly increased IR-induced SMC1-Ser966 (FIG. 6a) and ATM-Ser1981 phosphorylation (FIG. 6b), as compared with untreated cells. As positive readthrough controls, gentamicin and 6418 showed readthrough activities similar to RTC#13 and #14 at the concentrations compared, indicating that both RTC#13 and #14 were also active on A-T fibroblasts.

Figure 6:
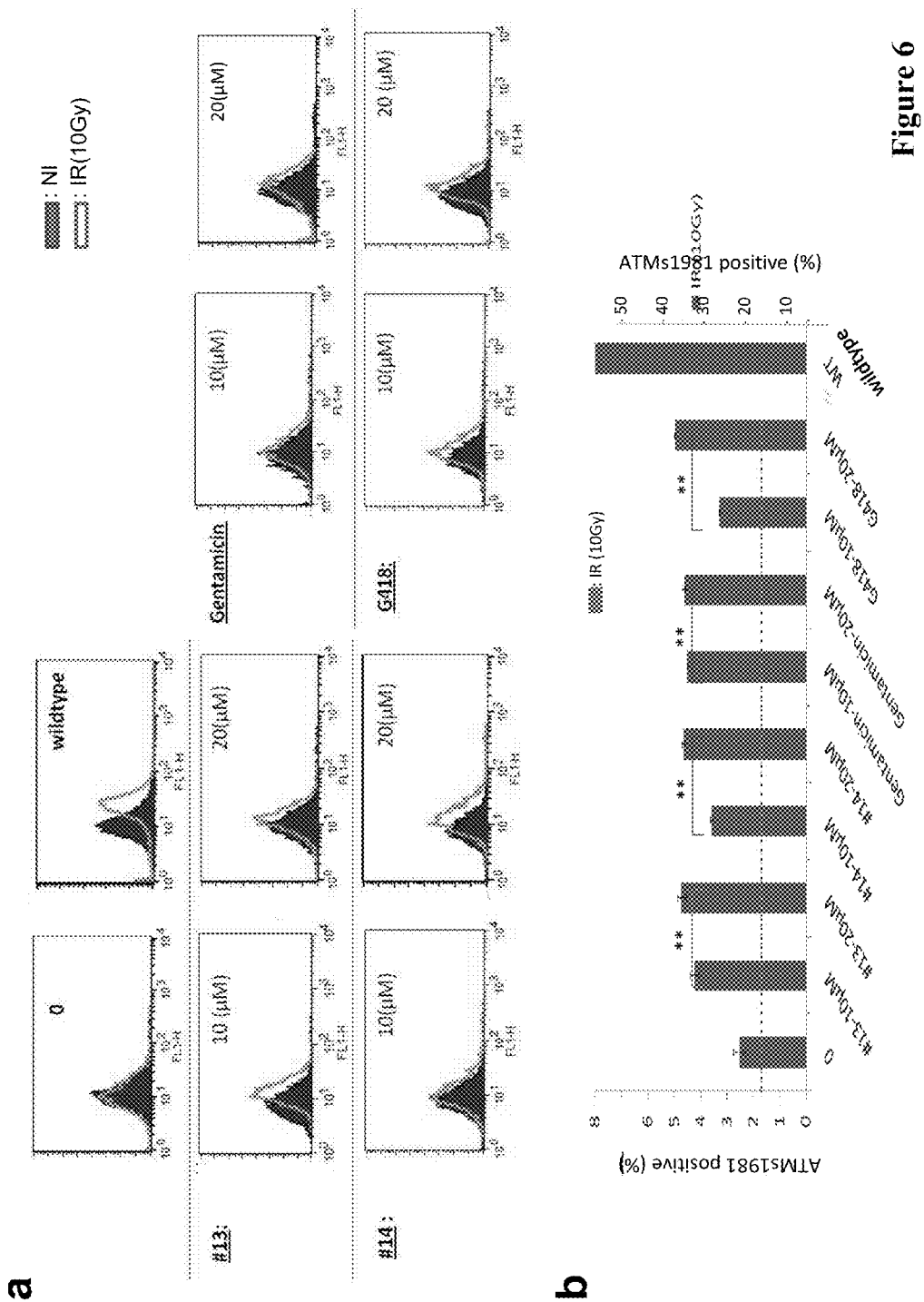
FIG. 6 shows test results on RTC-restored ATM kinase activity in A-T fibroblast cells.

FIG. 6 shows test results on RTCs restored ATM kinase activity in A-T fibroblast cells. GM02052 cells with a homozygous c.103C→T mutation (TGA G) were treated with RTC#13 and #14 for 4 d, and ATM kinase activity was assessed using FC-based SMC1-Ser966 phosphorylation and ATM-Ser1981 phosphorylation. All experiments were repeated three times. (a) Histograms of FC-SMC1-Ser966. (b) Cell population positive for ATM-Ser1981 staining. The dashed line indicates the basal ATM s1981 phosphorylation in the nontreated A-T cells after radiation (10 Gy). **, P<0.01, as compared with untreated sample. Error bars indicate the variation of two independent experiments.

RTC-Induced Cell Survival Correction in A-T LCLs

Figure 7:
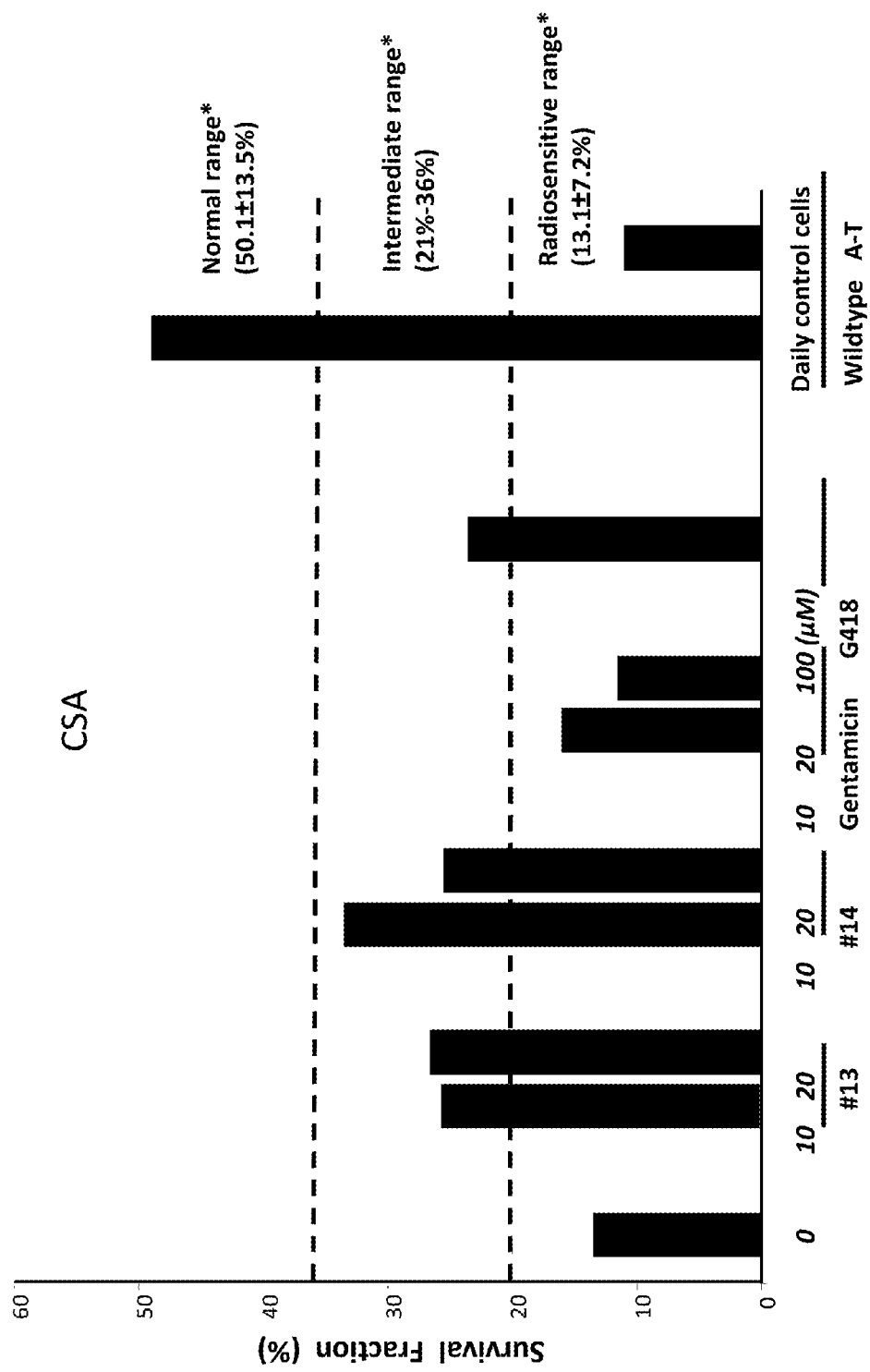
FIG. 7 shows test results on RTC abrogating the radiosensitivity of A-T LCLs.

Because the radiosensitivity of A-T cells results from the ATM deficiency, we next investigated whether RTC#13 and #14 can abrogate A-T cell's radiosensitivity of A-T cells. AT153LA cells (TGA A) were treated with compounds for 4 d and followed by CSA. One wild-type cell line and one different A-T cell line were used as assay quality controls. As expected, the wild-type and A-T controls showed 49 and 11% survival fraction, respectively. These were within the normal (>36%) and radiosensitive (<21%) range, respectively (FIG. 7, right two bars). Untreated AT153LA cells showed a 13.5% survival fraction, which is radiosensitive (FIG. 7, left bar). Encouragingly, we found that both RTC#13 and #14 (at 10 and 20 μM) abrogated AT153LA cell radiosensitivity, from radiosensitive (13.5%) to intermediate (21-36%) range. 100 μM G418 also abrogated radiosensitivity to intermediate range, whereas gentamicin did not show a significant effect in this assay at the tested concentrations (10 and 20 μM). The definition of CSA range used was previously established in our laboratory and is used for clinical A-T diagnosis (see Materials and methods).

FIG. 7 shows test results on RTCs abrogated the radiosensitivity of A-T LCLs. AT153LA cells (TGA A) were treated with compounds and the CSA was measured. RTC#13, RTC#14, and G418 increased cell survival fractions to intermediate range. In FIG. 7, the symbol (*) denotes results fall within the ranges characterized by Sun et al. *J Pediatr,* 140 (6):724-31, 2002. Gentamicin did not show an effect at tested concentrations. Results were consistent in three independent experiments.

RTCs Induced mdx PTC Readthrough in Mouse Myotube Cells

Figure 8:
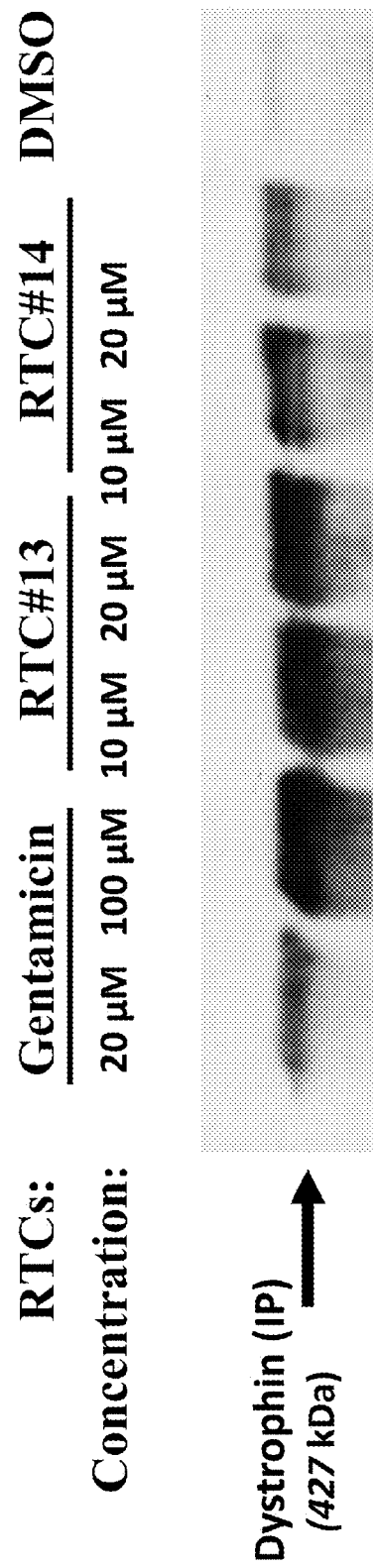
FIG. 8 shows test results on RTCs restoring full-length dystrophin protein in mouse mdx myotubes (TAA).

To investigate the ability of RTC#13 and #14 to readthrough a PTC mutation in genes other than ATM, we used mdx myotubes. The mdx mouse has been widely used as a model for Duchenne muscular dystrophy. It carries a C to T transition in exon 23 of the dystrophin gene that creates a premature stop codon (TAA), resulting in an absence of dystrophin protein (Sicinski, et al., 1989, *Science.* 244:1578-1580). Because gentamicin has been shown to induce readthrough of the mdx PTC mutation and to restore dystrophin expression in mdx mice both in vitro and in vivo (Barton-Davis, et al., 1999, *J. Clin. Invest.* 104:375-381), we used it as a positive readthrough control in the experiments. Muscle progenitor cells isolated from mdx mice were induced to differentiate for 24 h before addition of gentamicin or compounds RTC#13 and #14. Myotube cultures were exposed to compounds for 72 h and then analyzed for dystrophin by Western blotting. Full-length dystrophin was clearly detected in cells treated with RTC#13 and #14 at concentrations of 10 and 20 μM but not in cultures treated with gentamicin at concentrations of 20 μM (unpublished data). We next used immunoprecipitation to increase the sensitivity of the assay (FIG. 8). Dystrophin expression was present in cells treated with gentamicin at concentrations of 20 and 100 μM. Both of our lead compounds showed readthrough activity, inducing significant amount of dystrophin protein. Results were consistent in multiple experiments performed.

FIG. 8 shows test results on RTCs restored full-length dystrophin protein in mouse mdx myotubes (TAA). Cells were prepared and treated with RTCs for 3 d. Dystrophin proteins were detected by Western blot analysis using immunoprecipitation. Wild-type cells were used in the experiment to localize dystrophin protein. Gentamicin was used as a positive readthrough control. Both RTC#13 and #14 induced a significant amount of dystrophin protein. Results were consistent in three independent experiments.

Discussions

We believe HTS can identify new nonaminoglycoside RTCs with therapeutic potential. In this study, we used A-T as a disease model to identify new RTCs. A-T is a progressive autosomal recessive neurodegenerative disorder resulting from mutations in the ATM gene (Perlman et al., 2003, *Semin. Pediatr. Neurol.* 10:173-182; Chun and Gatti, 2004, *DNA Repair (Amst.).* 3:1187-1196). ATM protein plays a very important role in cell cycle control, DNA damage repair, the oxidative stress response, and apoptosis (Shiloh, 2006, *Trends Biochem. Sci.* 31:402-410). The A-T disorder provides an appropriate laboratory model for demonstrating novel principles of mutation-targeted therapy. In the ATM mutation spectrum, primary nonsense mutations account for ~15% of the unique mutations detected in A-T patients (www.LOVD.nl/ATM). A well characterized spectrum of ATM mutations, supported by an extensive library of LCLs derived from patients with those mutations, allowed us to investigate the effect of nonaminoglycoside RTCs on various primary premature stop codons. We have previously used aminoglycosides and antisense oligonucleotides to correct nonsense and splicing ATM mutations, respectively, and to restore functional ATM protein in A-T LCLs (Lai et al., 2004; Du et al., 2007, *Proc. Natl. Acad. Sci. USA.* 104:6007-6012). These studies suggest that therapeutic benefits might be achieved if even modest increases in functional ATM protein levels can be induced. In these limited studies, we saw no significant effects on efficiency of readthrough from the fourth nucleotide of each tested stop codon.

Herein, we successfully developed a sensitive luciferase-independent HTS assay by coupling PTT and ELISA. PTT-ELISA shows high specificity for detecting readthrough products and, thus, minimizes false positives in the initial large-scale library screening. The assay is also very sensitive; the minimum detection threshold is ~1%, which ensures its efficiency as a HTS assay. The efficiency of PTT-ELISA was further evaluated using two well known RTCs, G418 and gentamicin. The assay was able to detect their readthrough activity over a very large concentration range (G418, 40 nM-10 µM; gentamicin, 40 nM-100 µM). Furthermore, PTT-ELISA has been validated for a fully automated robotic platform, with consistent accuracy between plates. The 384-well format dramatically reduced the workload for screening thousands of compounds and also saved time, costs, and reagents. Moreover, this assay has the potential to be validated for a 1,536-well format. For these reasons, we believe that the PTT-ELISA HTS assay provides a powerful new tool for identifying new RTCs.

From a library of ~34,000 compounds, we identified 12 low-molecular-mass compounds (between ~300 and 450 daltons) with PTC readthrough activity. None of these new compounds were aminoglycosides. Several compounds showed $EC_{50}$ values <10 µM, implying their potential for further development. To further assess these compounds in cell systems, we tested their readthrough activity in A-T LCLs with a variety of nonsense mutations. We used ATM-ELISA to directly detect ATM protein levels in treated cells. Subsequently, more sensitive cell-based assays, such as FC-based SMC1-Ser966, ATM-Ser1981 phosphorylation, and ATM-Ser1981-IRIF, were used to assess restored ATM kinase activity. Among the 12 compounds, RTC#13 and #14 showed PTC readthrough activity in A-T cells, both in LCLs and fibroblasts, as demonstrated by ATM-ELISA, ATM kinase activity (autophosphorylation of ATM and trans-phosphorylation of SMC1), and CSA. To determine whether the compounds can read through PTC mutations in other genes, we selected mouse mdx myotube cells and tested their ability to induce readthrough in a different species, a different cell type (non-dividing muscular cells), and a different premature stop codon (TAA). In other studies, the TAA codon has proven the most difficult to read through (Kimura et al., 2005, *Brain Dev.* 27:400-405; Welch et al., 2007). Both RTC#13 and #14 induced PTC readthrough of the mouse mdx dystrophin gene.

Collectively, our data showed that both RTC#13 and #14 had comparable readthrough activity in cell-based assays, even though their activities in cell-free PTT-ELISA assay were much lower than gentamicin and G418. This may be associated with differences in cell-based metabolism, drug solubility, and permeability of compounds.

To assess the impact of the compounds on readthrough of normal stop codons of other proteins, we performed two-dimensional gel electrophoresis. Neither compound significantly interfered with protein expression patterns (data not shown), implying that these compounds have potential for further development. However, we anticipate that significant therapeutic effects may not be discernable in A-T patients if the RTC-induced ATM level is <15% of normal, and this very likely also applies to other genetic disorders. Therefore, further structural modifications to improve pharmodynamics will be necessary. Structural optimization has improved the readthrough activity and lowered the toxicity of aminoglycosides (Nudelman et al., 2006, *Bioorg. Med. Chem. Lett.* 16:6310-6315; Rebibo-Sabbah et al., 2007, *Hum. Genet.* 122:373-381). Therefore, it is expected to be effective for developing better nonaminoglycoside readthrough analogues as well.

The underlying mechanisms of PTC readthrough activity for these newly identified compounds remain unknown. It has been demonstrated that all of the known PTC-RTCs function by interfering with ribosomal translation. Certainly, aminoglycosides interact with the decoding center of the ribosomal 16S subunit and cause misincorporation of an amino acid at the PTC site which allows translation to continue (Keeling and Bedwell, 2005; Zingman et al., 2007). PTC124 is believed to act at a different location on the ribosome (Linde and Kerem, 2008, *Trends Genet.* 24:552-563). It will be interesting to learn whether RTC#13 and #14 interact with the ribosome.

It has been reported that nonsense-mediated messenger RNA (mRNA) decay (NMD) can significantly affect RTC-induced PTC-readthrough because mRNA transcripts carrying nonsense mutations are degraded by this pathway (Wilkinson and Shyu, 2002, *Nat. Cell Biol.* 4:E144-E147; Holbrook et al., 2004, *Nat. Genet.* 36:801-808). Therefore, inhibition of NMD may stabilize mutant mRNA transcripts and increase RTC-induced readthrough output (Linde et al., 2007, *J. Clin. Invest.* 117:683-692; Linde and Kerem, 2008). We have examined this in our laboratory using many different ATM nonsense mutations, and we have failed to detect a clear pattern of NMD or inhibition of NMD, suggesting that NMD in A-T cells may be a matter of degree. NMD efficiency may also vary between different mutations and different genes. The role of NMD in RTC-induced treatment remains to be clarified.

Materials and Methods

Plasmas Construction.

To construct plasmids containing stop codon mutations in their own context, we selected ATM nonsense mutations that resulted directly from disease-causing point mutations in A-T patients. The LCLs used in this study carried the following mutations: TAT51, homozygous 5623C→T (TGA C); AT185LA, homozygous 3673C→T (TAA G); and AT153LA, homozygous 8977C→T (TGA A). Reverse-transcription PCR was performed using custom designed primers which introduced N- and C-terminal epitopes (c-myc and V5, respectively) into the PCR products (Du et al., 2008). PCR products were then cloned into pcDNA5/FRT/TO TOPO plasmids according to the manufacturer's protocols (Invitrogen). The PCR products for each mutant were mutagenized back to normal and used as paired normal control plasmids. DNA sequencing confirmed the PTT fragments in all constructs.

High-Throughput PTT-ELISA,

Three chemical libraries, ChemBridge, Prestwick, and MicroSource, were used in our primary screening. The final concentration for each compound tested was 10 μM. Screening was performed on a fully integrated CORE System (Beckman Coulter). PTT was performed in a reaction volume of 5 μl. The TNT T7 PCR Quick Master Mix, containing 20 μM methionine, was aliquoted into a 384-well low-volume plate (MatriCal Bioscience). Compounds were added using a 384-well pin tool (V&P Scientific, Inc). The PTT reaction was started by the addition of purified plasmid at 50 ng/well, which was incubated for 2 h at 30° C. PTT samples were subsequently stored at 4° C. for ELISA analysis. For each plate, G418 at a final concentration of 1 μM served as positive control and reactions with 1% DMSO served as negative control. ELISA was performed in a 384-well MaxiSorp ELISA plate (Nunc). The plate was coated with 20 μl of 5-μg/ml mouse anti-Myc antibody (Invitrogen) overnight at 4° C., followed by washing with PBS and blocking with 50 μl PBSTM (PBS-containing 0.05% Tween-20 and 5% milk) for 30 min at 37° C. 20 μl $H_2O$ was added in PTT plate and 15 μl of reaction solution was transferred into ELISA plate, followed by overnight incubation at room temperature. After washing the plate, 20 μl of 1:500 mouse anti-V5 HRP (Invitrogen) was added and incubated for 2 h at 37° C. The plate was washed, incubated with 30 μl SuperSignal ELISA Pico working solution (Thermo Fisher Scientific), and measured on the Victor-3V using "top read" and an integration time of 0.5 s.

Immunoassay for Measurement of Intranuclear ATM Protein.

Readthrough-induced full-length ATM protein in A-T cells was measured by ATM immunoassay (Butch et al., 2004). Cell nuclear extracts were prepared using NE-PER protocol (Thermo Fisher Scientific). Then ATM-ELISA was performed using 200-μg nuclear extracts. ATM concentrations of tested samples were calculated from the standard calibration curve using purified ATM protein (Chun et al., 2004, *Biochem. Biophys. Res. Commun.* 322:74-81).

Immunofluorescence of ATM-Ser1981 IRIF.

Immunostaining of nuclear foci of ATM-Ser1981 was performed as previously reported (Du et al., 2007). In brief, after being treated with compound for 4 d, cells were irradiated with 2 Gy and incubated at 37° C. for 30 min. The cells were dropped onto coverslips, fixed with 4% paraformaldehyde, and permeabilized. Coverslips were blocked for 1 h and incubated with mouse anti-ATM pSer1981 for 1 h (1:500; Rockland Immunochemicals, Inc). After a second blocking, cells were stained with FITC-conjugated anti-mouse IgG (1:150; Jackson ImmunoResearch Laboratories) for 1 h and mounted onto slides.

FC Analysis of ATM-Ser1981 and SMC1-Ser966 Phosphorylation.

FC-SMC1 assay was performed as recently described (Nahas et al., 2009). FC-ATM-Ser1981 assay was based on Honda's assay (Honda et al., 2009, *Leukemia*. 23:409-414) with modifications. In brief, cells were resuspended in PBS and radiated for 10 Gy. After 1 h, the cells were fixed and permeabilized using the FIX & PERM cell permeabilization kit (Invitrogen). The cells were then incubated with 1 μl of mouse ATM-Ser1981 antibody (Cell Signaling Technology) for 2 h at room temperature. Cells were washed and resuspended in 100 μl PBS with Alexa Fluor 488 anti-mouse IgG (Invitrogen) for 45 min. Cells were next washed and resuspended in PBS with 0.2% paraformaldehyde and analyzed using a FACS-Calibur (BD).

CSA.

CSA was performed as previously described (Sun et al., 2002, *J. Pediatr.* 140:724-731). After 4 d of incubation with compounds, LCLs were plated, in duplicate, in 96-well plates at 100 and 200 cells per well. One plate was exposed to 1.0 Gy radiation, whereas the other was left unirradiated. The cells were incubated for 10-13 d and then stained with MTT. The presence of a colony of 32 cells was scored as a positive well, and survival fractions were calculated.

Mdx Myotubes Treatment and Western Blot Analysis of Dystrophin.

Cells were derived from limb muscle of neonatal mdx and C57 mice, as previously described (Bertoni and Rando, 2002, *Hum. Gene Ther.* 13:707-718). For growth, cells were plated on dishes coated with 5 g/ml laminin (Invitrogen) and maintained in growth medium consisting of Ham's F10 nutrient mixture (Mediatech, Inc.) supplemented with 20% fetal bovine serum, penicillin, and streptomycin. Cell differentiation was induced by maintaining the cells in low serum medium (differentiation medium) consisting of DME supplemented with 2% horse serum, penicillin, and streptomycin. Myoblasts were plated in wells of 6-well dishes and were allowed to differentiate for 24 h before adding the compounds. Media was replaced every 24 h with fresh differentiation media containing the compounds. Cells were lysed 96 h after induction of differentiation (72 h after addition of the compounds). Total protein was determined and dystrophin immunoblot analysis was performed as previously described (Sicinski et al., 1989). 250 μg of total protein from each sample was immunoprecipitated using a monoclonal antibody directed toward the rod domain (MANDYS—8; 1:40; Sigma-Aldrich) of the dystrophin protein and detected by Western blotting (Barton-Davis et al., 1999, *J. Clin. Invest.* 104:375-381; Bertoni and Rando, 2002).

Statistical Analysis.

Analysis of variance was performed for comparison of multiple means, and a two-sample Student's t-test was used for comparison of two means. Statistical significance ($P<0.05$) was assessed using Prism 4 (GraphPad Software, Inc).

Example 2

Readthrough Studies on Compounds Derivatives of RTC#13

Readthrough studies were performed on derivatives of RTC#13 following the procedures of each test described in Example 1.

Figure 9:
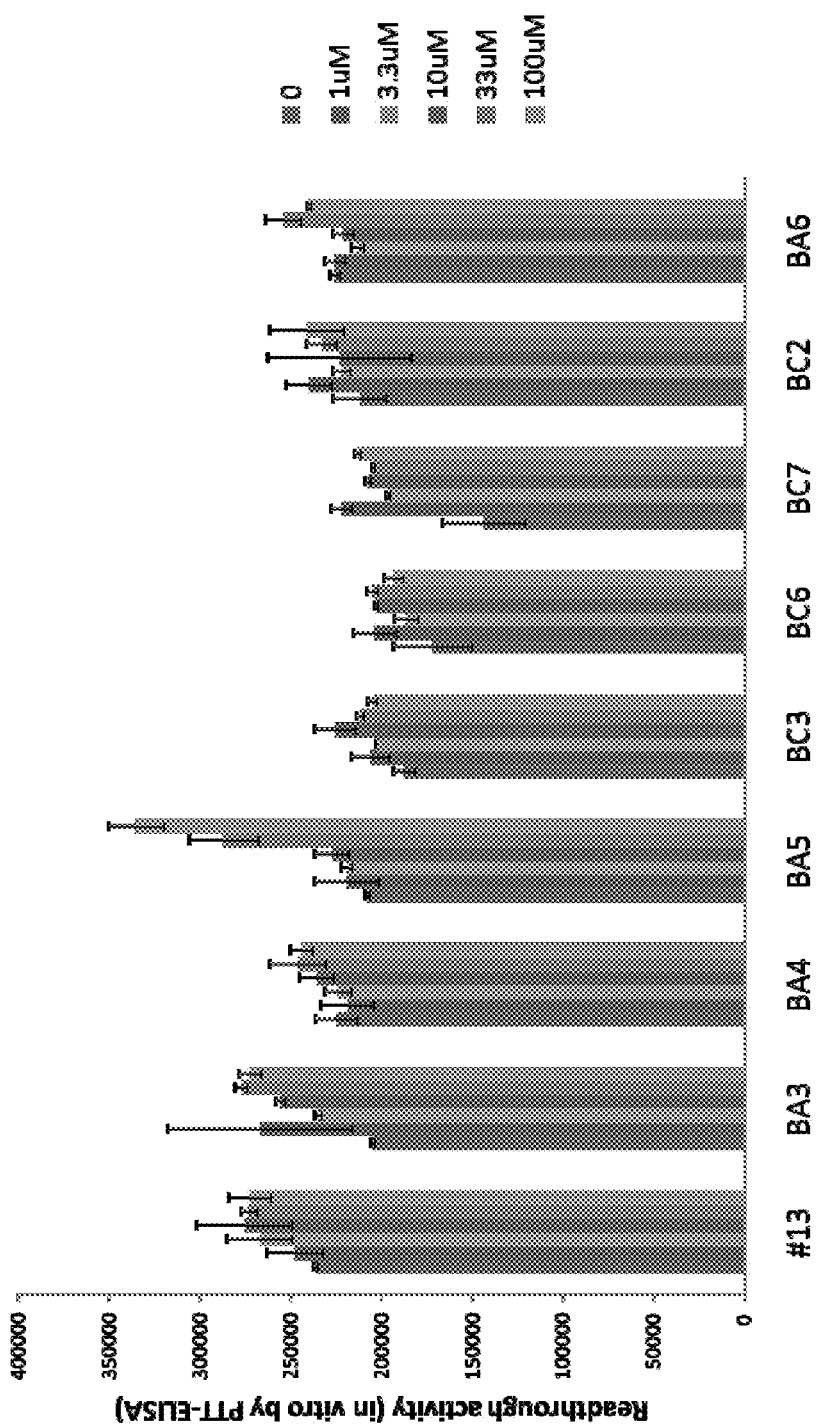
FIG. 9 shows the results of studies on in vitro readthrough activity of RTC#13 and derivatives as measured by PTT-ELISA.
Figure 10:
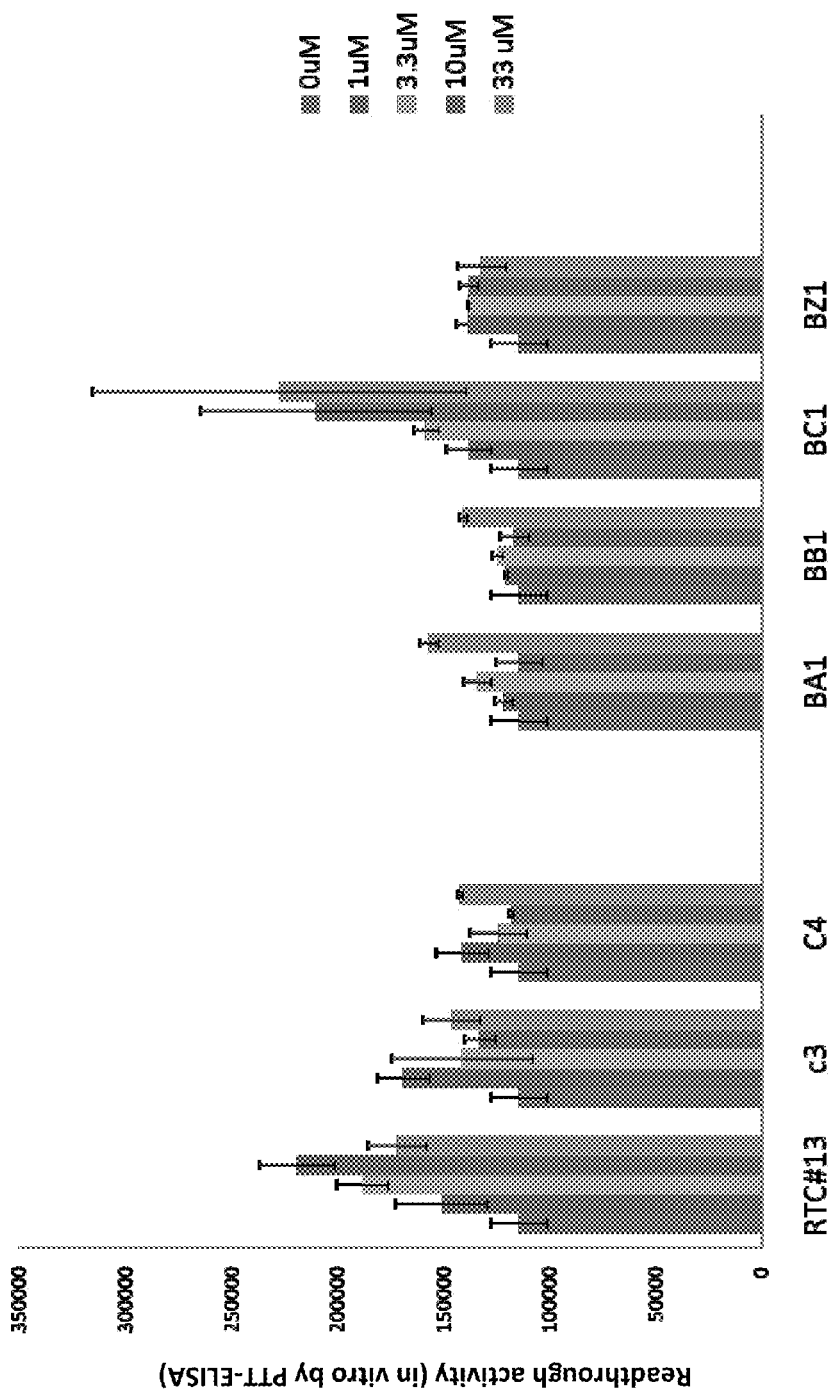
FIG. 10 shows the results of studies on in vitro readthrough activity of RTC#13 and derivatives as measured by PTT-ELISA

Studies on in vitro readthrough activity of RTC#13 derivatives as measured by PTT-ELISA were performed according to the procedures provided in Example 1. The results are summarized in FIGS. 9 and 10.

Figure 11:
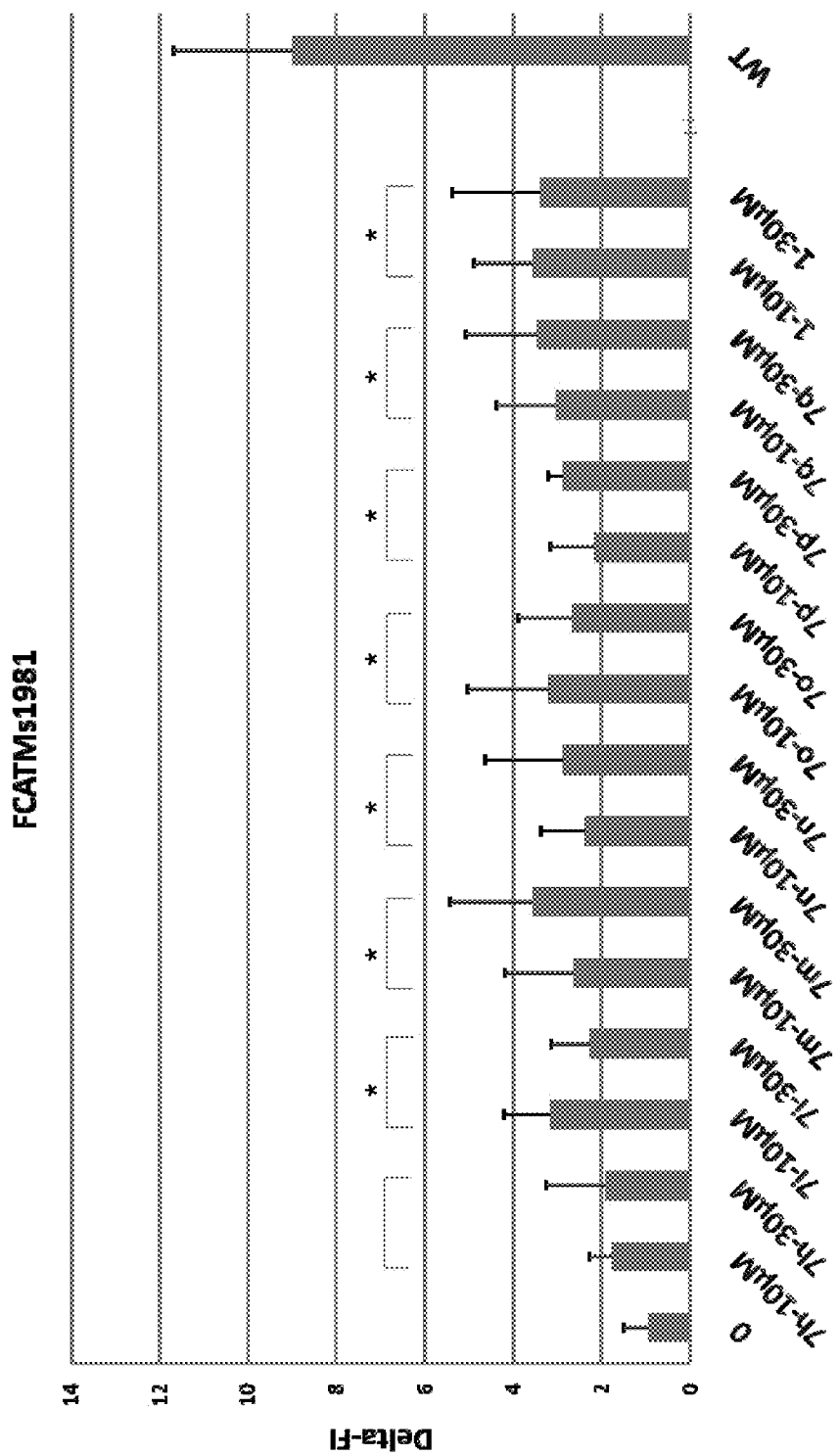
FIG. 11 shows the results of studies on FC-ATMs1981 autophosphorylation induced by RTC#13 and derivatives in AT153LA cells (with TGA)

Studies on readthrough activity of RTC#13 derivatives as measured by FC-ATMS 1981 were performed according to the procedures provided in Example 1. The results are summarized in FIGS. 11 and 12.

Figure 13:
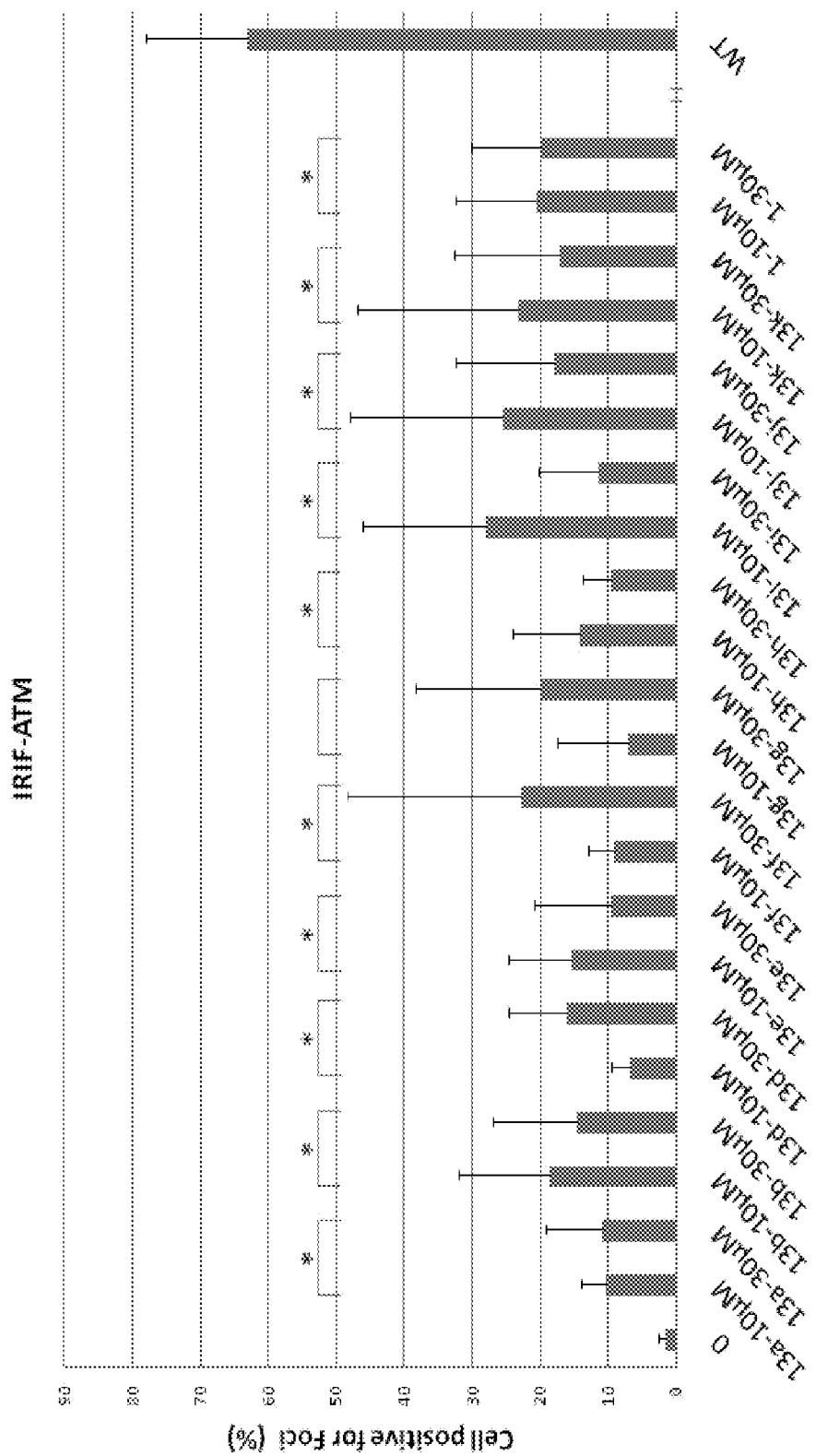
FIG. 13 shows the results of studies of ATMs1981 foci formation assay induced by RTC#13 and derivatives in AT153LA cells (with TGA).

Studies on IR-induced ATMs1981 foci formation by RTC#13 and derivatives 13a, 13b, 13d, 13e, 13f, 13g, 13h, 13i, 13j, and 13k in A-T153LA cells (TGA) were performed according to the procedures provided in Example 1. The results are summarized in FIG. 13 and all RTC#13 derivatives show statistically significant readthrough activity except for Derivative 13g.

Example 3

Readthrough Studies on Compounds Derivatives of RTC#13

Readthrough studies were performed on RTC#13 and RTC#14 following the procedures of each test described in Example 1.

Figure 14:
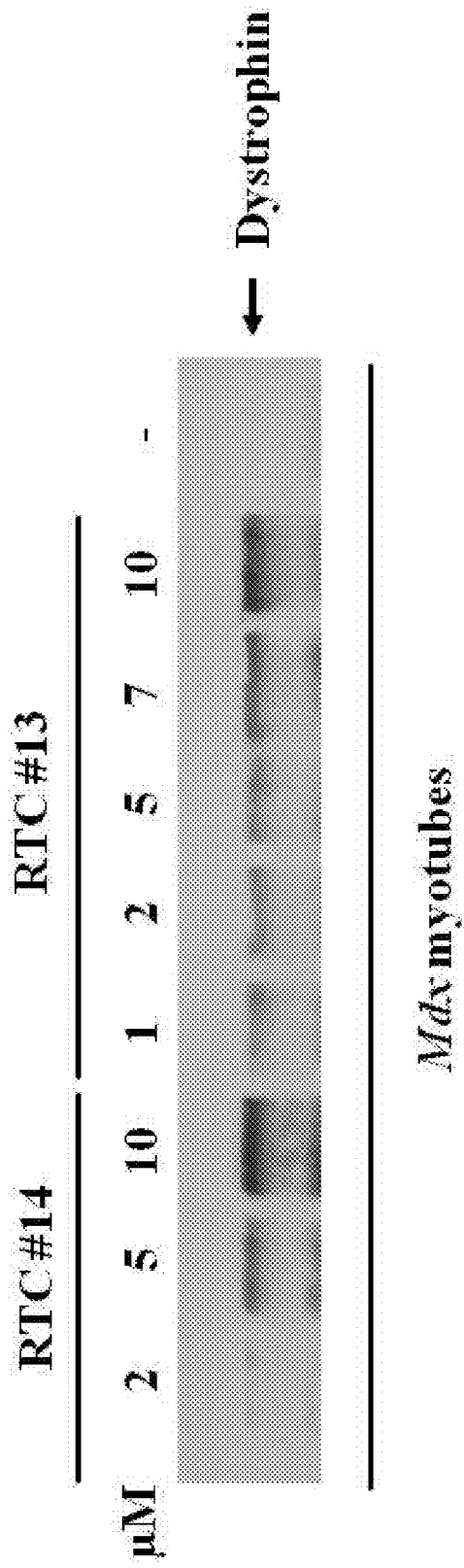
FIG. 14 shows expression in mdx myotubes (with TAA) after exposure to RTC#13 and RTC#14 showing increasing concentrations of dystrophin expression in a dose dependent manner of RTCs.

Dystrophin expression in mdx myotube cells after exposure to RTC#13 and RTC#14 showing increasing concentrations of dystrophin expression in a dose dependent manner of RTCs. Muscle cells were induced to differentiate to allow the formation of myotubes and synthesis of dystrophin mRNA. Compounds were added 24 hrs after induction of differentiation by direct addition into the media. The media was replaced every 24 hrs with fresh differentiation media containing the appropriate concentration of compounds. Myotubes were harvested 72 hrs later (96 hrs after induction of differentiation) and analyzed for dystrophin expression by immunoblot analysis (FIG. 14).

Figure 15:
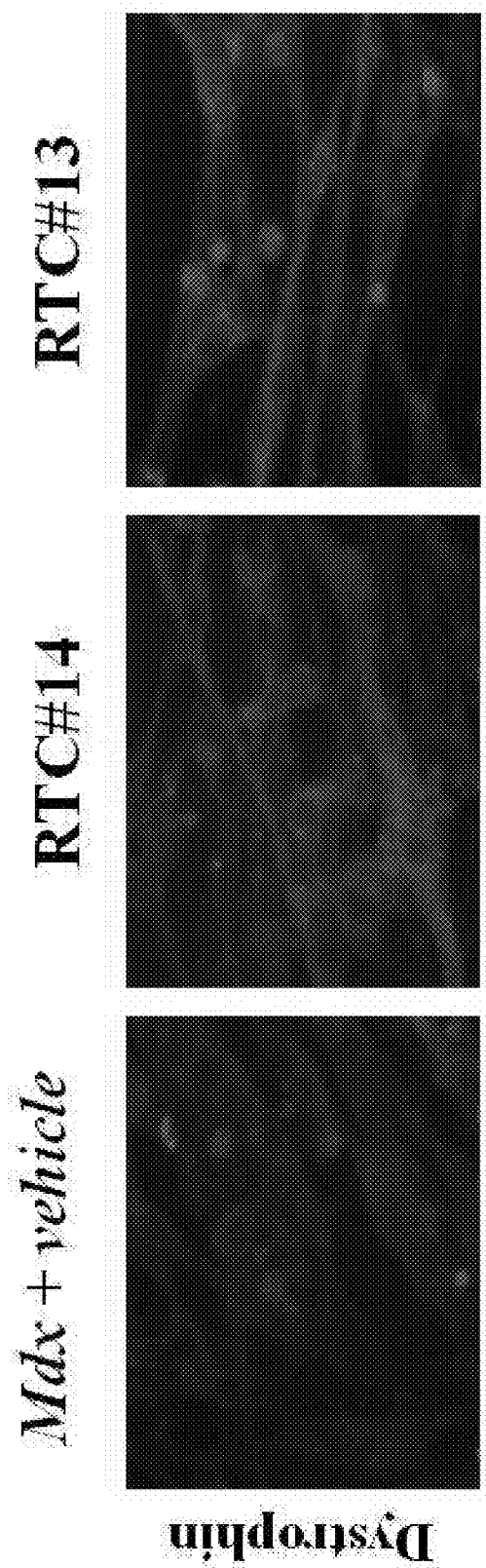
FIG. 15 shows the results of studies on mdx muscle cells (with TAA) induced to differentiate for 24 hrs and then exposed to RTC#13 or RTC#14 to a final concentration of 10 µM for an additional 24 hrs.

In the tests as shown in FIG. 15, mdx muscle cells were induced to differentiate for 24 hrs and then exposed to RTC#13 or RTC#14 to a final concentration of 10 μM for an additional 24 hrs. Cultures were analyzed for dystrophin expression by immunohistochemistry. Dystrophin protein is clearly detected in cultures treated with the RTCs, but not in cells exposed to vehicle (DMSO) only.

Figure 16:
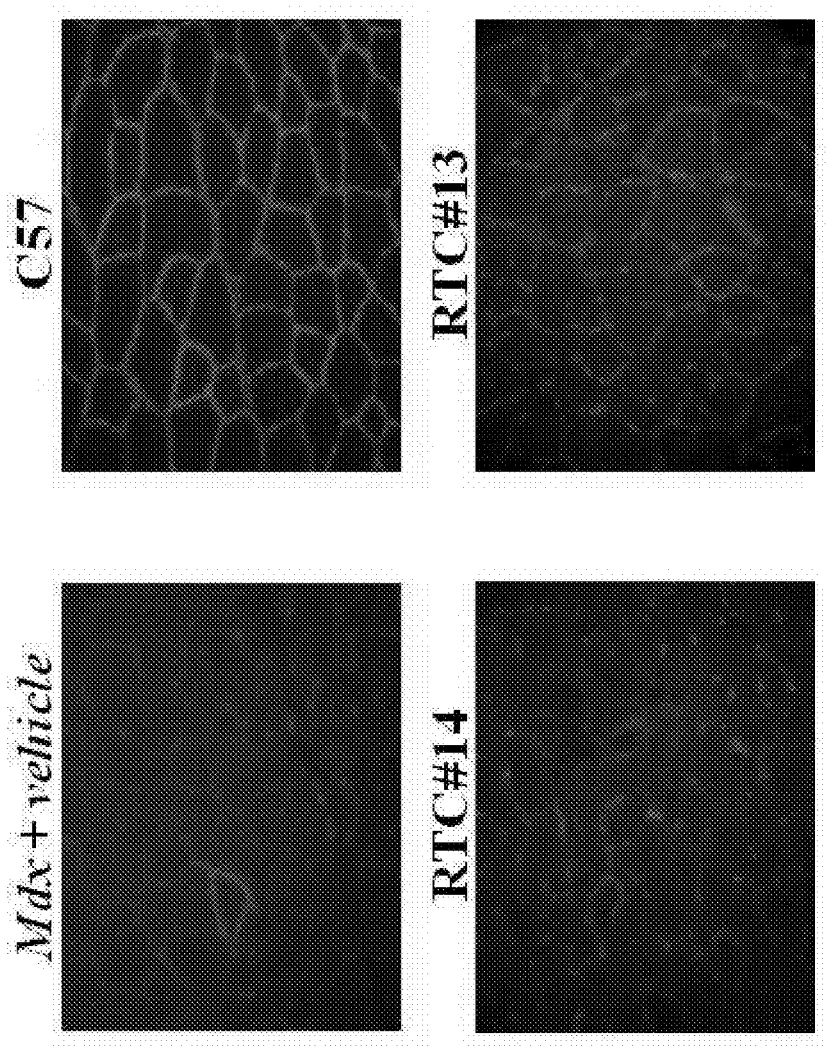
FIG. 16 shows the results of studies showing the ability of RCT #13 and RTC#14 to induce readthrough of premature stop codons in the dystrophin gene of mdx mice (with TAA).

In the tests shown in FIG. 16, the ability of RCT #13 and RTC#14 to induce readthrough of premature stop codons was analyzed in skeletal muscles of mdx mice. Tibialis anterior (TA) were injected with 100 μg of compounds and muscles were analyzed for dystrophin expression two weeks later. Muscles that received RTC#14 did not show significant amounts of dystrophin expression. Expression was much higher in muscles that received RTC#13 and demonstrated that this compound was more effective in inducing readthrough activity in vivo as compared to RTC#14. Differences in fluorescence intensity between wild type and RTC#13-injected tibialis anterior (TA) suggest that the compound was able to only partially restore dystrophin expression within each individual myofiber targeted for repair.

Figure 17:
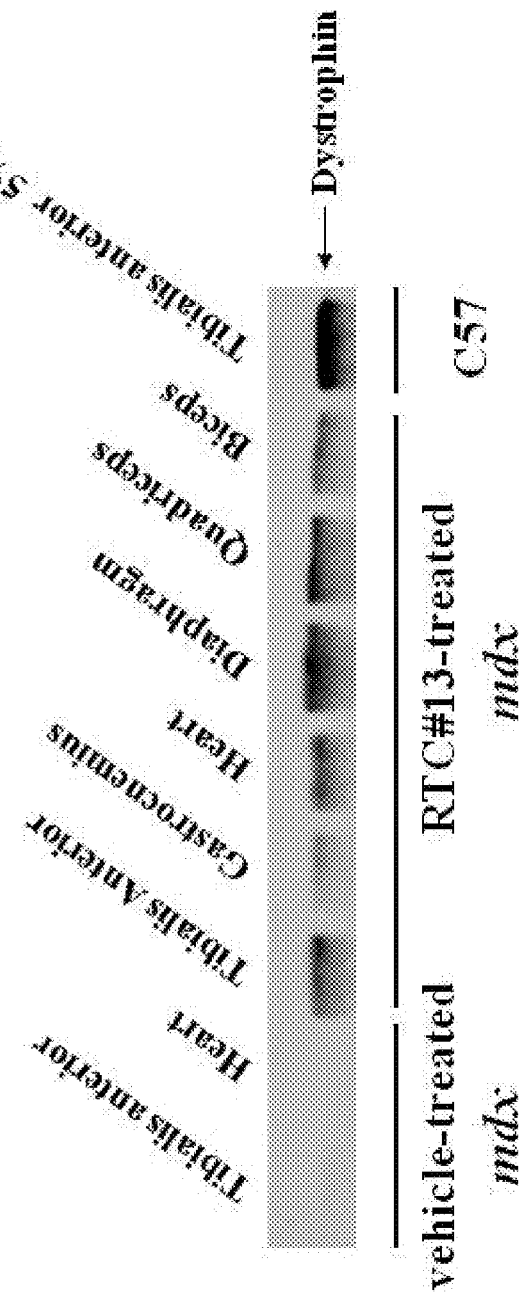
FIG. 17 shows the results of immunoblot studies on the efficacy of RTC#13 to restore dystrophin expression after systemic administration to mdx mice (with TAA).

FIG. 17 shows the results of studies on the efficacy of RTC#13 to restore dystrophin expression after systemic administration, which was assessed in three-month-old mdx mice. In these studies, animals were injected intraperitoneally with RTC#13 at a concentration of 300 mg/kg for three weeks with a wash out period of 5 days between each treatment. Mice were allowed to recover for three weeks and muscles were analyzed for dystrophin expression. Western blot analysis revealed the presence of full-length dystrophin in all tissues isolated from RTC#13 treated mice but not in muscles treated with vehicle only. Expression varied between different muscle groups. Dystrophin was prominent in diaphragm and heart, two of the tissues most affected in DMD patients.

Figure 18:
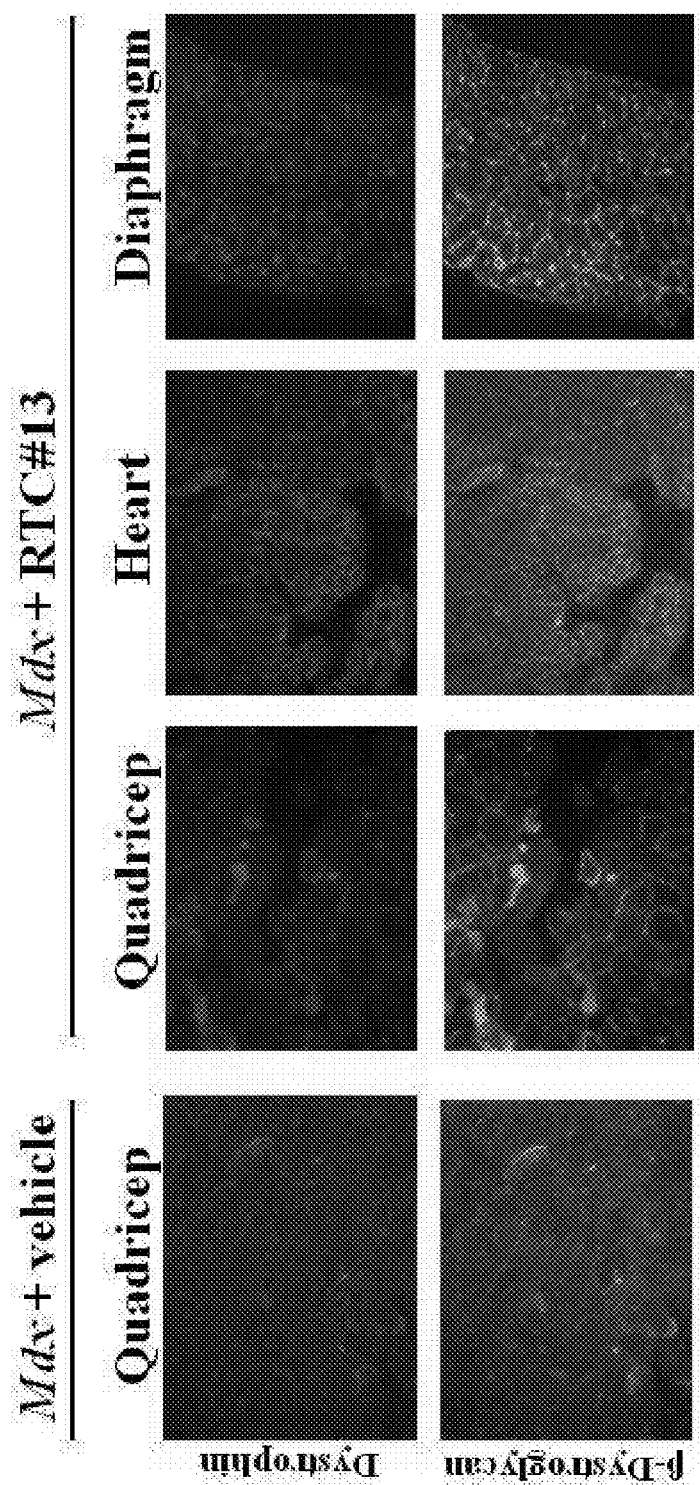
FIG. 18 shows the results of immunohistochemistry analyses of muscle fibers for mdx mice (with TAA) showing that dystroophin protein was functionally active and was able to restore β-dystroglycan expression.

FIG. 18 shows the results of immunohistochemistry analyses, which were used to confirm the immunoblot results shown in FIG. 17. The dystrophin protein produced in muscle fibers was functionally active and was able to restore β-dystroglycan expression, a major component of the dystrophin glycoprotein complex (DGC) that is missing in mdx mice and in human patients as the result of the lack of dystrophin expression.

Figure 19:
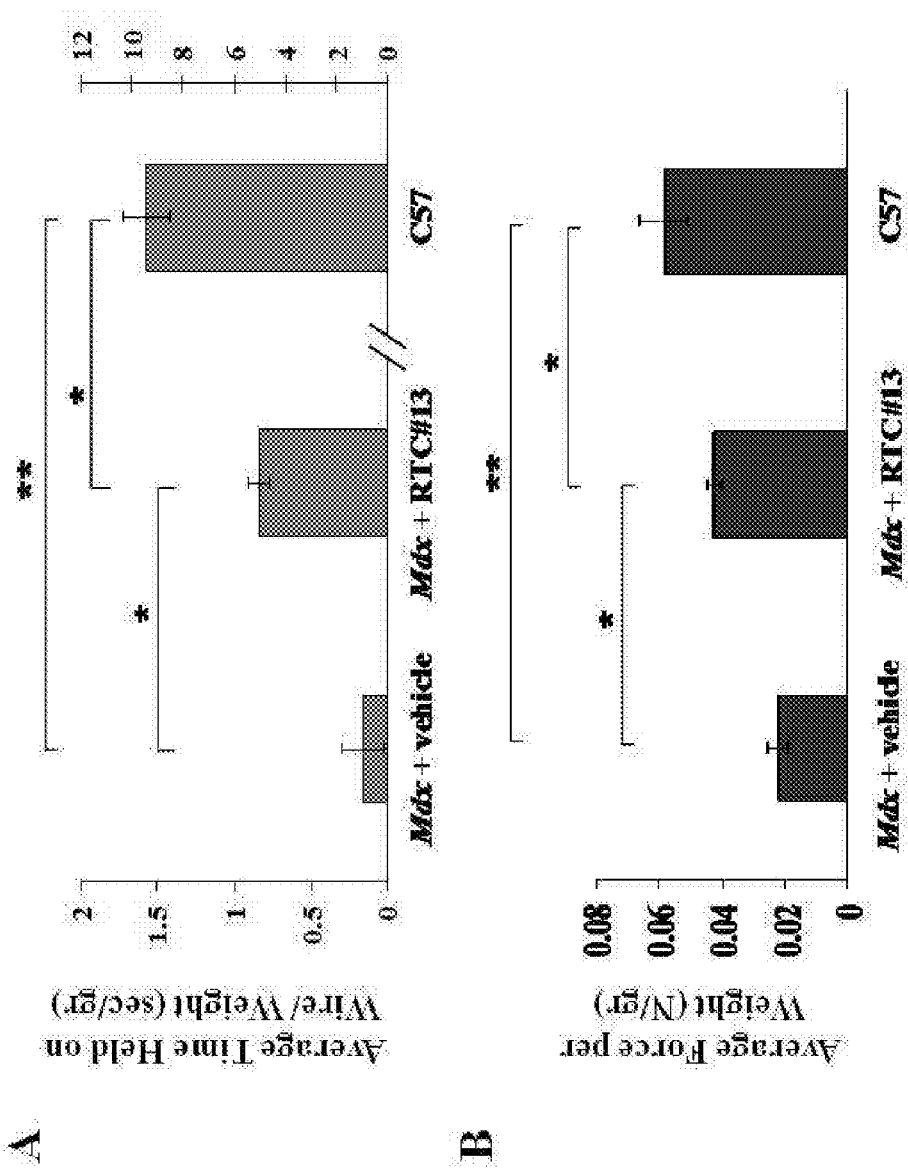
FIG. 19 shows the results of the forelimbs grip test on mdx mice (with TAA) after intraperitoneal injection of RTC#13.

FIG. 19 shows the results of the forelimbs grip test, which was used to determine whether the amount of dystrophin being restored could ameliorate the dystrophic phenotype in mdx mice and to further expand our understanding of the therapeutic potentials of RTC#13 for treating of DMD. Mdx mice were injected intraperitoneally with RTC#13 or vehicle only for three weeks and analyzed two weeks later. In FIG. 19a, muscle strength in treated and untreated mice was determined using the grip test. The top three of five consecutive pulls were averaged to calculate the absolute strength which was then divided by the body weight (BW) in grams. Results were compared to those obtained in wild type (C57) mice. A significant recovery in muscle strength was evident in all animals that received RTC#13 systemically. (*: $p \le 0.01$; : $p \le 0.001$). FIG. 19**b shows similar results were obtained using the wire test. Mdx mice that received RTC#13 were able to hold on a wire for much longer then those that received DMSO only. (*: $p \le 0.005$; **: $p \le 0.001$).

Figure 20:
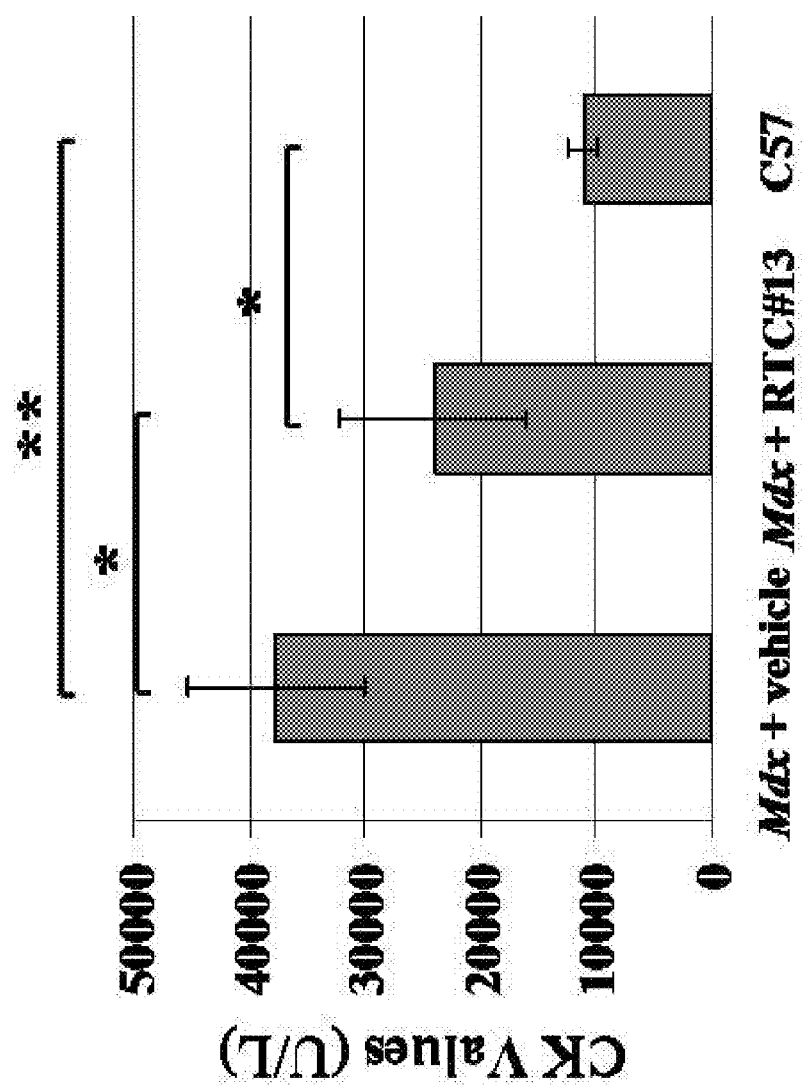
FIG. 20 shows the results of measurement of serum levels of creatine kinase (CK) in treated mdx mice (wth TAA) and controls (C57B16)

FIG. 20 shows measurement of serum levels of creatine kinase (CK), which was used as an index of ongoing muscle membrane instability in treated mdx mice compared with normal and mdx control mice. Data shows a significant difference in the CK levels was detected in all mice treated with RTC#13 and demonstrated the ability of the dystrophin protein being restored into muscle to slow down muscle degeneration. *, $p \le 0.02$; **, $p \le 0.003$.

Figure 21:
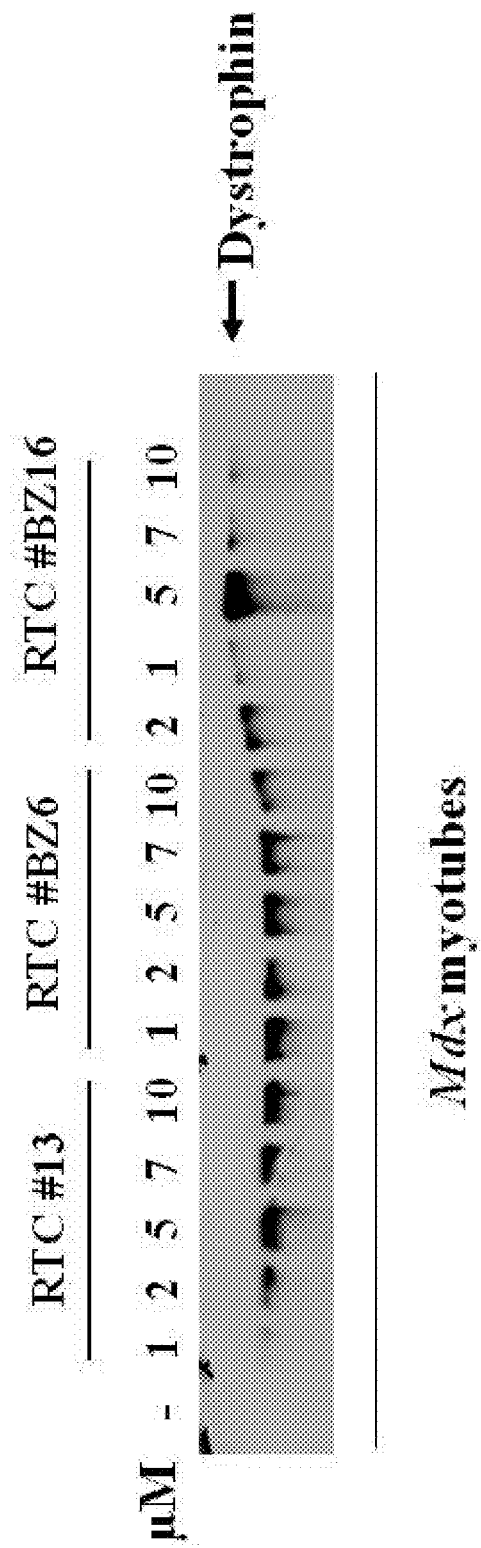
FIG. 21 shows the results of studies on the activity of RTC#13 and two of the analogs of RTC#13 termed RTC#BZ6 and RTC#BZ16 in myotube cells from mdx mice (with TAA).

In the experiments shown in FIG. 21, the activity of two of the analogs of RTC#13 termed RTC#BZ6 and RTC#BZ16 was investigated in myotube cultures isolated from mdx mice. Compounds were added to the differentiation media 24 hrs after induction of differentiation and replaced every 24 hrs by changing the media with new fresh media containing the appropriate concentration of RTC#13, RTC#BZ6 or RTC#BZ16. RTC#BZ6 showed levels of dystrophin expression comparable to that achieved using the parent compound RTC#13. RTC#BZ16 also showed to be effective although the highest level of readthrough activity was obtained at a concentration of 5 μM. No dystrophin expression was detected in cells treated with vehicle only at a final concentration of 10 μM.

Example 4

Synthesis of 2-Imino and 2-Thioxothiazolidin-4-One Derivatives

The synthesis and evaluation of several 2-imino and 2-thioxothiazolidin-4-one derivatives with regard to their ability to translate through the premature termination codons directly caused by nonsense mutations are described below.

We examined four structural changes in Compound 13 (also referred to as RTC13 or RTC1) (Formulae 13A-13D), namely: change in the heteroatom of the 2-carbonyl unit of the thiazolidin-4-one (A); variation of the aryl group on the furan ring (B); introduction of an alkyl group on the ring nitrogen on the thiazolidin-4-one (C); and introduction of different aryl groups as the central ring unit (D).

(Formulae 13A-13D)

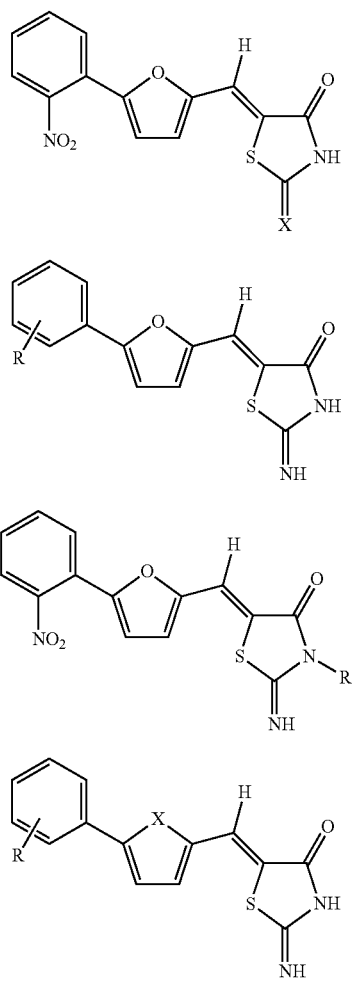

A

B

C

D

The syntheses of the compounds listed in Tables 2 and 3 are shown in Scheme 1. Coupling of the arylboronic acids 3 with commercially available 5-bromofurfural 4 afforded the 5-arylfurfurals 5 in good yields. Condensation of these compounds with any of the thiazolidinones 6abc furnished the desired products 7 in 50-95% yield. The two thiazolidinones 6ab were commercially available and the N-methyl analogue 6c was prepared in two steps from methyl isothiocyanate as shown. Also substitution of any of several heteroaryl aldehydes 8 for the 5-aryl-furfural allowed the synthesis of the heteroarylmethylene analogues 9. Most of the heteroaryl aldehydes 8 were commercially available while those that were not, e.g., the benzofuran-2-, indole-2-, 5-phenylthiophene-2-, and 5-(2-pyridyl)-furan-2-carboxaldehydes, were prepared by straightforward routes described below.

The syntheses of the compounds listed in Tables 2 and 3 are shown in Scheme 1. Note, Compounds such as 1 and 2 are generally available in chemical libraries and have been shown to have other interesting biological properties (see, e.g. (a) Fan, C.; et al., J. C. Bioorg. Med. Chem. 2010, 18, 2141-2151. and (b) Carter, P. H.; et al., Proc. Nat. Acad. Sci. U.S.A. 2001, 98, 11879-11884). Coupling of the arylboronic acids 3 with commercially available 5-bromofurfural 4 afforded the 5-arylfurfurals 5 in good yields. Condensation of these compounds with any of the thiazolidinones 6abc furnished the desired products 7 in 50-95% yield. The two thiazolidinones 6ab were commercially available and the N-methyl analogue 6c was prepared in two steps from methyl isothiocyanate as shown. Also substitution of any of several heteroaryl aldehydes 8 for the 5-aryl-furfural allowed the synthesis of the heteroarylmethylene analogues 9. Most of the heteroaryl aldehydes 8 were commercially available while those that were not, e.g., the benzofuran-2-, indole-2-, 5-phenylthiophene-2-, and 5-(2-pyridyl)-furan-2-carbox-aldehydes, were prepared by straightforward routes (see the Experimental section).

These two series, 7 and 9, were tested for readthrough activity using an assay in which the ATM protein kinase activity was measured using a flow cytometry-based ATMs1981 autophosphorylation assay (FC-ATM) (Nahas, S. A; et al., Clin. Chem. 2009, 55, 463-72). ATM kinase activity is demonstrated by the change in the fluorescence intensity before and after ionizing radiation (Delta-FI) (FIG. 3). An increased Delta-FI indicates the restoration of ATM kinase activity by a compound. Table 2 shows the data for the analogues 7 in which the groups X, R, and R' were varied. Several analogues showed reasonably good readthrough activity, with the 2-chlorophenyl and the 3-fluorophenyl 2-thioxo analogues 7m and 7q being the best of this group. Among the heteroaryl analogues 9, only the 2-benzofuranyl 2-thioxo analogue, 9g, gave positive results (Table 2).

Scheme 1

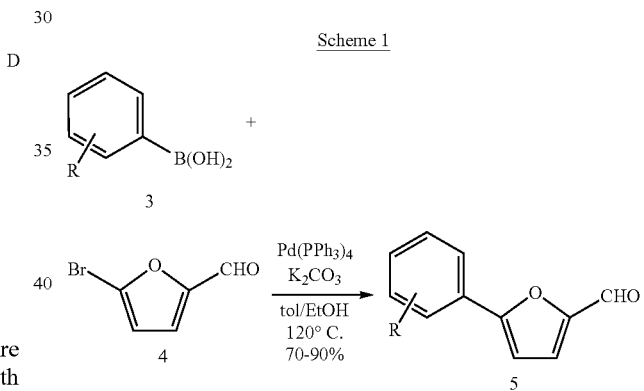

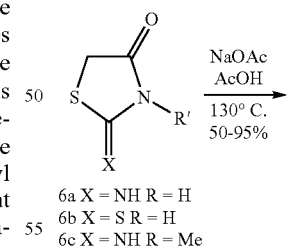

6a X = NH R = H
6b X = S R = H
6c X = NH R = Me

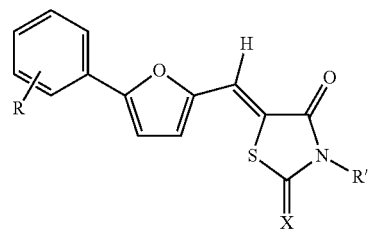

7

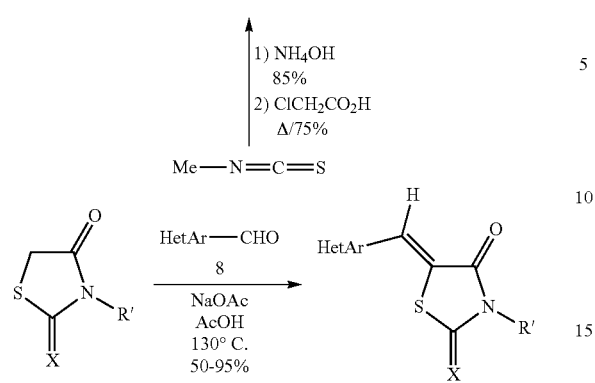

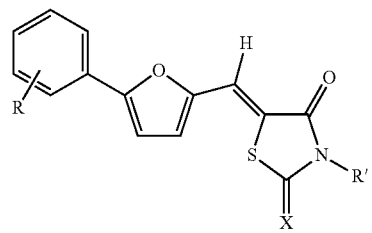

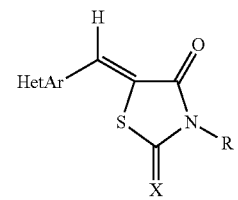

We believe that the mechanism of action of these novel tricyclic aromatic compounds might be similar to that of the aminoglycosides, which have been reported to exert their readthrough effects through an interaction with the ribosome (see, e.g., (a) Lynch, S. R.; et al., *Structure* 2003, 11, 43-53. (b) Linde, L.; Kerem, B. *Trends Genet.* 2008, 24, 552-563). In particular we wondered whether the 2-imino and 2-thioxothiazolidin-4-one units E might be bin-ding to nucleobases in the ribosome via hydrogen bonding (Scheme 2).

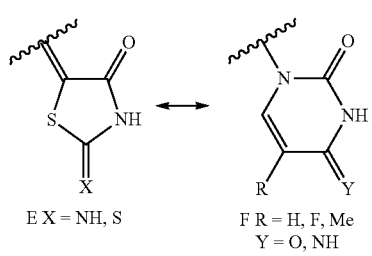

Consequently, we decided to substitute these thiazolidinone units with various pyrimidine bases, F, e.g., uracil, 5-fluoro- and 5-methyluracil (thymine), and cyto-sine units. The synthesis of these novel analogues was relatively easy and involved hydride reduction of the 5-arylfurfurals 5 to give the alcohols 10 in good yields (Scheme 3). Conversion of the alcohols into the bromides 11 with PBr$_3$ followed by reaction of the crude bromides 11 with an excess (10 eq) of the desired pyrimidine bases 12a-d gave good yields (57-88%) of the 1-pyrimidinylmethyl furans 13a-d. An analogous series of reactions, beginning with other aldehydes 5, permitted the formation of the pyrimidines 13e-i. Condensation of the 2-imino thiazolidin-4-one 6a with the aldehyde 13d gave the analogue 13j having both a pyrimidinone and the thiazolidinone imine. Finally, condensation of the pyrimidinecarboxaldehyde with 6a gave the novel bicyclic analogue 13k having just a pyrimidinone coupled to a thiazolidinone. The cytosine analogues were prepared by reaction of cytosine and 5-fluorocytosine 14ab with the nitro aldehyde 11 (R=2-NO$_2$) in the presence of cesium carbonate in DMF to give 15ab in 67% and 69% yield, respectively (Scheme 4).

TABLE 2

The evaluation of readthrough activity of compounds 7

| Entry | cmpd | X | R | R' | FC-ATM (Delta-FI, 30 μM) |
|---|---|---|---|---|---|
| 1 | RTC13 | NH | 2-NO$_2$ | H | 3.27 |
| 2 | 7a | NH | H | H | negative |
| 3 | 7b | S | 2-NO$_2$ | H | negative |
| 4 | 7c | NH | 2-NO$_2$ | Me | negative |
| 5 | 7d | NH | 2-CF$_3$ | H | negative |
| 6 | 7e | NH | 2-OMe | H | negative |
| 7 | 7f | NH | 2-Cl | H | negative |
| 8 | 7g | NH | 2-F | H | negative |
| 9 | 7h | NH | 3-MeO | H | 1.90 |
| 10 | 7i | NH | 3-Cl | H | 2.27 |
| 11 | 7j | NH | 3-F | H | negative |
| 12 | 7k | S | 2-CF$_3$ | H | negative |
| 13 | 7l | S | 2-MeO | H | negative |
| 14 | 7m | S | 2-Cl | H | 3.55 |
| 15 | 7n | S | 2-F | H | 2.86 |
| 16 | 7o | S | 3-OMe | H | 2.66 |
| 17 | 7p | S | 3-Cl | H | 2.86 |
| 18 | 7q | S | 3-F | H | 3.44 |

TABLE 3

The evaluation of readthrough activity of compounds 9

| Entry | cmpd | HetAr | R' | FC-ATM (Delta-FI, 30 μM) |
|---|---|---|---|---|
| 1 | 9a | 2-benzofuranyl | NH | negative |
| 2 | 9b | 2-indolyl | NH | negative |
| 3 | 9c | 3-indolyl | NH | negative |
| 4 | 9d | 5-(pyridin-2-yl)-furan-2-yl | NH | negative |
| 5 | 9e | 5-phenylthiophen-2-yl | NH | negative |
| 6 | 9f | furan-2-yl | NH | negative |
| 7 | 9g | 2-benzofuranyl | S | 3.50 |
| 8 | 9h | 2-indolyl | S | negative |
| 9 | 9i | 3-indolyl | S | negative |
| 10 | 9j | 5-(pyridin-2-yl)-furan-2-yl | S | negative |

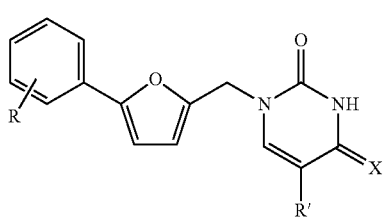

13-15

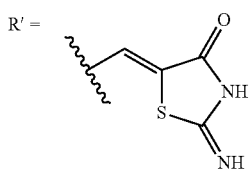

13j

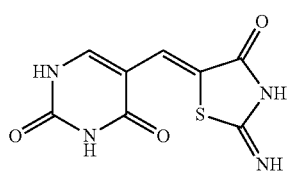

13k

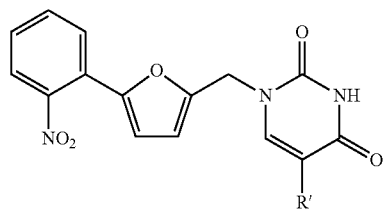

13a R' = H
13b R' = F
13c R' = Me
13d R' = CHO

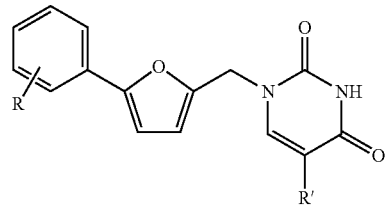

13e R = H R' = H
13f R = H R' = Me
13g R = 2-F R' = H
13h R = 2-F R' = Me
13i R = 3-Cl R' = H

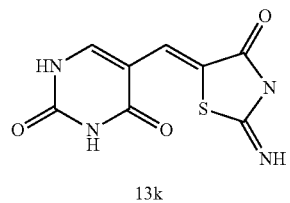

13k

13d →(6a, NaOAc, AcOH)

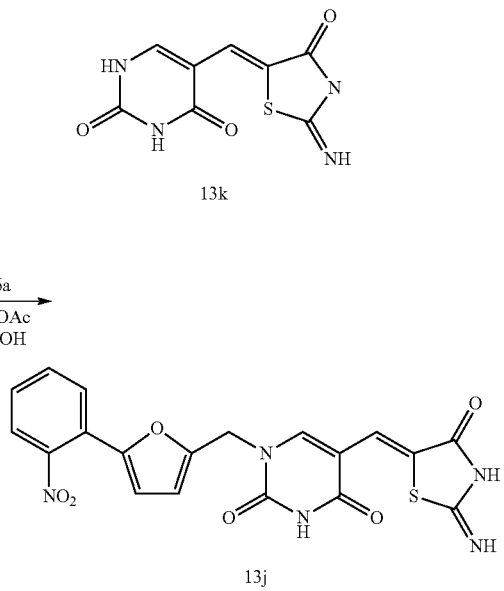

13j

TABLE 4

The evaluation of readthrough activity of compounds 13 and 15

| Entry | cmpd | R | R' | X | FC-ATM (Delta-FI, 30 μM) | IRIF-ATM (%) (30 μM) |
|---|---|---|---|---|---|---|
| 1 | 13a | 2-NO$_2$ | H | O | 4.94 | 10.67 |
| 2 | 13b | 2-NO$_2$ | F | O | 2.08 | 14.5 |
| 3 | 13c | 2-NO$_2$ | Me | O | negative | negative |
| 4 | 13d | 2-NO$_2$ | CHO | O | 2.24 | 16.0 |
| 5 | 13e | H | H | O | 3.42 | 9.4 |
| 6 | 13f | H | Me | O | 3.80 | 22.75 |
| 7 | 13g | 2-F | H | O | 5.43 | 20 |
| 8 | 13h | 2-F | Me | O | 6.16 | 9.6 |
| 9 | 13i | 3-Cl | H | O | 5.07 | 11.33 |
| 10 | 13j | 2-NO$_2$ | R'' | O | 2.42 | 18 |
| 11 | 13k | | | | 5.32 | 17 |
| 12 | 15a | 2-NO$_2$ | H | NH | negative | negative |
| 13 | 15b | 2-NO$_2$ | F | NH | negative | negative |

Scheme 3

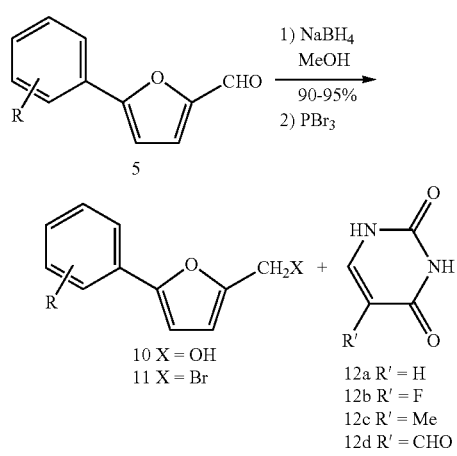

1) NaBH$_4$ MeOH 90-95%
2) PBr$_3$

5

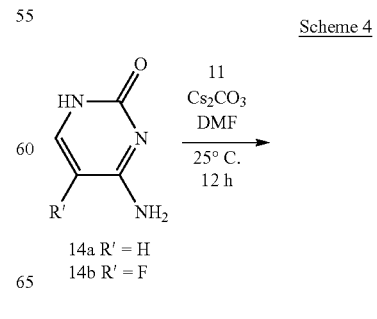

10 X = OH
11 X = Br

12a R' = H
12b R' = F
12c R' = Me
12d R' = CHO

K$_2$CO$_3$ DMF 45° C. 24 h 57-88% →

14a R' = H
14b R' = F

11 Cs$_2$CO$_3$ DMF 25° C. 12 h →

Scheme 4

-continued

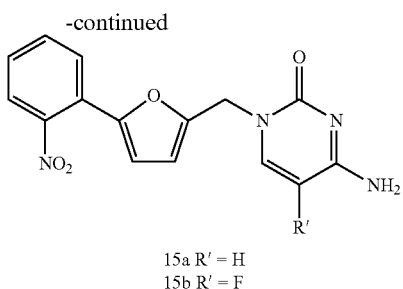

15a R' = H
15b R' = F

Figure 12:
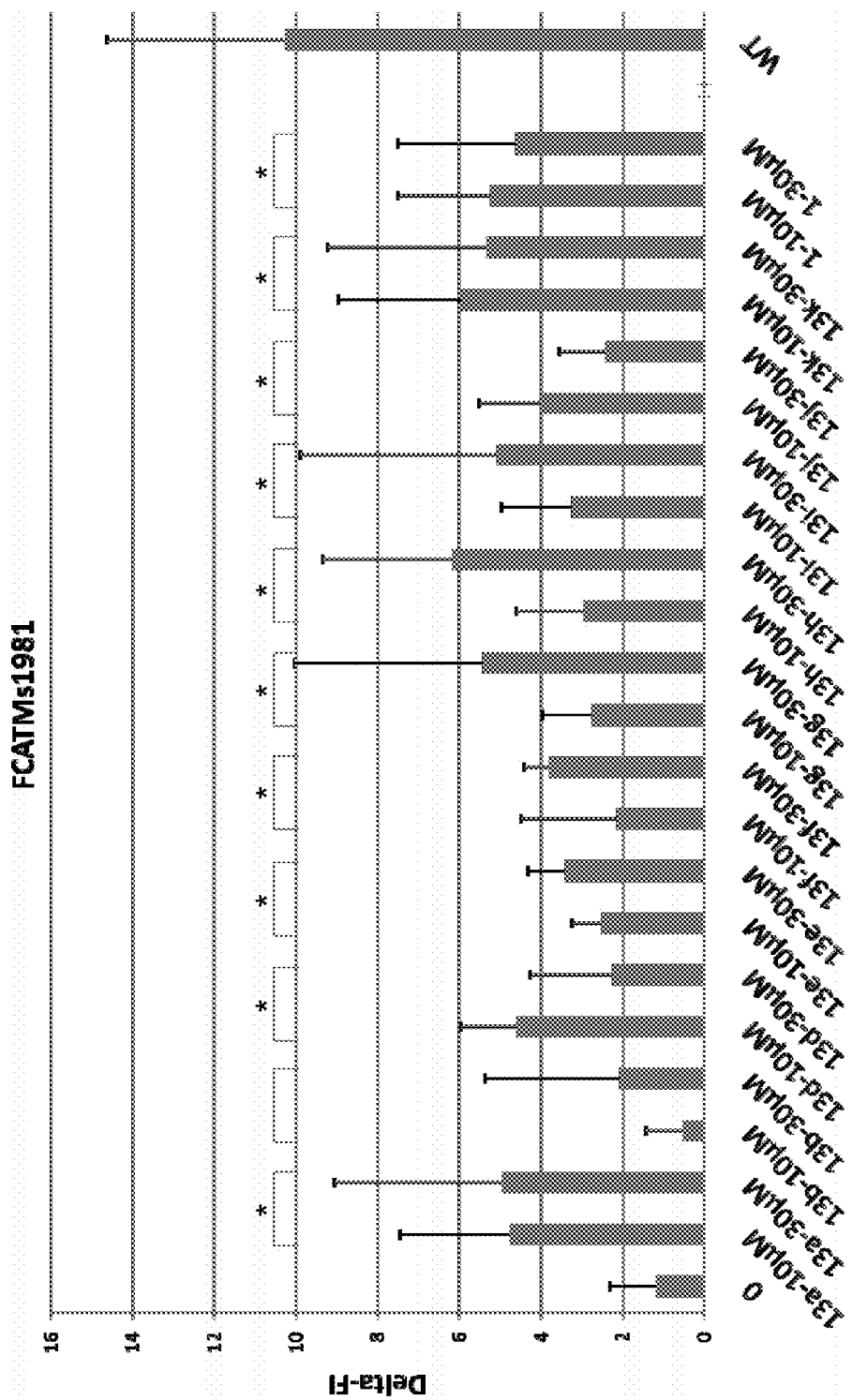
FIG. 12 shows the results of studies on FC-ATMs1981 autophosphorylation induced by RTC#13 (1) and derivatives in AT153LA cells (with TGA)

These two series, 13 and 15, were again tested for readthrough activity using the assay in which the ATM protein kinase activity was measured by functional flow cytometry (FC-ATM) (Table 4 and FIG. 12). A second assay, irradiation (1R)-induced ATMs1981 nuclear foci formation (IRIF-ATM), was also used to confirm the readthrough activity of these compounds (Table 4 and FIG. 13). Table 3 summarizes the data for the analogues 13 and 15 (at 30 µM), in which the groups R, R', and X were varied. More detailed data are reported in FIG. 5 (for FC-ATM assay), and in FIG. 6 (for IRIF-ATM assay). Interestingly, all of the pyrimidinedione analogues 13 (R'=H, F, Me, and CHO), with the exception of 13c, showed good activity while neither of the corresponding cytosine analogues, 15, had any. Remarkably, the simple bicyclic analogue 13k showed good activity in both assays. Thus, the pyrimidinedione unit serves as a good structural replacement for the 2-imino and 2-thioxo thiazolidin-4-one units.

Experimental

Materials were obtained from commercial suppliers and were used without purification. All the moisture sensitive reactions were conducted under argon atmosphere using oven-dried glassware and standard syringe/septa techniques. Most of reactions were monitored with a silica gel TLC plate under UV light followed by visualization with a p-anisaldehyde staining solution. $^1$H NMR spectra were measured at 400 MHz in proper solvents and data were reported as follows in ppm (δ) from the internal standard (TMS, 0.0 ppm): chemical shift (integration, multiplicity, coupling constant in Hz). The purity of the new compounds was assessed by several methods: high-field proton and carbon NMR (lack of significant impurities), $R_f$ values on TLC (lack of obvious impurities).

General Procedure for the Synthesis of 5-arylfuran-2-carboxaldehyde, for example, 5-(3-chlorophenyl)furan-2-carbaldehyde, 5f To a solution of 5-bromofuran-2-carboxaldehyde 4 (175.0 mg, 1.0 mmol) in a mixture of 10.0 mL of toluene and 4.0 mL ethanol was added 2-chlorophenylboronic acid 3f (156.4 mg, 1.0 mmol), tetrakis(triphenylphosphine)palladium (0) (33.0 mg, 0.028 mmol) at 25° C., and 10.0 mL of satd. potassium carbonate. The solution was refluxed for 3 h. After being cooled to 25° C., the solution was diluted with dichloromethane and washed with water. The combined organic layer was dried with sodium sulfate and the solvent was removed. The residue was purified by chromatography on silica gel eluting with hexane/ethyl acetate (5:2) to afford 171.0 mg (83%) of the compound 5f as a white solid. $^1$H NMR(CHCl$_3$) δ: 9.63 (1H, s), 7.93 (1H, dd, J=7.8, 2.1 Hz), 7.39 (1H, dd, J=7.8, 1.5 Hz), 7.26 (4H, m); $^{13}$C NMR (CHCl$_3$) δ: 177.46, 155.33, 151.52, 131.47, 130.93, 130.17, 129.07, 127.53, 127.19, 123.01, 113.21.

General Procedure of the Knoevenagel Condensation of Arylaldehydes with Various thiazoli-din-4-ones, for Example, Preparation of (Z)-2-imino-5-((5-phenylfuran-2-yl)methylene)thia-zolidin-4-one, 7a To a solution of the pseudothiohydantoin 6a (139 mg, 1.2 mmol), and sodium acetate (328 mg, 4.0 mmol) in acetic acid (5 ml) was added 5-phenyl-2-furaldehyde 5a (172 mg, 1.0 mmol) at 25° C. The solution was refluxed at 135° C. for 12 h. The precipitate was filtered and washed with water and diethyl ether. The filter cake was dried under high vacuum to afford 230 mg (85%) of compound 7a as an orange solid. $^1$H NMR (DMSO) δ: 9.33 (1H, s), 9.08 (1H, s), 7.78 (2H, d, J=7.2 Hz), 7.47 (1H, t, J=7.2 Hz), 7.40 (1H, s), 7.36 (1H, t, J=7.2 Hz), 7.20 (1H, d, J=3.6 Hz), 7.06 (1H, d, J=3.6 Hz); $^{13}$C NMR δ: 180.60, 176.56, 155.80, 149.77, 129.63, 129.58, 129.06, 124.27, 119.16, 115.94, 115.90, 109.84.

General Procedure of Suzuki Reaction of 5-formyl-2-furanboronic acid with heteroaromatic halides, for Example, Preparation of 5-(pyridin-2-yl)furan-2-carboxaldehyde, 8a In air, the 5-formyl-2-furanboronic acid (307 mg, 2.2 mmol), tris[dibenzylideneacetone]dipal-ladium (18.4 mg, 0.02 mmol), and tri(cyclohexyl)phosphine (13.4 mg, 0.048 mmol) were added to a 25 mL flask equipped with stir bar. The flask was evacuated and refilled with argon five times. Dioxane (5.3 mL), 2-bromopyridine (316 mg, 2.0 mmol), and aqueous 1.27 M K$_3$PO$_4$ (2.6 mL, 3.74 mmol) were added by syringe. The flask was sealed and heated in an oil bath at 100° C. for 12-18 h with vigorous stirring. The mixture was then filtered through a pad of silica gel and washed with ethyl acetate. The filtrate was concentrated under reduced pressure, and the aqueous residue was extracted three times with ethyl acetate. The combined extracts were dried over anhydrous MgSO$_4$, filtered, and concentrated. The residue was then purified by column chromatography eluting with ethyl acetate/dichloromethane (1:9) to afford 110 mg (29%) of compound 8a as a brown oil. $^1$H NMR (acetone-d$_6$) δ: 9.75 (1H, s), 8.69 (1H, d, J=5.0 Hz), 7.97 (2H, m), 7.60 (1H, d, J=3.5 Hz), 7.45 (1H, m), 7.35 (1H, d, J=4.0 Hz); $^{13}$C NMR (acetone-d$_6$) δ: 177.49, 157.90, 152.78, 149.99, 147.68, 137.08, 123.85, 123.31, 119.55, 110.49.

General Reduction of aldehyde with NaBH$_4$, for Example, (5-(2-nitrophenyl)furan-2-yl)methanol, 10a To a solution of 5-(2-nitrophenyl)-2-furfural 5a (1 g, 4.60 mmol) in ethanol (23 mL) was added NaBH$_4$ (209 mg, 5.52 mmol) at 0° C. in an ice bath. The solution was allowed to warm to 25° C. and stirred for 4 h. After the solvent was evaporated, the residue was diluted with ethyl acetate, washed with H$_2$O and brine. The combined organic layer was dried over Na$_2$SO$_4$, filtered and concentrated. The residue was purified by column chromatography eluting with hexane/ethyl acetate (2:1) to afford 957 mg (95%) of the alcohol 10a as a brown oil. $^1$H NMR(CHCl$_3$) δ: 7.65 (1H, dd, J=8.0, 1.5 Hz), 7.62 (1H, dd, J=8.0, 1.5 Hz), 7.50 (1H, td, J=8.0, 1.5 Hz), 7.34 (1H, td, J=8.0, 1.5 Hz), 6.56 (1H, d, J=3.5 Hz), 6.34 (1H, d, J=3.5 Hz), 4.56 (2H, s), 2.97 (1H, bs); $^{13}$C NMR (CHCl$_3$) δ: 155.52, 147.89, 147.13, 131.86, 129.70, 128.16, 123.82, 123.7, 110.44, 109.78, 57.06.

General Procedure for N-alkylation of pyrimidine Bases

1-((5-(2-Nitrophenyl)furan-2-yl)methyl)pyrimidine-2,4(1H,3H)-dione, 13a

To a solution of alcohol in dichloromethane at 0° C. was added neat PBr$_3$ in ice bath. The solution was allowed to warm to 25° C. and then stirred for 12 h. The reaction was quenched with ice and extracted with ethyl acetate. The combined organic layers were washed with H$_2$O, sat. NaHCO$_3$ and brine, and dried over anhydrous Na$_2$SO$_4$. After the solution was filtered and concentrated under reduced pressure, the crude compound was used for the subsequent alkylation without further purification. To a solution of 2-(bromomethyl)-5-(2-nitrophenyl)furan 11a (120 mg, 0.43 mmol) and uracil (476 mg, 4.3 mmol) in anhydrous DMF (2.0 mL) was added anhydrous potassium carbonate (235 mg, 1.7 mmol) at 25° C. The resulting solution was then heated at 50° C. for 8 h. After removal of DMF under reduced pressure, the residue was diluted with CHCl$_3$ and washed three times with water. The organic layer was dried over anhydrous MgSO$_4$ and concentrated under vacuum. The residue was purified by column chromatography eluting with ethyl acetate to afford 90 mg (68%) of the uracil 13a as a white solid. $^1$H NMR (DMSO) δ: 11.29 (1H, s), 7.82 (1H, d, J=8.1 Hz), 7.77 (1H, d, J=7.5 Hz), 7.68 (1H, t, J=7.2 Hz), 7.60 (1H, d, J=7.8 Hz), 7.52 (1H, t, J=8.1 Hz), 6.83 (1H, d, J=3.6 Hz), 6.53 (1H, d, J=3.3 Hz), 5.57 (1H, dd, J=7.8, 1.5 Hz), 4.88 (2H, s); $^{13}$C NMR (DMSO) δ: 164.08, 151.69, 151.07, 148.39, 147.33, 145.33, 132.91, 129.70, 129.04, 124.36, 122.84, 110.38, 111.18, 102.01, 43.74.

4-Amino-1-((5-(2-nitrophenyl)furan-2-yl)methyl)pyrimidin-2(1H)-one, 15a

To a solution of 2-(bromomethyl)-5-(2-nitrophenyl)furan 11a (230 mg, 0.815 mmol) and cytosine 14a (181 mg, 1.63 mmol) in anhydrous DMF (4 mL) was added cesium carbonate (398 mg, 1.22 mmol) at 25° C. The resulting solution was stirred for 12 h at the same temperature. After removal of the DMF under reduced pressure, the residue was diluted with CHCl$_3$ and washed three times with water. The organic layer was dried over anhydrous MgSO$_4$ and concentrated in a vacuum. The residue was purified by column chromatography eluting with ethyl acetate/methanol (20:1) to afford 170 mg (67%) of the cytosine 15a as a white solid. $^1$H NMR (DMSO) δ: 7.87 (1H, d, J=8.0 Hz), 7.82 (1H, d, J=7.5 Hz), 7.73 (1H, t, J=7.5 Hz), 7.58 (1H, d, J=7.0 Hz), 7.56 (1H, t, J=8.5 Hz), 7.16 (1H, s), 7.09 (1H, s), 6.86 (1H, d, J=3.5 Hz), 6.48 (1H, d, J=3.0 Hz), 5.72 (1H, d, J=7.5 Hz), 4.89 (2H, s); $^{13}$C NMR δ: 166.33, 155.63, 152.62, 147.82, 147.11, 145.59, 132.72, 129.41, 128.80, 124.16, 122.73, 110.07, 110.92, 94.21, 44.57.

N-Methylthiourea, 3-methyl-2-iminothiazolidin-4-one 6c, 2-benzofurancarboxaldehyde 8a, 1H-indole-2-carboxaldehyde 8b, were prepared following literature methods.

Spectroscopic Data

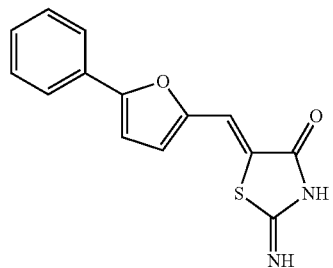

(Z)-2-imino-5-((5-phenylfuran-2-yl)methylene)thiazolidin-4-one

Compound 7a: $^1$H NMR (DMSO) δ: 9.33 (1H, s), 9.08 (1H, s), 7.78 (2H, d, J=7.2 Hz), 7.47 (1H, t, J=7.2 Hz), 7.40 (1H, s), 7.36 (1H, t, J=7.2 Hz), 7.20 (1H, d, J=3.6 Hz), 7.06 (1H, d, J=3.6 Hz); $^{13}$C NMR (DMSO) δ: 180.60, 176.56, 155.80, 149.77, 129.63, 129.58, 129.06, 124.27, 119.16, 115.94, 115.90, 109.84.

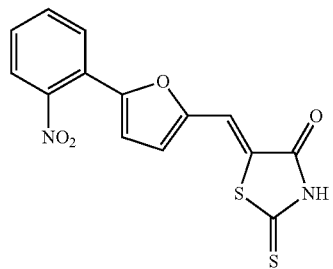

(Z)-5-((5-(2-nitrophenyl)furan-2-yl)methylene)-2-thioxothiazolidin-4-one

Compound 7b: $^1$H NMR (DMSO) δ: 13.69 (1H, bs), 7.97 (1H, d, J=7.2 Hz), 7.89 (1H, dd, J=1.2 Hz, 8.0 Hz), 7.79 (1H, td, J=0.8 Hz, 7.6 Hz), 7.65 (1H, td, J=1.2 Hz, 8.4 Hz), 7.45 (1H, s), 7.28 (1H, d, J=3.6 Hz), 7.18 (1H, d, J=4.0 Hz); $^{13}$C NMR (DMSO) δ: 196.73, 169.45, 153.07, 151.07, 147.42, 133.54, 130.95, 130.15, 125.17, 124.12, 122.27, 122.17, 117.10, 114.20.

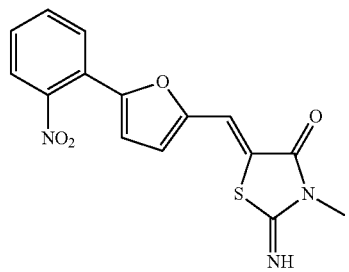 [SMILES: CN1C(=N)S/C(=C\c2ccc(-c3ccccc3[N+](=O)[O-])o2)C1=O]

(Z)-2-imino-3-methyl-5-((5-(2-nitrophenyl)furan-2-yl)methylene)thiazolidin-4-one Compound 7c: $^1$H NMR (CDCl$_3$) δ: 7.78 (2H, m), 7.65 (1H, td, J=1.5 Hz, 7.5 Hz), 7.49 (1H, td, J=1.2 Hz, 7.5 Hz), 7.47 (1H, s), 6.81 (1H, d, J=3.6 Hz), 6.78 (1H, d, J=3.9 Hz), 3.31 (3H, s); $^{13}$C NMR (CHCl$_3$) δ: 166.38, 157.38, 151.19, 151.07, 147.51, 132.33, 129.27, 129.08, 124.47, 123.19, 121.93, 117.93, 115.20, 112.83, 28.39.

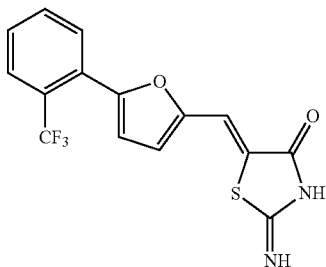 [SMILES: N=C1NC(=O)/C(=C/c2ccc(-c3ccccc3C(F)(F)F)o2)S1]

(Z)-2-imino-5-((5-(2-(trifluoromethyl)phenyl)furan-2-yl)methylene)thiazolidin-4-one Compound 7d: $^1$H NMR (DMSO) δ: 9.34 (1H, bs), 9.06 (1H, s), 7.87 (1H, d, J=7.2 Hz), 7.85 (1H, d, J=6.0 Hz), 7.77 (1H, t, J=7.6 Hz), 7.62 (1H, t, J=7.6 Hz), 7.40 (1H, t, J=7.6 Hz), 7.06 (1H, d, J=3.6 Hz), 6.95 (1H, d, J=3.6 Hz); $^{13}$C NMR (DMSO) δ: 180.52, 176.54, 152.41, 150.94, 133.38, 130.55, 129.90, 128.36, 128.26, 127.39 (q, J=5.7 Hz), 125.74 (q, J=30.5 Hz), 124.28 (d, J=271.8 Hz), 118.54, 115.73 (d, J=4.7 Hz), 114.14; $^{19}$F NMR (DMSO) δ: −58.94.

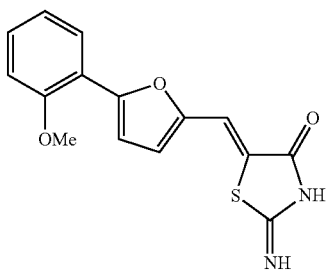 [SMILES: COc1ccccc1-c1ccc(/C=C2\SC(=N)NC2=O)o1]

(Z)-2-imino-5-((5-(2-methoxyphenyl)furan-2-yl)methylene)thiazolidin-4-one

Compound 7e: $^1$H NMR (DMSO) δ: 9.31 (1H, s), 9.07 (1H, s), 7.80 (1H, dd, J=1.5 Hz, 8.0 Hz), 7.40 (1H, s), 7.35 (1H, td, J=1.5 Hz, 8.5 Hz), 7.15 (1H, d, J=8.5 Hz), 7.10 (1H, d, J=3.5 Hz), 7.07 (1H, t, J=7.5 Hz), 7.05 (1H, d, J=3.5 Hz), 3.91 (3H, s).

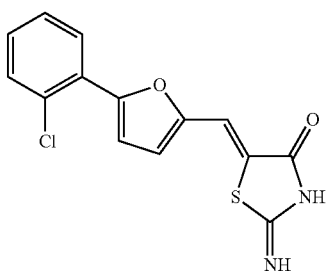 [SMILES: N=C1NC(=O)/C(=C/c2ccc(-c3ccccc3F)o2)S1]

(Z)-5-((5-(2-chlorophenyl)furan-2-yl)methylene)-2-iminothiazolidin-4-one

Compound 7f: $^1$H NMR (DMSO) δ: 9.36 (1H, bs), 9.11 (1H, s), 7.87 (1H, d, J=6.0 Hz), 7.57 (1H, d, J=7.0 Hz), 7.38 (4H, m), 7.08 (1H, s); $^{13}$C NMR (DMSO) δ: 180.37, 176.35, 151.89, 149.85, 131.41, 130.13, 129.87, 128.17, 128.04, 128.01, 127.81, 118.56, 115.53, 114.59.

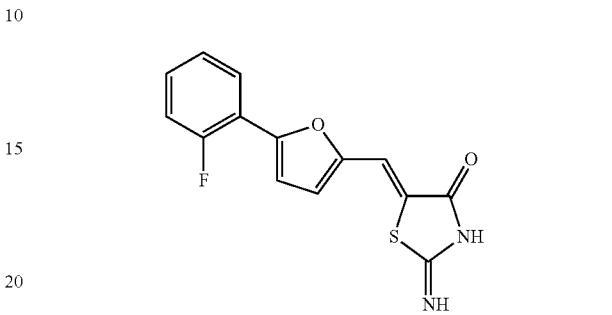

(Z)-5-((5-(2-fluorophenyl)furan-2-yl)methylene)-2-iminothiazolidin-4-one

Compound 7g: $^1$H NMR (DMSO) δ: 9.37 (1H, bs), 9.11 (1H, s), 7.80 (1H, t, J=7.5 Hz), 7.41 (1H, s), 7.38 (1H, t, J=7.0 Hz), 7.32 (2H, m), 7.07 (1H, d, J=3.5 Hz), 7.01 (1H, dd, J=3.5 Hz, 3.5 Hz); $^{13}$C NMR (DMSO) δ: 180.38, 176.38, 158.53 (d, J=249.2 Hz), 149.78, 149.76, 130.53 (d, 8.4 Hz), 127.98, 126.01, 125.40 (d, J=3.0 Hz), 118.82, 117.63 (d, J=11.7 Hz), 116.87 (d, J=20.8 Hz), 115.53, 113.72 (d, J=11.1 Hz); $^{19}$F NMR (DMSO) δ: −113.83.

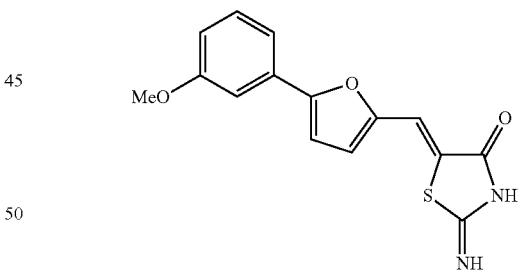

(Z)-2-imino-5-((5-(3-methoxyphenyl)furan-2-yl)methylene)thiazolidin-4-one

Compound 7h: $^1$H NMR (DMSO) δ: 9.33 (1H, s), 9.12 (1H, s), 7.35 (4H, m), 7.19 (1H, bs), 7.03 (1H, bs), 6.92 (1H, bs), 3.79 (3H, s); $^{13}$C NMR (DMSO) δ: 180.47, 176.42, 160.06, 155.53, 149.64, 130.75, 130.60, 127.17, 118.96, 116.60, 115.78, 114.21, 110.04, 109.82, 55.57.

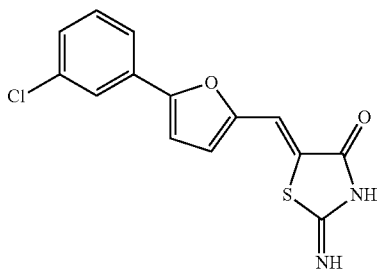 [SMILES: N=C1NC(=O)/C(=C/c2ccc(-c3cccc(Cl)c3)o2)S1]

(Z)-5-((5-(3-chlorophenyl)furan-2-yl)methylene)-2-iminothiazolidin-4-one

Compound 7i: $^1$H NMR (DMSO) δ: 9.25 (2H, bs), 7.80 (1H, d, J=1.5 Hz), 7.70 (1H, d, J=7.0 Hz), 7.48 (1H, t, J=8.0 Hz), 7.39 (1H, s), 7.38 (1H, d, J=8.0 Hz), 7.30 (1H, d, J=4.0 Hz), 7.05 (1H, d, J=3.5 Hz); $^{13}$C NMR (DMSO) δ: 180.37, 176.28, 154.01, 150.27, 134.35, 131.48, 131.31, 128.48, 127.80, 123.69, 122.55, 118.89, 115.56, 111.09.

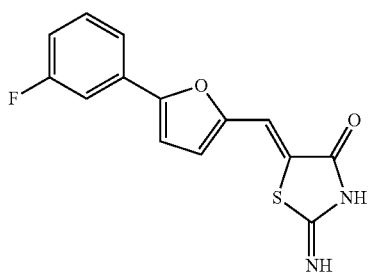 [SMILES: N=C1NC(=O)/C(=C/c2ccc(-c3cccc(F)c3)o2)S1]

(Z)-5-((5-(3-fluorophenyl)furan-2-yl)methylene)-2-iminothiazolidin-4-one

Compound 7j: $^1$H NMR (DMSO) δ: 9.36 (1H, bs), 9.11 (1H, s), 7.61 (1H, d, J=8.0 Hz), 7.56 (1H, d, J=8 Hz), 7.50 (1H, dt, J=4.5 Hz, 6.0 Hz), 7.40 (1H, s), 7.29 (1H, d, J=5.0 Hz), 7.18 (1H, td, J=2.4 Hz, 8.8 Hz), 7.06 (1H, d, J=5.0 Hz); $^{13}$C NMR (DMSO) δ: 180.40, 176.31, 162.93 (d, J=242.1 Hz), 154.22 (d, J=3.1 Hz), 150.16, 131.67 (d, J=14.0 Hz), 131.60 (d, J=14.5 Hz), 127.90, 120.20, 118.76, 115.48 (d, J=21.1 Hz), 115.45, 110.93, 110.69 (d, J=23.3 Hz); $^{19}$F NMR (DMSO) δ: −112.68.

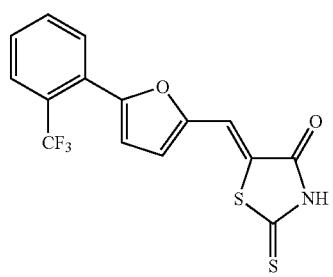

(Z)-2-thioxo-5-((5-(2-(trifluoromethyl)phenyl)furan-2-yl)methylene)thiazolidin-4-one Compound 7k: $^1$H NMR (DMSO) δ: 13.70 (1H, bs), 7.88 (1H, d, J=8.4 Hz), 7.83 (2H, m), 7.67 (1H, t, J=7.2 Hz), 7.48 (1H, s), 7.29 (1H, d, J=3.6 Hz), 7.02 (1H, d, J=3.6 Hz); $^{13}$C NMR (DMSO) δ: 196.58, 169.33, 154.48, 150.39, 133.39, 130.60, 130.14, 127.67, 127.31 (t, J=5.7 Hz), 125.65 (q, J=30.4 Hz), 124.09 (d, J=217.5 Hz), 123.00, 122.03, 117.34, 114.59; $^{19}$F NMR (DMSO) δ: −58.86

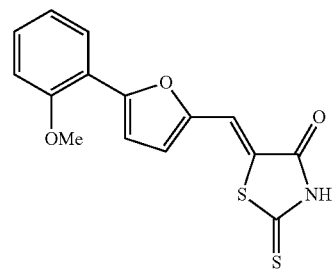 [SMILES: COc1ccccc1-c1ccc(/C=C2\SC(=S)NC2=O)o1]

(Z)-5-((5-(2-methoxyphenyl)furan-2-yl)methylene)-2-thioxothiazolidin-4-one

Compound 7l: $^1$H NMR (DMSO) δ: 13.60 (1H, bs), 7.71 (1H, dd, J=1.2 Hz, 8.0 Hz), 7.38 (1H, s), 7.34 (1H, td, J=1.6 Hz, 8.4 Hz), 7.19 (1H, d, J=4.0 Hz), 7.10 (3H, m), 3.88 (3H, s); $^{13}$C NMR (DMSO) δ: 196.52, 169.21, 156.34, 154.90, 148.23, 130.64, 125.95, 122.87, 121.80, 121.29, 117.47, 117.44, 114.29, 112.21, 59.91.

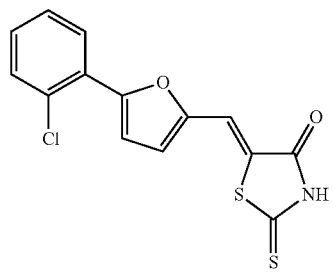 [SMILES: O=C1NC(=S)S/C1=C\c1ccc(-c2ccccc2Cl)o1]

(Z)-5-((5-(2-chlorophenyl)furan-2-yl)methylene)-2-thioxothiazolidin-4-one

Compound 7m: $^1$H NMR (DMSO) δ: 13.69 (1H, s), 7.83 (1H, d, J=8.0 Hz), 7.56 (1H, d, J=8.0 Hz), 7.53 (1H, t, J=7.5 Hz), 7.46 (1H, s), 7.39 (1H, t, J=7.0 Hz), 7.35 (1H, d, J=3.5 Hz), 7.27 (1H, d, J=4.0 Hz); $^{13}$C NMR (DMSO) δ: 196.51, 169.25, 154.02, 149.41, 131.45, 130.60, 130.11, 128.36, 128.32, 127.30, 123.37, 122.11, 117.26, 115.06.

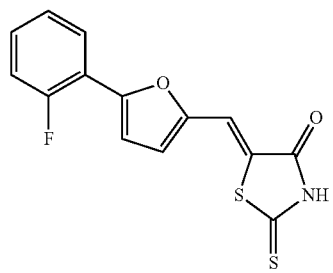 [SMILES: O=C1NC(=S)S/C1=C\c1ccc(-c2ccccc2F)o1]

(Z)-5-((5-(2-fluorophenyl)furan-2-yl)methylene)-2-thioxothiazolidin-4-one

Compound 7n: $^1$H NMR (DMSO) δ: 13.57 (1H, bs), 7.75 (1H, td, J=1.5 Hz, 7.5 Hz), 7.4 (1H, s), 7.35 (3H, m), 7.22 (1H, d, J=3.5 Hz), 7.02 (1H, dd, J=3.0 Hz, 3.5 Hz); $^{13}$C NMR (DMSO) δ: 196.74, 169.63, 158.70 (d, J=249.8 Hz), 151.93 (d, J=3.0 Hz), 149.37, 131.17 (d, J=8.5 Hz), 126.41, 125.68 (d, J=3.0 Hz), 123.46, 122.24, 117.11 (d, J=11.6 Hz), 116.99, 116.81 (d, J=20.8 Hz), 114.14 (d, J=11.2 Hz); $^{19}$F NMR (DMSO) δ: −113.47.

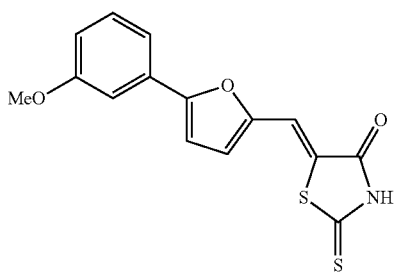 [SMILES: COc1cccc(-c2ccc(/C=C3\SC(=S)NC3=O)o2)c1]

(Z)-5-(5-(3-methoxyphenyl)furan-2-yl)methylene)-2-thioxothiazolidin-4-one

Compound 7o: $^1$H NMR (DMSO) δ: 13.63 (1H, bs), 7.41 (1H, s), 7.39 (1H, d, J=8.0 Hz), 7.34 (1H, d, J=7.5 Hz), 7.28 (1H, bs), 7.25 (1H, d, J=3.5 Hz), 7.22 (1H, d, J=3.5 Hz), 6.93 (1H, dd, J=2.0 Hz, 8.0 Hz), 3.78 (3H, s); $^{13}$C NMR (DMSO) δ: 196.56, 169.27, 160.03, 157.71, 149.31, 130.81, 130.17, 122.60, 122.34, 117.44, 116.99, 114.99, 110.68, 110.04, 55.51.

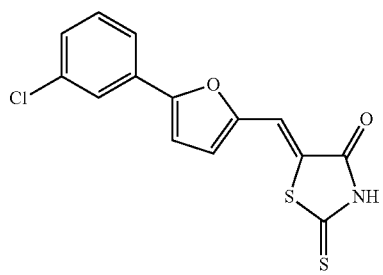 [SMILES: O=C1NC(=S)S/C1=C\c1ccc(-c2cccc(Cl)c2)o1]

(Z)-5-((5-(3-chlorophenyl)furan-2-yl)methylene)-2-thioxothiazolidin-4-one

Compound 7p: $^1$H NMR (DMSO) δ: 13.65 (1H, bs), 7.74 (1H, s), 7.65 (1H, d, J=7.5 Hz), 7.48 (1H, t, J=8.0 Hz), 7.38 (1H, s), 7.37 (1H, d, J=9.0 Hz), 7.31 (1H, d, J=4.0 Hz), 7.20 (1H, d, J=3.5 Hz); $^{13}$C NMR (DMSO) δ: 196.43, 169.20, 156.12, 149.80, 134.35, 131.44, 130.84, 128.96, 124.14, 122.91, 122.90, 122.41, 117.22, 111.54.

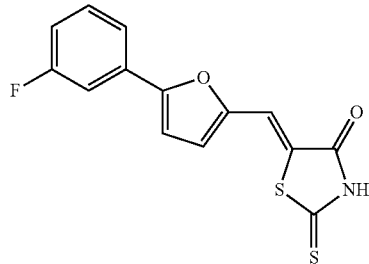 [SMILES: O=C1NC(=S)S/C1=C\c1ccc(-c2cccc(F)c2)o1]

(Z)-5-((5-(3-fluorophenyl)furan-2-yl)methylene)-2-thioxothiazolidin-4-one

Compound 7q: $^1$H NMR (DMSO) δ: 13.60 (1H, bs), 7.57 (3H, m), 7.42 (1H, s), 7.32 (1H, d, J=4.0 Hz), 7.24 (1H, d, J=3.6 Hz), 7.20 (1H, dd, J=2.8 Hz, 9.2 Hz); $^{13}$C NMR (DMSO) δ: 196.54, 169.33, 162.88 (d, J=242.3 Hz), 156.41 (d, J=3.2 Hz), 149.76, 131.87 (d, J=8.5 Hz), 131.10 (d, J=8.5 Hz), 122.97, 122.45, 120.57 (d, J=2.4 Hz), 117.27, 116.16 (d, J=21.1 Hz), 11.54, 111.21 (d, J=23.7 Hz); $^{19}$F NMR (DMSO) δ: −112.56.

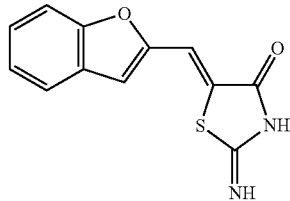

(Z)-5-(benzofuran-2-ylmethylene)-2-iminothiazolidin-4-one

Compound 9a: $^1$H NMR (DMSO) δ: 9.44 (1H, bs), 9.14 (1H, s), 7.67 (1H, d, J=7.5 Hz), 7.56 (1H, d, J=8.5 Hz), 7.51 (1H, s), 7.36 (1H, t, J=8.0 Hz), 7.33 (1H, s), 7.26 (1H, t, J=8.0 Hz); $^{13}$C NMR (DMSO) δ: 180.19, 176.57, 155.22, 151.90, 130.77, 128.53, 126.73, 124.11, 122.42, 116.25, 112.25, 111.50.

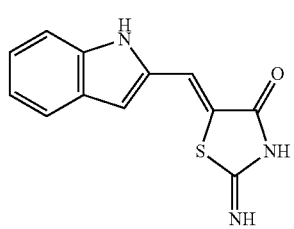 [SMILES: N=C1NC(=O)/C(=C/c2cc3ccccc3[nH]2)S1]

(Z)-5-((1H-indol-2-yl)methylene)-2-iminothiazolidin-4-one

Compound 9b: $^1$H NMR (DMSO) δ: 11.58 (1H, s), 9.31 (1H, bs), 7.66 (1H, d, J=8.0 Hz), 7.61 (1H, s), 7.43 (1H, d, J=8.0 Hz), 7.20 (1H, t, J=7.0 Hz), 7.07 (1H, t, J=8.0 Hz), 6.72 (1H, s); $^{13}$C NMR (DMSO) δ: 180.47, 175.15, 137.41, 133.69, 129.97, 128.70, 123.74, 121.28, 120.34, 119.42, 111.92, 104.27.

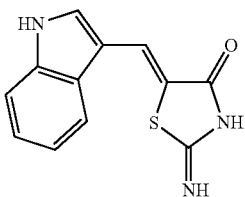 [SMILES: N=C1NC(=O)/C(=C/c2c[nH]c3ccccc23)S1]

(Z)-5-((1H-indol-3-yl)methylene)-2-iminothiazolidin-4-one

Compound 9c: $^1$H NMR (DMSO) δ: 11.8 (1H, s), 9.14 (1H, bs), 8.92 (1H, s), 7.80 (1H, s), 7.80 (1H, d, J=7.0 Hz), 7.58 (1H, d, J=2.5 Hz), 7.45 (1H, d, J=8.0 Hz), 7.18 (1H, t, J=7.0 Hz), 7.12 (1H, t, J=7.5 Hz); $^{13}$C NMR (DMSO) δ: 180.90, 174.71, 136.60, 127.26, 127.04, 123.73, 123.02, 121.46, 120.84, 118.59, 112.56, 111.44.

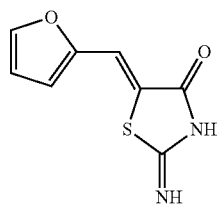 [SMILES: N=C1NC(=O)/C(=C/c2ccco2)S1]

(Z)-5-(furan-2-ylmethylene)-2-iminothiazolidin-4-one

Compound 9f: $^1$H NMR (DMSO) δ: 9.30 (1H, bs), 9.03 (1H, s), 7.92 (1H, d, J=1.2 Hz), 7.35 (1H, s), 6.89 (1H, d, J=3.2 Hz), 6.65 (1H, dd, J=3.2 Hz, 1.6 Hz); $^{13}$C NMR (DMSO) δ: 180.56, 175.57, 150.17, 146.50, 127.35, 116.54, 116.31, 113.65.

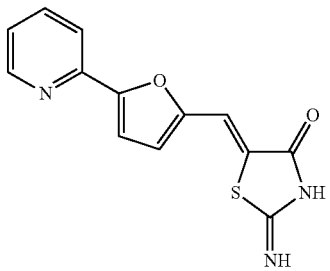

(Z)-2-imino-5-((5-(pyridin-2-yl)furan-2-yl)methylene)thiazolidin-4-one

Compound 9d: $^1$H NMR (DMSO) δ: 9.38 (1H, bs), 9.11 (1H, s), 8.61 (1H, d, J=4.0 Hz), 7.91 (1H, t, J=8.0 Hz), 7.74 (1H, d, J=8.0 Hz), 7.43 (1H, s), 7.33 (1H, t, J=6 Hz), 7.27 (1H, d, J=3.5 Hz), 7.08 (1H, d, J=3.0 Hz); $^{13}$C NMR (DMSO) δ: 180.33, 176.39, 155.26, 150.76, 150.42, 147.89, 137.58, 128.33, 123.46, 118.87, 118.70, 115.64, 112.24.

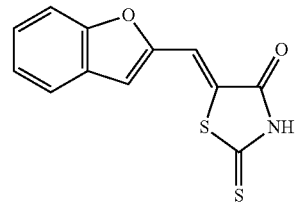 [SMILES: O=C1NC(=S)S/C1=C\c1cc2ccccc2o1]

(Z)-5-(benzofuran-2-ylmethylene)-2-thioxothiazolidin-4-one

Compound 9g: $^1$H NMR (DMSO) δ: 13.75 (1H, bs), 7.71 (1H, d, J=8.0 Hz), 7.64 (1H, d, J=8.0 Hz), 7.56 (1H, s), 7.51 (1H, s), 7.41 (1H, t, J=8.0 Hz), 7.27 (1H, t, J=8.0 Hz); $^{13}$C NMR (DMSO) δ: 196.93, 169.23, 155.99, 151.27, 128.24, 127.82, 126.38, 124.43, 122.96, 118.10, 115.65, 111.91.

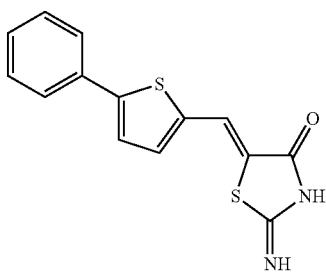

(Z)-2-imino-5-((5-phenylthiophen-2-yl)methylene)thiazolidin-4-one

Compound 9e: $^1$H NMR (DMSO) δ: 9.48 (1H, bs), 9.12 (1H, s), 7.77 (1H, s), 7.77 (2H, d, J=8.0 Hz), 7.62 (1H, d, J=4.0 Hz), 7.54 (1H, d, J=4.0 Hz), 7.41 (2H, t, J=8.0 Hz), 7.33 (1H, t, J=7.2 Hz); $^{13}$C NMR (DMSO) δ: 180.45, 174.82, 147.94, 138.62, 134.75, 133.35, 129.78, 129.11, 128.10, 125.97, 125.78, 122.52.

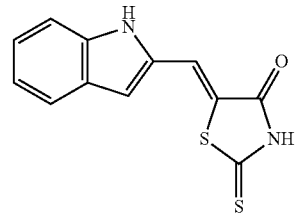 [SMILES: O=C1NC(=S)S/C1=C\c1cc2ccccc2[nH]1]

(Z)-5-((1H-indol-2-yl)methylene)-2-thioxothiazolidin-4-one

Compound 9h: $^1$H NMR (DMSO) δ: 13.73 (1H, bs), 11.65 (1H, s), 7.63 (1H, d, J=8.0 Hz), 7.56 (1H, s), 7.41 (1H, d, J=8.5 Hz), 7.20 (1H, t, J=8.0 Hz), 7.04 (1H, d, J=7.5 Hz), 6.80 (1H, s); $^{13}$C NMR (DMSO) δ: 195.35, 169.41, 138.21, 132.40, 128.87, 125.02, 123.87, 121.92, 121.76, 120.85, 112.31, 107.78.

61

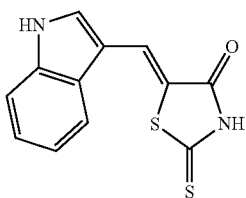 [SMILES: O=C1NC(=S)S/C1=C\c1c[nH]c2ccccc12]

(Z)-5-((1H-indol-3-yl)methylene)-2-thioxothiazolidin-4-one

Compound 9i: $^1$H NMR (DMSO) δ: 13.51 (1H, s), 12.26 (1H, s), 7.89 (1H, s), 7.87 (1H, d, J=8.0 Hz), 7.77 (1H, s), 7.46 (1H, t, J=8.0 Hz), 7.22 (1H, t, J=8.0 Hz), 7.17 (1H, t, J=8.0 Hz); $^{13}$C NMR (DMSO) δ: 194.94, 169.43, 136.71, 130.35, 127.08, 125.10, 123.59, 121.70, 118.77, 118.20, 112.84, 111.22.

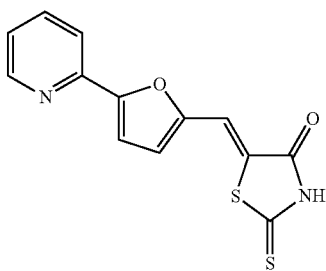 [SMILES: O=C1NC(=S)S/C1=C\c1ccc(-c2ccccn2)o1]

(Z)-5-((5-(pyridin-2-yl)furan-2-yl)methylene)-2-thioxothiazolidin-4-one

Compound 9j: $^1$H NMR (DMSO) δ: 13.70 (1H, bs), 11.92 (1H, bs), 8.62 (1H, dd, J=0.9 Hz, 3.9 Hz), 7.97 (1H, td, J=1.8 Hz, 7.8 Hz), 7.77 (1H, d, J=8.1 Hz), 7.48 (1H, s), 7.35 (1H, m), 7.31 (1H, d, J=3.6 Hz), 7.28 (1H, d, J=3.9 Hz); $^{13}$C NMR (DMSO) δ: 196.90, 169.57, 157.40, 150.64, 150.50, 147.52, 138.11, 124.07, 123.83, 122.37, 119.72, 117.47, 112.83.

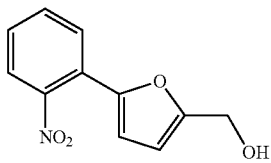 [SMILES: O=[N+]([O-])c1ccccc1-c1ccc(CO)o1]

(5-(2-nitrophenyl)furan-2-yl)methanol

Compound 10a: $^1$H NMR(CHCl$_3$) δ: 7.65 (1H, dd, J=8.0, 1.5 Hz), 7.62 (1H, dd, J=8.0, 1.5 Hz), 7.50 (1H, td, J=8.0, 1.5 Hz), 7.34 (1H, td, J=8.0, 1.5 Hz), 6.56 (1H, d, J=3.5 Hz), 6.34 (1H, d, J=3.5 Hz), 4.56 (2H, s), 2.97 (1H, bs); $^{13}$C NMR (CHCl$_3$) δ: 155.52, 147.89, 147.13, 131.86, 129.70, 128.16, 123.82, 123.7, 110.44, 109.78, 57.06.

62

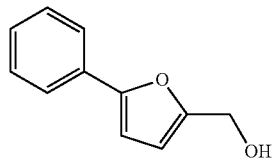 [SMILES: OCc1ccc(-c2ccccc2)o1]

(5-phenylfuran-2-yl)methanol

Compound 10e: $^1$H NMR(CHCl$_3$) δ: 7.67 (2H, m), 7.38 (2H, td, J=0.9 Hz, 8.4 Hz), 7.26 (1H, tt, J=1.5 Hz, 7.2 Hz), 6.59 (1H, d, J=3.3 Hz), 6.36 (1H, d, J=3.3 Hz), 4.65 (2H, s), 2.23 (1H, bs); $^{13}$C NMR(CHCl$_3$) δ: 154.03, 153.63, 130.72, 128.70, 127.50, 123.84, 109.99, 105.75, 57.64.

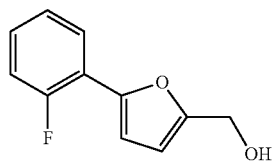 [SMILES: OCc1ccc(-c2ccccc2F)o1]

(5-(2-fluorophenyl)furan-2-yl)methanol

Compound 10g: $^1$H NMR (CHCl$_3$) δ: 7.83 (1H, td, J=1.8 Hz, 7.8 Hz), 7.17 (3H, m), 6.79 (1H, dd, J=3.3 Hz, 3.6 Hz), 6.41 (1H, d, J=3.3 Hz), 4.67 (2H, s), 2.03 (1H, bs); $^{13}$C NMR (CHCl$_3$) δ: 158.69 (d, J=248.9 Hz), 153.49, 148.10 (d, J=2.9 Hz), 128.40 (d, J=8.3 Hz), 126.05 (d, J=3.1 Hz), 124.28 (d, J=3.4 Hz), 118.92 (d, J=11.8 Hz), 115.92 (d, J=21.3 Hz), 110.91 (d, J=11.8 Hz), 110.24, 57.60.

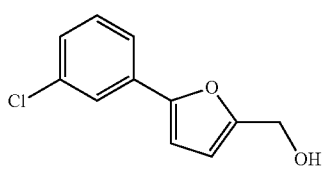 [SMILES: OCc1ccc(-c2cccc(Cl)c2)o1]

(5-(3-chlorophenyl)furan-2-yl)methanol

Compound 10i: $^1$H NMR (CHCl$_3$) δ: 7.63 (1H, t, J=1.5 Hz), 7.51 (1H, dt, J=1.5 Hz, 7.5 Hz), 7.28 (1H, t, J=7.8 Hz), 7.21 (1H, tt, J=1.8 Hz, 8.1 Hz), 6.59 (1H, d, J=3.3 Hz), 6.35 (1H, d, J=3.3 Hz), 4.64 (2H, s), 2.40 (1H, bs); $^{13}$C NMR (CHCl$_3$) δ: 154.20, 152.48, 134.72, 132.32, 129.97, 127.34, 123.78, 121.83, 110.06, 106.84, 57.52.

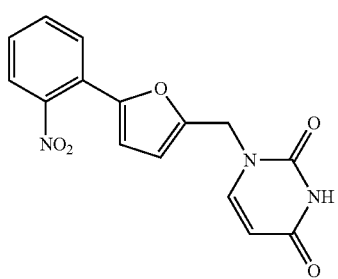 [SMILES: O=c1ccn(Cc2ccc(-c3ccccc3[N+](=O)[O-])o2)c(=O)[nH]1]

1-((5-(2-nitrophenyl)furan-2-yl)methyl)pyrimidine-2,4(1H,3H)-dione

Compound 13a: $^1$H NMR (DMSO) δ: 11.29 (1H, s), 7.82 (1H, d, J=8.1 Hz), 7.77 (1H, d, J=7.5 Hz), 7.68 (1H, t, J=7.2 Hz), 7.60 (1H, d, J=7.8 Hz), 7.52 (1H, t, J=8.1 Hz), 6.83 (1H, d, J=3.6 Hz), 6.53 (1H, d, J=3.3 Hz), 5.57 (1H, dd, J=7.8, 1.5 Hz), 4.88 (2H, s); $^{13}$C NMR (DMSO) δ: 164.08, 151.69, 151.07, 148.39, 147.33, 145.33, 132.91, 129.70, 129.04, 124.36, 122.84, 110.38, 111.18, 102.01, 43.74.

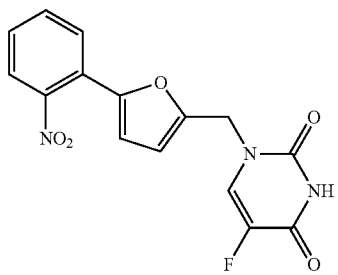 [SMILES: Cc1cn(Cc2ccc(-c3ccccc3[N+](=O)[O-])o2)c(=O)[nH]c1=O]

5-fluoro-1-((5-(2-nitrophenyl)furan-2-yl)methyl)pyrimidine-2,4(1H,3H)-dione

Compound 13b: $^1$H NMR (MeOH) δ: 7.77 (1H, d, J=6.0 Hz), 7.72 (1H, d, J=8.0 Hz), 7.70 (1H, d, J=9.0 Hz), 7.62 (1H, td, J=1.5 Hz, 9.0 Hz), 7.48 (1H, td, J=1.5 Hz, 9.0 Hz), 6.72 (1H, d, J=3.5 Hz), 6.55 (1H, d, J=3.0 Hz), 4.90 (2H, s); $^{13}$C NMR (MeOH) δ: 156.79 (d, J=25.9 Hz), 148.50, 148.10, 147.66, 146.02, 138.88 (d, J=231.8 Hz), 130.14, 127.35, 127.09, 126.79, 121.89, 121.42, 109.54, 108.25, 41.97; $^{19}$F NMR (MeOH) δ: 162.24.

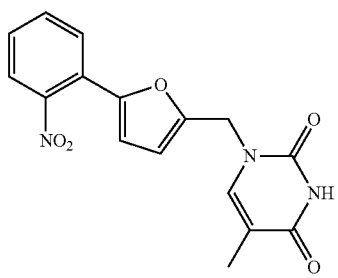

5-methyl-1-((5-(2-nitrophenyl)furan-2-ylmethyl)pyrimidine-2,4(1H,3H)-dione

Compound 13c: $^1$H NMR (DMSO) δ: 11.34 (1H, s), 7.87 (1H, d, J=8.0 Hz), 7.82 (1H, d, J=8.0 Hz), 7.73 (1H, t, J=7.5 Hz), 7.58 (1H, t, J=8.0 Hz), 7.49 (1H, s), 6.91 (1H, d, J=3.5 Hz), 6.58 (1H, d, 3.0 Hz), 4.89 (2H, s), 1.81 (3H, s); $^{13}$C NMR (DMSO) δ: 164.55, 151.66, 150.89, 148.30, 147.20, 140.86, 132.72, 129.53, 128.84, 124.19, 122.64, 111.14, 111.01, 109.51, 43.26, 12.35.

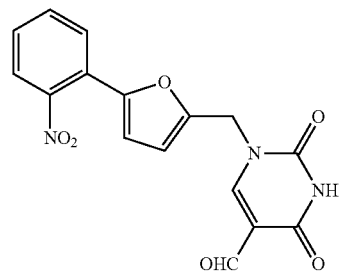 [SMILES: O=Cc1cn(Cc2ccc(-c3ccccc3[N+](=O)[O-])o2)c(=O)[nH]c1=O]

1-((5-(2-nitrophenyl)furan-2-yl)methyl)-2,4-dioxo-1,2,3,4-tetrahydropyrimidine-5-carbaldehyde Compound 13d: $^1$H NMR (DMSO) δ: 11.80 (1H, s), 9.76 (1H, d, J=0.5 Hz), 8.47 (1H, s), 7.80 (1H, d, J=8.0 Hz), 7.77 (1H, d, J=8.0 Hz), 7.68 (1H, t, J=7.5 Hz), 7.53 (1H, t, J=7.5 Hz), 6.86 (1H, d, J=3.0 Hz), 6.61 (1H, d, J=3.5 Hz), 5.05 (2H, s); $^{13}$C NMR (DMSO) δ: 186.52, 162.45, 151.54, 150.66, 150.01, 148.45, 147.22, 132.78, 129.61, 128.87, 124.24, 122.64, 111.58, 111.13, 111.07, 44.81.

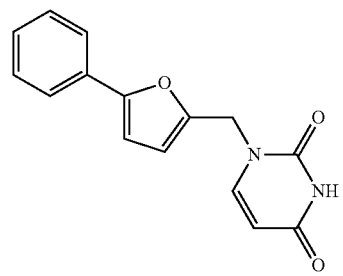 [SMILES: O=c1ccn(Cc2ccc(-c3ccccc3)o2)c(=O)[nH]1]

1-((5-phenylfuran-2-yl)methyl)pyrimidine-2,4(1H,3H)-dione

Compound 13e: $^1$H NMR (DMSO) δ: 11.32 (1H, s), 7.74 (1H, d, J=8.0 Hz), 7.62 (2H, d, J=7.5 Hz), 7.38 (2H, t, J=7.5 Hz), 7.26 (1H, t, J=7.0 Hz), 6.87 (1H, d, J=2.0 Hz), 6.48 (1H, s), 5.60 (1H, d, J=8.0 Hz), 4.92 (2H, s); $^{13}$C NMR (DMSO) δ: 163.94, 153.31, 151.02, 149.75, 145.45, 130.26, 129.23, 127.98, 123.66, 111.39, 106.95, 101.82, 43.75.

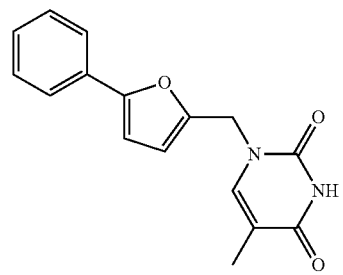 [SMILES: Cc1cn(Cc2ccc(-c3ccccc3)o2)c(=O)[nH]c1=O]

5-methyl-1-((5-phenylfuran-2-yl)methyl)pyrimidine-2,4(1H,3H)-dione

Compound 13f: $^1$H NMR (DMSO) δ: 11.31 (1H, s), 7.63 (1H, d, J=8.5 Hz), 7.62 (1H, d, J=7.5 Hz), 7.60 (1H, s), 7.38 (2H, t, J=7.5 Hz), 7.26 (1H, t, J=7.0 Hz), 6.86 (1H, d, J=3.0 Hz), 6.47 (1H, d, J=3.0 Hz), 4.88 (2H, s), 1.73 (3H, s); $^{13}$C NMR (DMSO) δ: 164.52, 153.25, 151.02, 149.99, 141.02, 130.29, 129.23, 127.95, 123.66, 111.31, 109.47, 106.96, 43.55, 12.29.

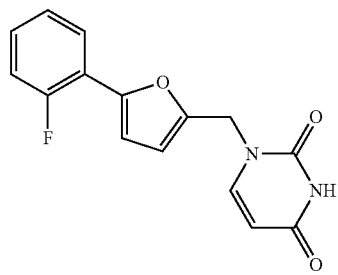 [SMILES: O=c1ccn(Cc2ccc(-c3ccccc3F)o2)c(=O)[nH]1]

1-((5-(2-fluorophenyl)furan-2-yl)methyl)pyrimidine-2,4(1H,3H)-dione

Compound 13g: $^1$H NMR (DMSO) δ: 11.33 (1H, s), 7.75 (1H, d, J=8.0 Hz), 7.71 (1H, t, J=8.0 Hz), 7.28 (3H, m), 6.77 (1H, dd, J=3.5 Hz, 3.0 Hz), 6.53 (1H, d, J=3.0 Hz), 5.60 (1H, d, J=8.0 Hz), 4.94 (2H, s); $^{13}$C NMR (DMSO) δ: 163.94, 158.08 (d, J=247.7 Hz), 151.02, 150.09, 147.36, 145.47, 129.62 (d, J=8.3 Hz), 126.02 (d, J=2.5 Hz), 125.29 (d, J=3.1 Hz), 118.17 (d, J=12 Hz), 116.50 (d, J=20.9 Hz), 111.48, 111.34 (d, J=10.7 Hz), 101.86, 43.71; $^{19}$F NMR (DMSO) δ: −115.12.

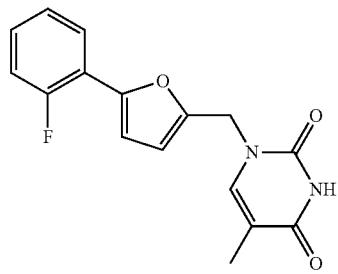 [SMILES: Cc1cn(Cc2ccc(-c3ccccc3F)o2)c(=O)[nH]c1=O]

1-((5-(2-fluorophenyl)furan-2-yl)methyl)-5-methylpyrimidine-2,4(1H,3H)-dione Compound 13h: $^1$H NMR (DMSO) δ: 11.32 (1H, s), 7.70 (1H, td, J=1.5 Hz, 7.8 Hz), 7.61 (1H, s), 7.29 (3H, m), 6.77 (1H, t, J=3.5 Hz), 6.52 (1H, d, J=3.5 Hz), 4.90 (2H, s), 1.73 (3H, s); $^{13}$C NMR (DMSO) δ: 164.52, 158.08 (d, J=247.6 Hz), 151.02, 150.34, 147.31 (d, J=2.7 Hz), 141.03, 129.59 (d, J=8.25 Hz), 126.03 (d, J=2.75 Hz), 125.30 (d, J=3.25 Hz), 118.19 (d, J=11.8 Hz), 116.55 (d, J=21.0 Hz), 111.39, 111.30, 109.51, 43.50, 12.29; $^{19}$F NMR (DMSO) δ: −115.12.

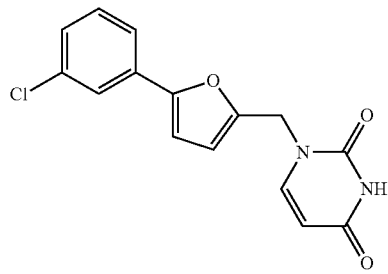 [SMILES: O=c1ccn(Cc2ccc(-c3cccc(Cl)c3)o2)c(=O)[nH]1]

1-((5-(3-chlorophenyl)furan-2-yl)methyl)pyrimidine-2,4(1H,3H)-dione

Compound 13i: $^1$H NMR (MeOH) δ: 7.70 (1H, d, J=8.0 Hz), 7.65 (1H, t, J=2.0 Hz), 7.57 (1H, dt, J=1.0 Hz, 8.0 Hz), 7.35 (1H, t, J=8.0 Hz), 7.23 (1H, ddd, J=1.0 Hz, 2.0 Hz, 8.0 Hz), 6.79 (1H, d, J=3.5 Hz), 6.51 (1H, d, J=3.5 Hz), 5.68 (1H, d, J=8.0 Hz), 4.97 (2H, s); $^{13}$C NMR (MeOH) δ: 164.99, 152.64, 151.02, 149.23, 144.94, 134.33, 132.00, 129.88, 126.98, 122.95, 121.49, 111.29, 106.81, 101.24, 43.42.

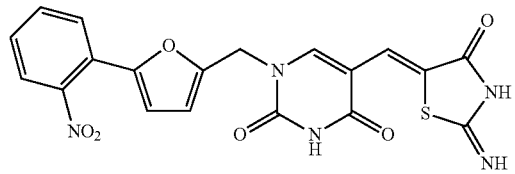 [SMILES: N=C1NC(=O)/C(=C/c2cn(Cc3ccc(-c4ccccc4[N+](=O)[O-])o3)c(=O)[nH]c2=O)S1]

(Z)-5-((2-imino-4-oxothiazolidin-5-ylidene)methyl)-1-((5-(2-nitrophenyl)furan-2-yl)methyl)pyrimidine-2,4(1H,3H)-dione Compound 13j: $^1$H NMR (DMSO) δ: 11.74 (1H, s), 9.15 (1H, bs), 8.91 (1H, s), 7.98 (1H, s), 7.81 (1H, d, J=8.0 Hz), 7.78 (1H, dd, J=1.0 Hz, 8.0 Hz), 7.67 (1H, td, J=1.0 Hz, 9.0 Hz), 7.52 (1H, td, J=1.0 Hz, 9.0 Hz), 7.28 (1H, s), 6.86 (1H, d, J=3.5 Hz), 6.65 (1H, d, J=3.0 Hz), 4.99 (2H, s); $^{13}$C NMR (DMSO) δ: 180.73, 176.79, 162.50, 150.95, 149.80, 148.43, 147.22, 147.00, 132.74, 129.59, 128.85, 127.66, 124.21, 122.62, 122.19, 111.49, 111.06, 108.92, 44.39.

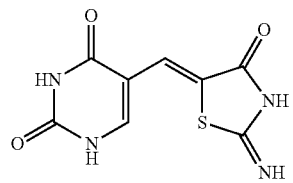 [SMILES: N=C1NC(=O)/C(=C/c2c[nH]c(=O)[nH]c2=O)S1]

(Z)-5-((2-imino-4-oxothiazolidin-5-ylidene)methyl)pyrimidine-2,4(1H,3H)-dione 13k Compound 13k: $^1$H NMR (DMSO) δ: 11.47 (2H, bs), 9.17 (1H, bs), 8.93 (1H, s), 7.74 (1H, s), 7.34 (1H, s); $^{13}$C NMR (DMSO) δ: 180.76, 176.55, 163.07, 150.56, 144.50, 126.74, 122.56, 107.66.

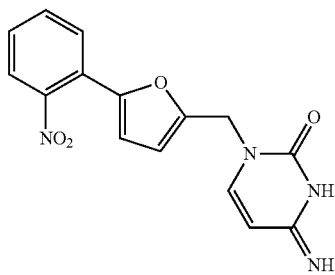 [SMILES: N=c1ccn(Cc2ccc(-c3ccccc3[N+](=O)[O-])o2)c(=O)[nH]1]

4-imino-1-((5-(2-nitrophenyl)furan-2-yl)methyl)-3,4-dihydropyrimidin-2(1H)-one

Compound 15a: $^1$H NMR (DMSO) δ: 7.87 (1H, d, J=8.0 Hz), 7.82 (1H, d, J=7.5 Hz), 7.73 (1H, t, J=7.5 Hz), 7.58 (1H, d, J=7.0 Hz), 7.56 (1H, t, J=8.5 Hz), 7.16 (1H, s), 7.09 (1H, s), 6.86 (1H, d, J=3.5 Hz), 6.48 (1H, d, J=3.0 Hz), 5.72 (1H, d, J=7.5 Hz), 4.89 (2H, s); 13C NMR δ: 166.33, 155.63, 152.62, 147.82, 147.11, 145.59, 132.72, 129.41, 128.80, 124.16, 122.73, 110.07, 110.92, 94.21, 44.57.

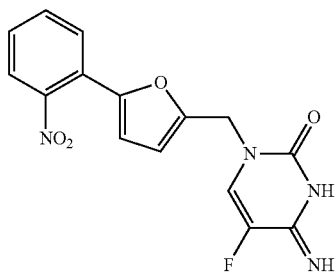 [SMILES: N=c1[nH]c(=O)n(Cc2ccc(-c3ccccc3[N+](=O)[O-])o2)cc1F]

5-fluoro-4-imino-1-((5-(2-nitrophenyl)furan-2-ylmethyl)-3,4-dihydropyrimidin-2(1H)-one Compound 15b: $^1$H NMR (DMSO) δ: 7.85 (1H, d, J=6.6 Hz), 7.81 (1H, d, J=8.4 Hz), 7.78 (1H, d, J=8.3 Hz), 7.69 (1H, t, J=7.5 Hz), 7.65 (1H, bs), 7.53 (1H, t, J=7.8 Hz), 7.44 (1H, bs), 6.83 (1H, d, 3.3 Hz), 6.47 (1H, d, J=3.3 Hz), 4.81 (2H, s); $^{13}$C NMR (DMSO) δ: 158.16 (d, J=13.1 Hz), 154.06, 152.32, 148.11, 147.29, 136.26 (d, J=239.1 Hz), 132.84, 130.26 (d, J=30.5 Hz), 129.57, 128.92, 124.28, 122.82, 111.19, 111.12; $^{19}$F NMR (DMSO) δ: 163.09.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A compound having the ability to increase read through of premature termination codons (PTCs) in RNA, a pharmaceutically acceptable salt thereof, having a structure of formula (VIII):

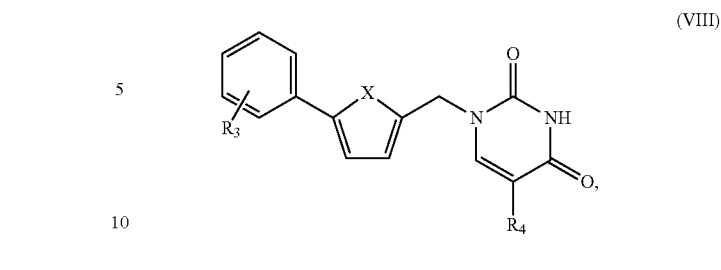

wherein:

X is O;

$R_3$ is an ortho, meta, or para group and is a hydrogen, halo, or nitro; and $R_4$ is hydrogen, —C(O)H, halo, or a C1-C6 group.

2. A compound having the ability to read through premature termination codons (PTCs) in RNA, a pharmaceutically acceptable salt thereof, having a structure of formula (IX):

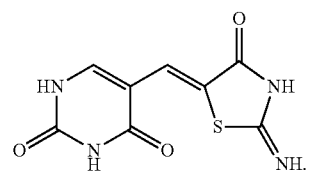

3. The compound of claim 1 where the compound is selected from:

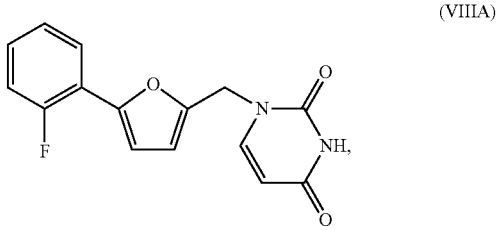

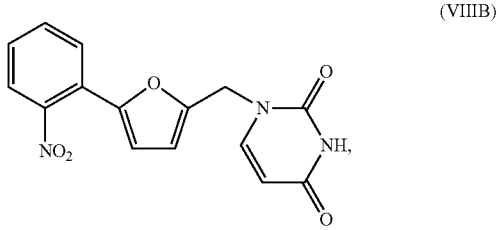

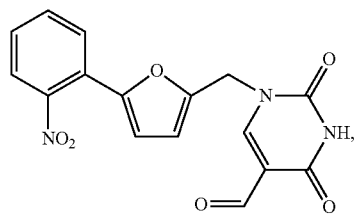

-continued

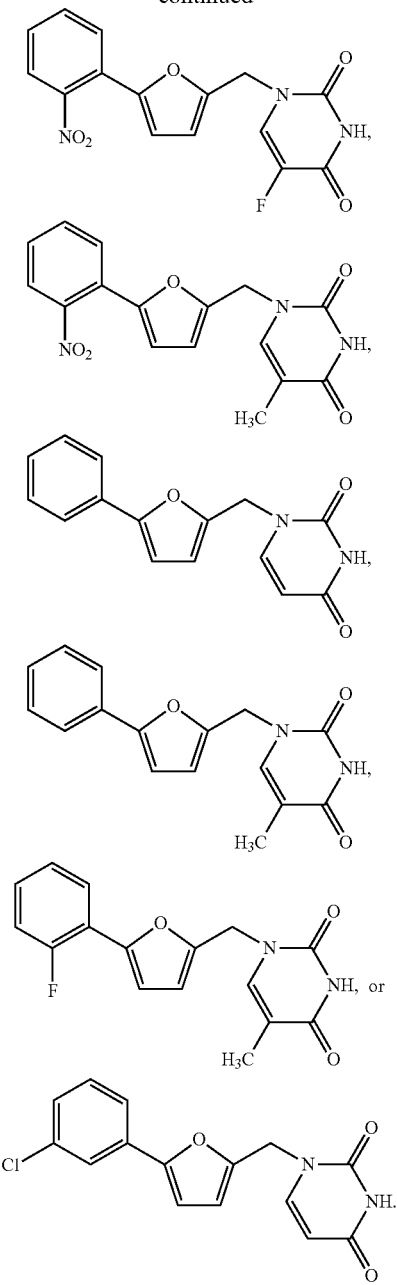

4. The compound of claim 1, having one of the following formulas:

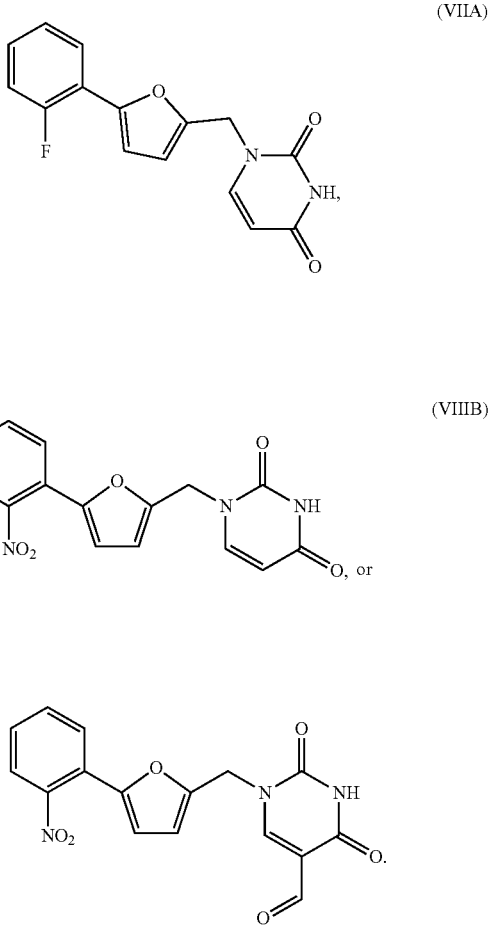

5. A composition comprising the compound of claim 1 and a pharmaceutically acceptable carrier.

6. A method of treating or ameliorating a medical condition associated with premature termination codons (PTCs) in RNA, comprising: administering to a subject a compound according to claim 1, wherein the subject has an ATM gene that encodes one or more PTCs, or a DMD gene that encodes one or more PTCs.

* * * * *